US012668844B2

(12) United States Patent
Koh et al.

(10) Patent No.: US 12,668,844 B2
(45) **Date of Patent: \*Jun. 30, 2026**

(54) METHODS FOR SEQUENCING CELL-FREE RNA

(71) Applicant: The Board of Trustees of the Leland Stanford Junior University, Stanford, CA (US)

(72) Inventors: Lian Chye Winston Koh, Stanford, CA (US); Stephen R. Quake, Stanford, CA (US); Hei-Mun Christina Fan, Fremont, CA (US); Wenying Pan, Stanford, CA (US)

(73) Assignee: The Board of Trustees of the Leland Stanford Junior University

( * ) Notice: Subject to any disclaimer, the term of this patent is extended or adjusted under 35 U.S.C. 154(b) by 0 days.

This patent is subject to a terminal disclaimer.

(21) Appl. No.: 18/913,930

(22) Filed: Oct. 11, 2024

(65) Prior Publication Data

US 2026/0103749 A1 Apr. 16, 2026

Related U.S. Application Data

(63) Continuation of application No. 16/836,498, filed on Mar. 31, 2020, now Pat. No. 12,565,679, which is a
(Continued)

(51) Int. Cl.
| | |
|---|---|
| *C12Q 1/68* | (2018.01) |
| *C12Q 1/6806* | (2018.01) |
| *C12Q 1/686* | (2018.01) |

(52) U.S. Cl.
CPC ........... *C12Q 1/686* (2013.01); *C12Q 1/6806* (2013.01)

(58) Field of Classification Search
CPC ....................................................... C12Q 1/68
See application file for complete search history.

(56) References Cited

U.S. PATENT DOCUMENTS

| | | | |
|---|---|---|---|
| 5,432,054 A | 7/1995 | Saunders et al. | |
| 5,629,147 A | 5/1997 | Asgari et al. | |
(Continued)

FOREIGN PATENT DOCUMENTS

| | | |
|---|---|---|
| AU | 2013211850 | 9/2014 |
| CA | 2838562 | 2/2013 |
(Continued)

OTHER PUBLICATIONS

Twine, N., et al. Whole transcriptome sequencing reveals gene expression and splicing differences in brain regions affected by Alzheimer's disease. PLoS one, vol. 6(1), e16266, p. 1-13, (2011).*
(Continued)

*Primary Examiner* — Aaron A Priest
(74) *Attorney, Agent, or Firm* — Pamela J. Sherwood; Bozicevic Field & Francis LLP

(57) ABSTRACT

In an aspect, a method comprises obtaining cell-free ribonucleic acid (RNA) from a plasma sample of a subject; converting the cell-free RNA into complementary deoxyribonucleic acid (cDNA), thereby producing sample cDNA; and sequencing the sample eDNA to determine a level of the sample cDNA that corresponds to a set of RNA transcripts.

12 Claims, 37 Drawing Sheets

Related U.S. Application Data continuation of application No. 15/034,746, filed on May 5, 2016, now abandoned, which is a continuation of application No. PCT/US2014/064355, filed on Nov. 6, 2014, said application No. 16/836,498 is a continuation-in-part of application No. 13/752,131, filed on Jan. 28, 2013, now abandoned.

(60) Provisional application No. 61/900,927, filed on Nov. 6, 2013, provisional application No. 61/591,642, filed on Jan. 27, 2012.

(56) References Cited

U.S. PATENT DOCUMENTS

| | | | |
|---|---|---|---|
| 6,664,056 B2 | 12/2003 | Lo et al. | |
| 7,235,359 B2 | 6/2007 | Lo et al. | |
| 7,713,693 B1 | 5/2010 | Shah et al. | |
| 7,829,285 B2 | 11/2010 | Lo et al. | |
| 8,486,626 B2 * | 7/2013 | Umansky | C12Q 1/6883 435/6.12 |
| 10,240,200 B2 | 3/2019 | Koh et al. | |
| 2002/0045176 A1 | 4/2002 | Lo et al. | |
| 2003/0108871 A1 | 6/2003 | Kaser | |
| 2004/0067507 A1 | 4/2004 | Nolan et al. | |
| 2004/0086511 A1 | 5/2004 | Zack et al. | |
| 2004/0137470 A1 | 7/2004 | Dhallan et al. | |
| 2004/0180048 A1 | 9/2004 | Zack et al. | |
| 2004/0203037 A1 | 10/2004 | Lo et al. | |
| 2006/0003342 A1 | 1/2006 | Bianchi et al. | |
| 2006/0166242 A1 | 7/2006 | Pennell et al. | |
| 2007/0179197 A1 * | 8/2007 | Henderson | A61P 25/28 514/547 |
| 2007/0202525 A1 | 8/2007 | Quake et al. | |
| 2008/0009467 A1 | 1/2008 | Henderson | |
| 2009/0170113 A1 | 7/2009 | Quake et al. | |
| 2009/0311269 A1 * | 12/2009 | Allen | A61K 31/7088 435/6.14 |
| 2009/0318304 A1 | 12/2009 | Drmanac et al. | |
| 2010/0047779 A1 | 2/2010 | Butt et al. | |
| 2010/0120787 A1 | 5/2010 | Sutcliffe et al. | |
| 2010/0145131 A1 | 6/2010 | Grinberg-Rashi et al. | |
| 2011/0003294 A1 | 1/2011 | Liew | |
| 2011/0008805 A1 | 1/2011 | Urdea et al. | |
| 2011/0144076 A1 | 6/2011 | Williams et al. | |
| 2011/0150775 A1 | 6/2011 | Slonim et al. | |
| 2011/0189679 A1 | 8/2011 | Kurn et al. | |
| 2011/0263441 A1 | 10/2011 | Golub et al. | |
| 2013/0089855 A1 * | 4/2013 | Mitsuhashi | C12Q 1/6883 435/6.12 |
| 2013/0252835 A1 | 9/2013 | Koh et al. | |
| 2014/0141986 A1 * | 5/2014 | Spetzler | C12Q 1/6886 435/7.1 |
| 2014/0304845 A1 | 10/2014 | Loboda et al. | |
| 2015/0065355 A1 | 3/2015 | Meder et al. | |
| 2015/0211070 A1 * | 7/2015 | Seligson | C12Q 1/70 506/3 |
| 2016/0017420 A1 | 1/2016 | Koh et al. | |
| 2016/0289762 A1 * | 10/2016 | Koh | C12Q 1/6883 |
| 2017/0145507 A1 | 5/2017 | Koh et al. | |
| 2017/0145508 A1 | 5/2017 | Koh et al. | |
| 2017/0145509 A1 | 5/2017 | Koh et al. | |

FOREIGN PATENT DOCUMENTS

| | | |
|---|---|---|
| CA | 2863035 | 8/2013 |
| CN | 104334742 | 2/2015 |
| EP | 2807277 | 12/2014 |
| JP | 2010/536372 | 12/2010 |
| JP | 2015511122 | 4/2015 |
| WO | WO2004065629 | 8/2004 |
| WO | WO2009009457 | 1/2009 |
| WO | WO2009025852 | 2/2009 |
| WO | WO2009093254 | 7/2009 |
| WO | WO201156763 | 5/2011 |
| WO | WO20111071893 | 6/2011 |
| WO | WO2011156734 | 12/2011 |
| WO | WO2012004371 | 1/2012 |
| WO | WO2012012693 | 1/2012 |
| WO | WO-2012145363 A1 * | 10/2012 | A61P 25/28 |
| WO | WO2013007708 | 1/2013 |
| WO | WO2013022953 | 2/2013 |
| WO | WO2013049674 | 4/2013 |
| WO | WO2013113012 | 8/2013 |
| WO | WO2014150198 | 9/2014 |
| WO | WO2015069900 | 5/2015 |
| WO | WO2016196945 | 12/2016 |
| WO | WO2017156310 | 9/2017 |

OTHER PUBLICATIONS

Booij, et al "A Gene Expression Pattern in Blood for the Early Detection of Alzheimer's Disease" Journal of Alzheimer's Disease 23 (2011) 109-119.*
ADORA3 information from GeneCards Human Gene Database, printed in Jul. 8, 2017 from www.genecards.org, pp. 1-17.
Bianchi et al., 1990, Isolation of fetal DNA from nucleated erythrocytes in maternal blood, Proc Nail Acad Sci USA 7:3279-83.
Breuleux, "Role of Heregulin in Human Cancer", Cellular and Molecular Life Sciences, Sep. 2007, pp. 2358-2377, vol. 64, Issue 18, Springer, Berlin, Germany.
Butt et al., "Overview of circulating nucleic acids in plasma/serum", Annals of the New York Academy of Sciences, Dec. 1, 2008, pp. 236-242, vol. 1137, Wiley, Hoboken NJ.
Cahoy et al., "A transcriptome database for astrocytes, neurons, and oligodendrocytes: a new resource for understanding brain development and function", Journal of Neuroscience, Jan. 2, 2008, pp. 264-278, 28(1).
Chan et al., "Aberrant Concentrations of Liver-Derived Plasma Albumin mRNA in Liver Pathologies", Clinical Chemistry, Jan. 2010, pp. 82-S9, vol. 56, Issue 1, American Association for Clinical Chemistry, Washington, DC.
Chan, Ronna L. "Biochemical markers of spontaneous preterm birth in asymptomatic women." Bio Med research international Jan. 2014 (2014): 164081. (Year: 2014).
Chaussabel et al., "A modular analysis framework for blood genomics studies: application to systemic lupus erythematosus", Immunity, Jul. 18, 2008, pp. 150-164, 29(1).
Cheung et al. (2003) "Natural variation in human gene expression assessed in lymphoblastoid cells.", Nature Genetics, 33,422-425.
Das, et al. (2012) "A cell stabilizing reagent in Cell-Free DNATM BCT is formaldehyde free and has no adverse effects on DNA integrity", Conference Paper, Presented at the AACC annual meeting. p. 1-3.
EP13740984.3 The Extended European Search Report dated Jan. 14, 2016.
Examination Report for Australian Application No. 2013211850 dated Apr. 14, 2016, 4 pages.
Extended European Search Report for PCT/US2013/023471 dated Jan. 16, 2014.
Fehlbaum-Beurdeley, et al. (2010) "Toward an Alzheimer's disease diagnosis via high-resolution blood gene expression" Alzheimers Dement. Jan. 2010;6(1):25-38.
Fernando et al., (2010) "A new methodology to preserve the original proportion and integrity of cell-free fetal DNA in maternal plasma during sample processing and storage" Prenat Diagn 201 0; 30: 418-424.
Furneaux et al., "Characterization of a cDNA encoding a 34-kDa Purkinje neuron protein recognized by sera from patients with paraneoplastic cerebellar degeneration", Proc. Natl. Acad. Sci. USA, Apr. 1, 1989, pp. 2873-2877, vol. 86 No. 8, National Academy of Sciences, Washington, D.C.
Gahlan et al. (2012) "De novo sequencing and characterization of Picrorhiza kurrooa transcriptome at two temperatures showed major transcriptome adjustments" BMC Genomics 13(126), pp. 1-21.
Geekiyanage et al., "Blood Serum miRNA: Non-invasive Biomarkers for Alzheimer's Disease", Experimental Neurology, Jun. 2012, pp. 491-496, vol. 235, Issue 2, Elsevier, Amsterdam, Netherlands.

(56)          References Cited

OTHER PUBLICATIONS

GenBank Accession NM_004352 "*Homo sapiens* Cerebellin 1 Precursor (CBLN1), mRNA", Printed from https://www.ncbi.nlm. nih.gov, Apr. 20, 2010, pp. 1-5.
Genecard for ABHD17B gene, printed Jun. 16, 2017 from www. genecards.org, pp. 1-14.
Genecards ZNF717 Gene (protein coding), pritned in Jul. 5, 2017, pp. 1-16, from http://www.genecards.org.
Goldenberg et al. (2005) "Biochemical markers for the prediction of preterm birth.", Am J Ob Gyn 192: pp. S36-S46.
Goldfarb et al. (1983) "A numerically stable dual method for solving strictly convex quadratic programs.", Mathemtical Programming 27:1-33.
Gracien et al. (2010) "Paraneoplastic cerebellar degeneration mimicking development of secondary progressive multiple sclerosis in a patient with relapsing—remitting multiple sclerosis", Multiple Sclerosis Journal, 17(4) pp. 498-500, Sage Publications, Thousand Oaks, CA.
GTEX Protal Gene Page results for APP, from https://www.gtexportal. org/horne/gene/APP, printed on Oct. 25, 2022. (Year: 2022).
Guo et al., "Genome-wide Survey of Tissue-Specific microRNA and Transcription Factor Regulatory Networks in 12 Tissues", Scientific Reports, Jun. 3, 2014, pp. 1-9, vol. 4, Article No. 5150, Macmillan Publishers Limited, Basingstoke, United Kingdom.
Hafner et al., 2004, Differential gene expression of Eph receptors and ephrins in benign human tissues and cancers, Cllinical Chemistry 50{3}:490-99.
Han et al., "Janus-like opposing roles of CD47 in autoimmune brain inflammation in humans and mice" J Exp Med., Jun. 25, 2012, pp. 1-10, Rockefeller University Press, New York, NY.
Hanyu, et al (2022) "Characterization of Alzheimer's Disease Subtypes Based on Magnetic Resonance Imaging and Perfusion Single-Photon Emission Computed Tomography" J Alzheimers Dis. 2022;87(2):781-789.
Henson, et al. (2009) "DNA C-circles are specific and quantifiable markers of alternative-lengthening-of-telomeres activity" Nature Biotechnology, vol. 27, pp. 1182-1186.
Herzenberg et al., 1979, Fetal cells in the blood of pregnant women: detection and enrichment by fluorescence-activaled cell sorting, Proc. Nail. Acad. Sci. USA 76{3} 1453-55.
Heung Dissertation, "Development and Characterisation of Circulating RNA Markers", The Chinese University of Hong Kong, Aug. 2009, pp. 1-239, ProQuest LLC, Ann Arbor, MI.
Hiller et al. (2009) "Identifiability of isoform deconvolution from junction arrays and RNA-Seq." *Bioinformatics*, 25(23), pp. 3056-3059.
Ho et al., "Gene Expression Profiling of Liver Cancer Stem Cells by RNA-Sequencing", PLoS One, May 14, 2012, pp. 1-16, vol. 7, Issue 5, e37159, PLoS One, San Francisco, CA.
Hoshikawa, 2003, Hypoxia induces different genes in the lungs of rats compared with mice, Physiol Genomics 2:209-219.
Human Protein Atlas, primary reference Uhlen et al Proteomics Tissue-based map of the human proteome Science, 347:6220 (Jan. 23, 2015), retrieved from the internet on Dec. 6, 2016 (http://www_proteinatlas.org/search/protein_class:COSMIC%20Somatic% 20Mutations.
Human Protein Atlas, primary reference Uhlen et al Proteomics Tissue-based map of the human proteome Science, 347:6220 (Jan. 23, 2015), retrieved from the internet on Dec. 6, 2016 (http://www. proteinallas.org/humanproteome/tissue+specific.
Illumina (2011) "White Paper: Sequencing: RNA-Seq Data Comparison with Gene Expression Microarrays." pp. 1-8. rna-seq-to-arrays-comparison-white-paper-470-2011-001.pdf i llu m ina.com/ contenUdam/ill u mina-marketing/docu ments/products/whitepapers/ rna-seq-to-arrays-com parison-white-paper-470-2011-001. pdf.
International Application No. PCT/US2017/021637 International Preliminary Report on Patentability Mailed Sep. 11, 2018.
International Application No. PCT/US2017/021637 International Search Report and Written Opinion Mailed Jun. 6, 2017.

International Search Report and Written Opinion for PCT/US13/ 23471, dated Apr. 11, 2013,7 pages.
International Search Report and Written Opinion mailed on Mar. 5, 2015, for International Patent Application No. PCT/US14/64355, filed Nov. 6, 2014 (10 pages).
James H Bullard, et al. "Evaluation of statistical methods for normalization and differential expression in mRNA-Seq experiments" BMC Bioinformatics 2010, 11 :94 (Year: 2010).
Kallio et al. (2011) "Chipster: user-friendly analysis software for microarray and other high-throughput data." *BMC genomics*, 12(507), pp. 1-14.
Koh (2014) "Noninvasive in vivo monitoring of tissue-specific global gene expression in humans.", PNAS 111(20), pp. 7361-7366.
Koh et al. (2012) "730-Profiling maternal plasma cell-free RNA by RNA-sequencing: a comprehensive approach" American Journal of Obstetrics and Gynecology, 206(1), Supplement, S324.
Koschmieder et al. (2012) "Tools for managing and analyzing microarray data." *Briefings in bioinformatics*, 13(1), pp. 46-60.
Kylie K. Hornaday, et al. "Is there a maternal blood biomarker that can predict spontaneous preterm birth prior to labour onset? A systematic review" PloS one 17.4 (2022): e0265853. (Year: 2022).
Lage et al. (2008) "A large-scale analysis of tissue-specific pathology and gene expression of human disease genes and complexes" PNAS, Dec. 30, 2008, vol. 105, No. 52, pp. 20870-20875.
Li et al., "Blood transcriptomics and metabolomics for personalized medicine", Computational and Structural Biotechnology Journal, 2016, pp. 1-7, 14.
Li et al., "Circulatory miR-34a as an RNA-based, noninvasive biomarker for brain aging", Aging, Oct. 2011, pp. 985-1002, vol. 3, No. 10, Impact Journals, LLC, Orchard Park, NY.
Li et al., "Molecular signatures of antibody responses derived from a systems biology study of five human vaccines", Nature Immunology, Feb. 2014, pp. 195-204, 15(2).
Li et al., "Serum Circulating Human mRNA Profiling and Its Utility for Oral Cancer Detection", Journal of Clinical Oncology, Apr. 10, 2006, pp. 1754-1760, vol. 24, No. 11, American Society of Clinical Oncology, Alexandria, VA.
Lo et al., 2007, Plasma placental RNA allelic ratio permits noninvasive prenatal chromosomal aneuploidy detection, Nature Medicine 13(2):218-223.
Lo, 2009, Noninvasive prenatal detection of fetal chromosomal aneuploidies by maternal plasma nucleic acid analysis: review of the current state of the art, BJOG 116(2): 152-157.
Ishigaki et al. "Differentially expressed genes in sporadic amyotrophic lateral sclerosis spinal cords—screening by molecular indexing and subsequent cDNA microarray analysis", FEBS Letters, Oct. 16, 2002, pp. 354-358, 531, Elsevier, Amsterdam, Netherlands.
Makhseed, 2003, Pro-inflammatory maternal cytokine profile in preterrn delivery, Amm J Rep Immunol49:308-318.
Maron et al., 2007, Gene expression analysis in pregant women and their infants identifies unique fetal biomarkers that Circulate in maternal blood, J Clin Investigation 117(10):3007-3019.
Mcgill (2003 ) "Tutorial: RMA Analysis using the Microarray Platform Website." pp. 1-12. "https://genomequebec.mcgill.ca/ nanuqAdministration/download/MicroarrayRMATutorial_en.pdf" (Year: 2003).
Mitchell et al., "Circulating microRNAs as stable blood-based markers for cancer detection", Proceedings of the National Academy of Sciences, Jul. 29, 2008, pp. 10513-10518, PNAS, Washington, DC.
Miura, 2010, Identification of pregnancy-associated microRNAs in maternal plasma, Clin Chern 56(11):1767-1771.
Miyamoto et al., 2008, Detection of Cell-Free, Liver-Specific mRNAs in Peripheral Blood from Rats with Hepatotoxicity: Potential Toxicological Biomarker for Safety Evaluation, Toxicological Sciences 106{2}:538-45.
Morozova et al, 2009, Applications of new sequencing technologies for transcriptome analysis, Ann Rev Gen Hum Ge 0(1):135-151.
Ng et al., 2003, The concentration of circulating corticotropin-releasing hormone mRNA in maternal plasma is increased in preeclampsia, Clinical Chemistry 49{5}:727-31.
Partial supplementary European Search Report mailed Oct. 12, 2015, for European patent application 13740984.3 which is a

(56)                    References Cited

OTHER PUBLICATIONS regional stage entry of International Patent Application No. PCT/US2013/023471 with International Filing Date Jan. 28, 2013 (9 pages).

Pavlidis et al., 2001, Analysis of strain and regional variation in gene expression in mouse brain, Genome Biology 2 10):1-15.

Pawelczyk et al., 2010, Spontaneous preterrm labor is associated with an increase in the proinflammatory signal transducer TLR4 receptor on maternal blood monocytes, BMC Preg Childbirth 10(1):66 pp. 1-9.

Pepke et al. (2009) "Computation for ChIP-seq and RNA-seq studies." *Nature methods*, 6(Suppl 11), pp. S22-S32.

Poon et al., 2000, Presence of fetal RNA in maternal plasma, Clinical Chemistry 46{11 ): 1832-34.

Porter et al., A Sage (serial analysis of gene expression) view of breast tumor progression:, Cancer Res., Aug. 1, 2001, pp. 5697-5702, 61(15).

Purwosunu et al. "Prediction of preeclampsia by analysis of cell-free messenger RNA in maternal plasma" American Journal of Obstetrics and Gynecology, vol. 200, Issue 4, Apr. 2009, pp. 386.e1-386.e7 (Year: 2009).

Rao et al., "MicroRNAs as biomarkers for CNS disease", Frontiers in Molecular Neuroscience, Nov. 26, 2013, pp. 1-13, vol. 6, Article 39, Frontiers Media S.A, Lausanne, Switzerland.

Ravetti et al (2010) " Uncovering Molecular Biomarkers That Correlate Cognitive Decline with the Changes of Hippocampus' Gene Expression Profiles in Alzheimer's Disease" Plos, 5;4 pp. 1-42.

Redell et al., 2010, Human Traumatic Brain Injury Alters Plasma microRNA Levels, Journal of Neurotrauma 7:2147-56.

Scherzer, "Chipping away at diagnostics for neurodegenerative diseases" Neurobiology of Disease, Mar. 10, 2009, pp. 148-156, 35, Elsevier, Amsterdam, Netherlands.

Schott et al., "Brain Biopsy in Dementia: Clinical Indications and Diagnostic Approach", Acra Neuropathol, Sep. 2010, pp. 327-341, vol. 120, Springer, Berlin, Germany.

Segal et al., "Module networks: identifying regulatory modules and their condition-specific regulators from gene expression data", Nature Genetics, Jun. 2003, pp. 166-176, 34(2).

Semenov et al.(2012) "Unbiased approach to profile the variety of small non-coding RNA of human blood plasma with massively parallel sequencing technology", Expert Opinion on Biological Therapy, 12:sup1, S43-S51.

Sergueeva et al. (2012) "Novel Tissue Types for the Development of Genomic Biomarkers". Chapter of the book 3iomarker, pp. 271-294, InTech, Croatia, European Union.

Siegel et al. (2012) "Circulating microRNAs involved in multiple sclerosis", Mal Biol Rep, 39(5), pp. 6219-6225, Springer, New York City, NY.

Spurgeon et al., 2008, High throughout gene expression measurement with real lime PCR in a microfluidic dynamic array, PLoS One 3{2}:1-7.

Staal et al. (2003) "DNA microarrays for comparison of gene expression profiles between diagnosis and relapse of precursor-B acute lymphoblastic leukemia: choice of technique and purification influence the identification of potential diagnostic markers.", Leukemia 17, pp. 1324-1332.

Suet al., 2004, A gene atlas of the mouse and human protein-encoding transcriplomes, Proc Nail Acad Sci USA, 101 16):6062-67.

Tissue gene expression data, HPA RNA-Seq normal tissues, CAMK1G calcium/calmodulin dependent protein kinase IG [*Homo sapiens* (human)], printed from https://www.ncbi.nlm.nih.gov/gene/57172/?report=expression (Year: 2022).

U.S. Appl. No. 15/034,746 Non-Final Office Action Mailed Mar. 29, 2017.

U.S. Appl. No. 15/034,746 Office Action dated Jun. 27, 2018.

U.S. Appl. No. 15/034,746 Office Action dated Mar. 8, 2019.

U.S. Appl. No. 15/034,746 Office Action dated Nov. 1, 2017.

U.S. Appl. No. 15/034,746 Office Action dated Oct. 4, 2019.

Viale et al., 1997, The melanin-concentrating hormore gene in human: flanking region analysis, fine chromosome mapping, and tissue-specific expression, Molecular Brain Research 46:243-55.

Villani et al., "Cytokines, Neurotrophins, and Oxidative Stress in Brain Disease From Mucopolysaccharidosis IIIB", Journal of Neuroscience Research, Feb. 15, 2007, pp. 612-622, vol. 85, Issue 3, Wiley, Hoboken, NJ.

Wetmore et al., (2010) "Quantitative analyses and transcriptomic profiling of circulating messenger RNAs as biomarkers of rat liver injury," Hepatology, 51(6), pp. 2127-2139.

Whitehead et al. (2005) "Variation in tissue-specific gene expression among natural populations" Genome Biology 2005, 6: R13.

Wilhelm et al., "RNA-Seq—quantitative measurement of expression through massively parallel RNA-sequencing" Methods, Jul. 2009, pp. 249-257,vol. 48, Issue 3, Elsevier, Amsterdam, Netherlands.

Wu et al., 2009, BioGPS: an extensible and customizable portal for querying and organizing gene annotation resources, Genome Biology 10{11):1-8.

Xiao et al., 2010, TiSGeD: a database for tissue-specific genes, Bioinformatics 26{9):1273-75.

Wang, et al "RNA-Seq: a revolutionary tool for transcriptomics" Nature Reviews Genetics. vol. 10, pp. 57-63.

Matsui, et al "Expression of APP pathway mRNAs and proteins in Alzheimer's disease" Brain Research (2007) p. 116-123.

Xiaoli Li, et al "Circulatory miR-34a as an RNA-based, noninvasive biomarker for brain aging" Aging, Oct. 2011 vol. 3. No 10, p. 985-1002 (.

Booij, et al "A Gene Expression Pattern in Blood for the Early Detection of Alzheimer's Disease" Journal of Alzheimer's Disease 23 (2011) 109-119 (Year: 2011).

Thompson et al. (2010). "Single Molecule Sequencing with a HeliScope Genetic Analysis System." Current protocols in molecular biology (Print) suppl 92.1 7.10.1-7.10.14. Web.

Swarup et al. (2007). "Circulating (Cell-Free) Nucleic Acids—A Promising, Non-Invasive Tool for Early Detection of Several Human Diseases." FEBS letters 581.5 (2007): 795-799. Web.

Klickstein et al. (1995) "Preparation of Insert DNA from messenger RNA" Current Protocols in Molecular Biology 5.5.1-5.5.14).

(2011) Qiagen Sample and Assay Technologies: "miScript PCR System Handbook".

(2001) Thermo Fisher Scientific Invitrogen "cDNA Synthesis System" 36 pages.

Kroh et al. (2010) "Analysis of Circulating microRNA Biomarkers in Plasma and Serum Using Quantitative Reverse Transcription-PeR (qRT-PCR)." Methods (San Diego, Calif.) 50.4 (2010): 298-301.

Bruder et al., (2010) "Transcriptome sequencing and development of an expression microarray platform for the domestic ferret." BMC Genomics, vol. 11 No. 1:251.

Li et al., (2006) "Serum circulating human mRNA profiling and its utility for oral cancer detection." Journal of Clinical Oncology, vol. 24 No. 1, pp. 1754-1760.

Shiroguchi et al., (2012) "Digital RNA sequencing minimizes sequence-dependent bias and amplification noise with optimized single-molecule barcodes." Proceedings of the National Academy of Sciences, vol. 109, No. 4, pp. 1347-1352.

Xie et al., (2011) "An integrative analysis of DNA methylation and RNA-Seq data for human heart, kidney and liver." BMC Systems Biology, vol. 5, Suppl 3: n. pag. Web.

* cited by examiner

| Female Pregnancy Associated Differential Expressed Transcripts | |
|---|---|
| PAPPA | PAPPA antisense RNA (non-protein coding); pregnancy-associated plasma protein A, pappalysin 1 |
| TEAD3 | TEA domain family member 3 |
| ADM | adrenomedullin |
| CSH1 | chorionic somatomammotropin hormone 1 (placental lactogen) |
| CSH2 | chorionic somatomammotropin hormone 2 |
| INSL4 | insulin-like 4 (placenta) |
| PGF | placental growth factor |
| PSG1 | pregnancy specific beta-1-glycoprotein 1 |
| PSG11 | pregnancy specific beta-1-glycoprotein 11 |
| PSG2 | pregnancy specific beta-1-glycoprotein 2 |
| PSG3 | pregnancy specific beta-1-glycoprotein 3 |
| PSG5 | pregnancy specific beta-1-glycoprotein 5 |
| PSG6 | pregnancy specific beta-1-glycoprotein 6 |
| PSG4,PSG8 | pregnancy specific beta-1-glycoprotein 7;pregnancy specific beta-1-glycoprotein 8; pregnancy specific beta-q-glycoprotein 4 |
| PSG9 | pregnancy specific beta-1-glycoprotein 9 |
| PRLR | prolactin receptor |
| SFR4 | secreted frizzled-related protein 4 |
| SPP1 | secreted phosphoprotein 1 |

FIG. 1

Plots of the Two main Principle Component for cell free RNA transcripts level

Each data point is a time point taken from an individual patient
---- Premature Patient
—— Normal Pregnancy
---- BiLobed Placenta
······ Non-Pregnant Controls

FIG. 3B-1

| FIG. 3B-1 |
| FIG. 3B-2 |

FIG. 3B

| Ranking by Significance | Gene Name |
|---|---|
| 1 | PVALB |
| 2 | CLCN3 |
| 3 | ITGA2B |
| 4 | LTV1 |
| 5 | HIST1H4B |
| 6 | TREML1 |
| 7 | NPTN |
| 8 | LSM2 |
| 9 | SCGB1C1 |
| 10 | NOP10 |
| 11 | MFSD1 |
| 12 | MALAT1 |
| 13 | GDI1 |
| 14 | HIST1H1C |
| 15 | HIST1H4H |
| 16 | CD226 |
| 17 | ITM2B |
| 18 | MLLT6 |
| 19 | ANO6 |
| 20 | ITGB3 |

FIG. 4

Figures 5, 6:
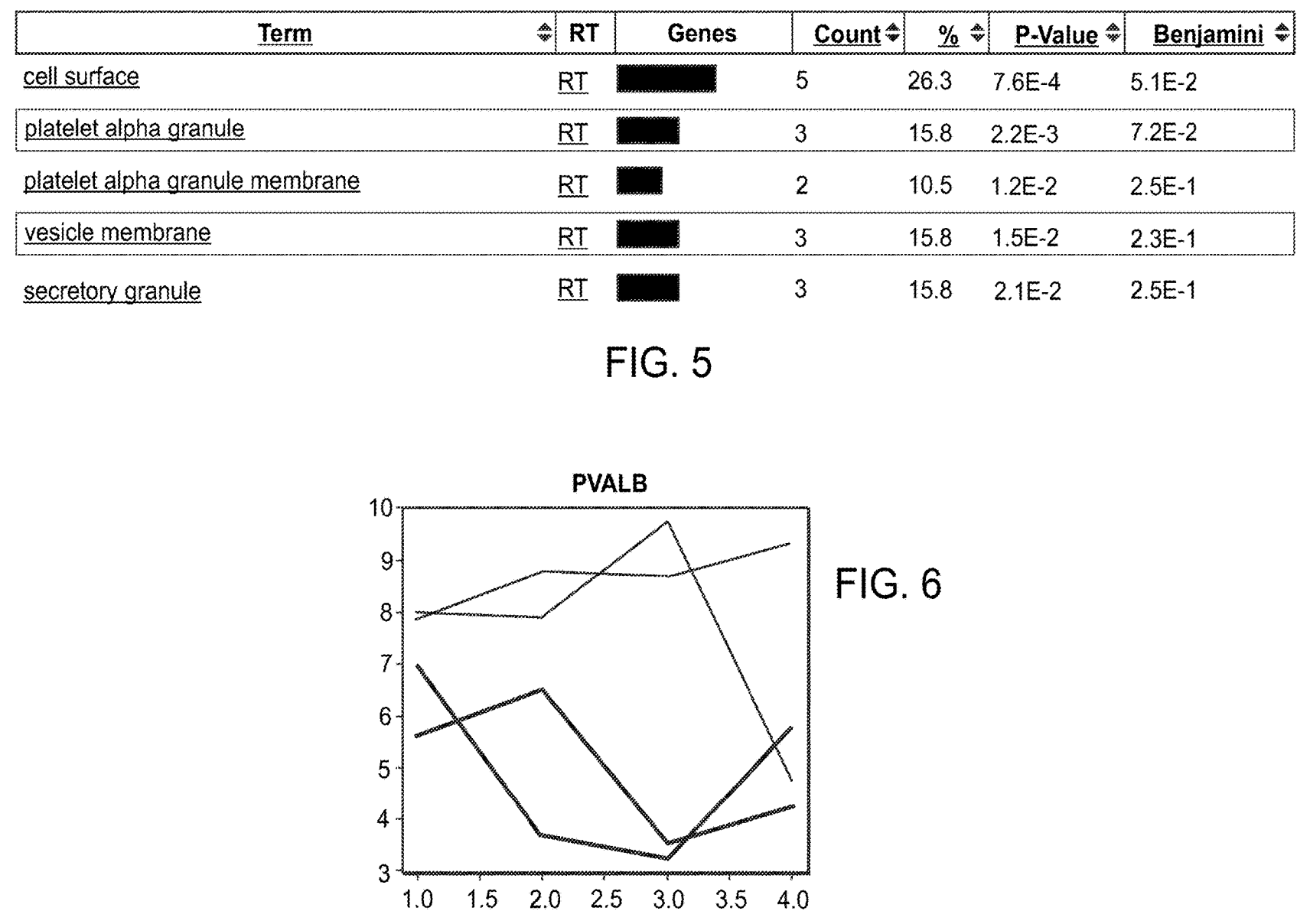

| Term | RT | Genes | Count | % | P-Value | Benjamini |
|------|----|----|-------|----|---------|-----------|
| cell surface | RT | ▮ | 5 | 26.3 | 7.6E-4 | 5.1E-2 |
| platelet alpha granule | RT | ▮ | 3 | 15.8 | 2.2E-3 | 7.2E-2 |
| platelet alpha granule membrane | RT | ▮ | 2 | 10.5 | 1.2E-2 | 2.5E-1 |
| vesicle membrane | RT | ▮ | 3 | 15.8 | 1.5E-2 | 2.3E-1 |
| secretory granule | RT | ▮ | 3 | 15.8 | 2.1E-2 | 2.5E-1 |

| FIG. 7A |
|---------|
| FIG. 7B |

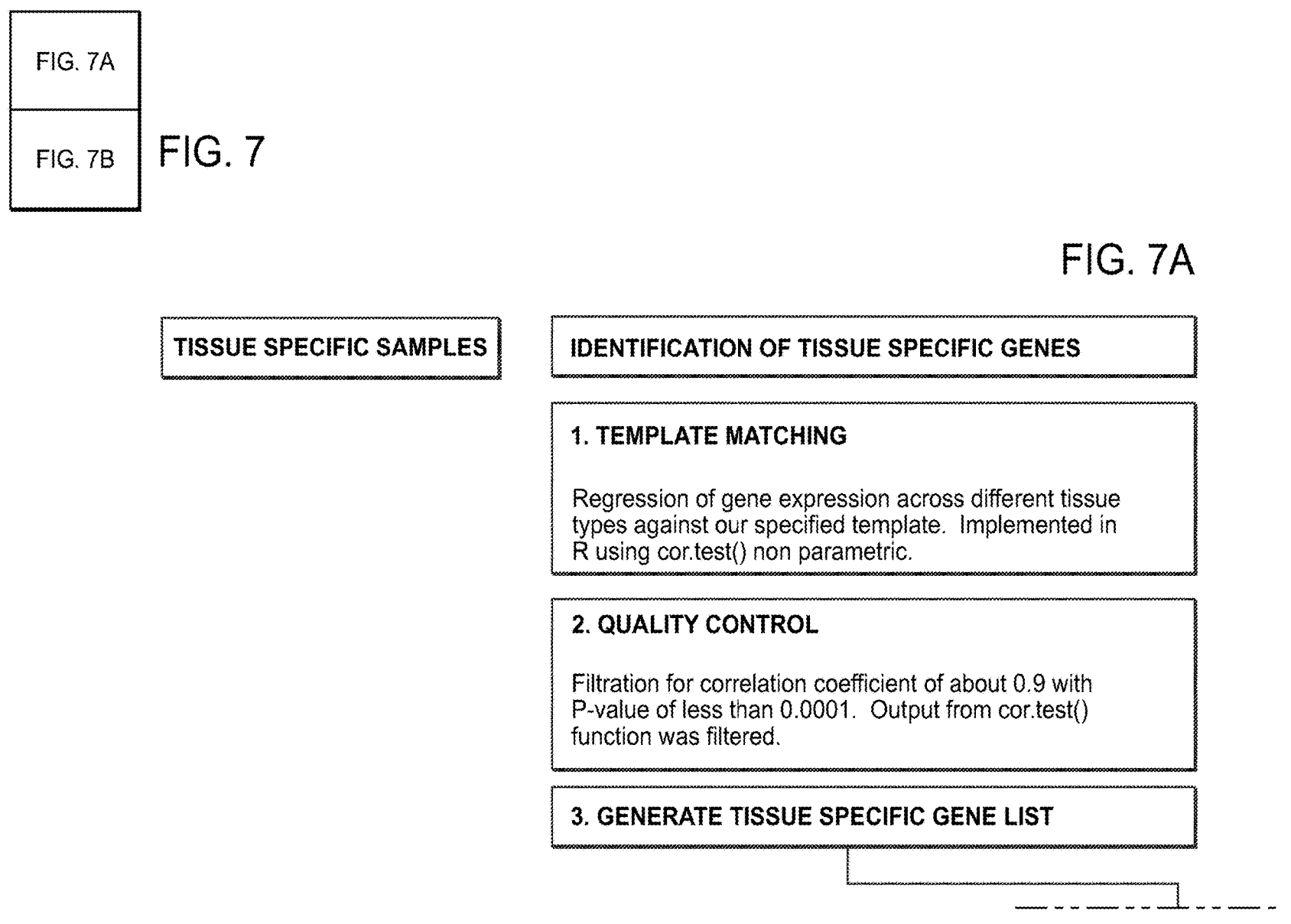

FIG. 7

TISSUE SPECIFIC SAMPLES

IDENTIFICATION OF TISSUE SPECIFIC GENES

1. TEMPLATE MATCHING

Regression of gene expression across different tissue types against our specified template. Implemented in R using cor.test() non parametric.

2. QUALITY CONTROL

Filtration for correlation coefficient of about 0.9 with P-value of less than 0.0001. Output from cor.test() function was filtered.

3. GENERATE TISSUE SPECIFIC GENE LIST

FIG. 7B

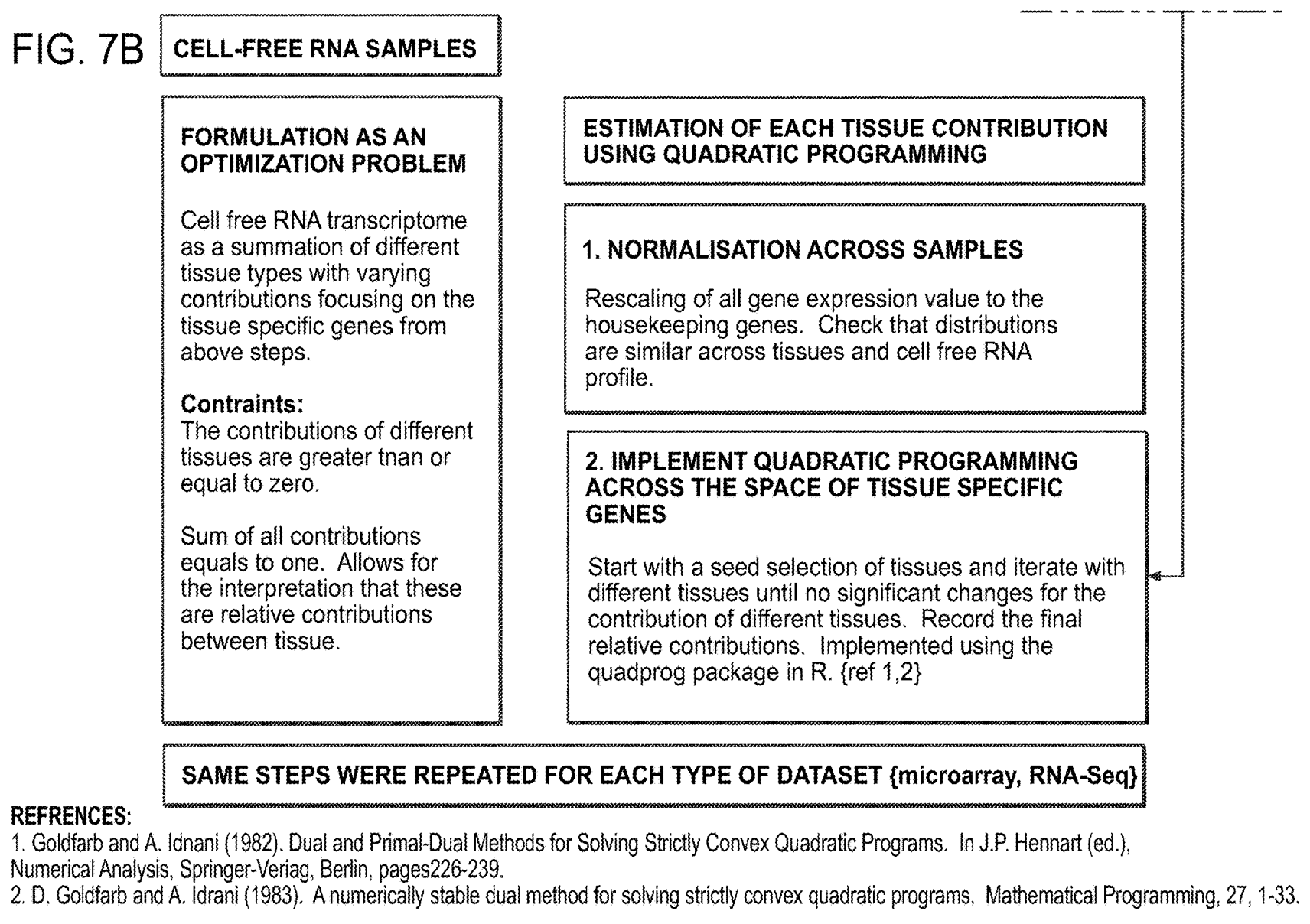

CELL-FREE RNA SAMPLES

FORMULATION AS AN OPTIMIZATION PROBLEM

Cell free RNA transcriptome as a summation of different tissue types with varying contributions focusing on the tissue specific genes from above steps.

Contraints:
The contributions of different tissues are greater than or equal to zero.

Sum of all contributions equals to one. Allows for the interpretation that these are relative contributions between tissue.

ESTIMATION OF EACH TISSUE CONTRIBUTION USING QUADRATIC PROGRAMMING

1. NORMALISATION ACROSS SAMPLES

Rescaling of all gene expression value to the housekeeping genes. Check that distributions are similar across tissues and cell free RNA profile.

2. IMPLEMENT QUADRATIC PROGRAMMING ACROSS THE SPACE OF TISSUE SPECIFIC GENES

Start with a seed selection of tissues and iterate with different tissues until no significant changes for the contribution of different tissues. Record the final relative contributions. Implemented using the quadprog package in R. {ref 1,2}

SAME STEPS WERE REPEATED FOR EACH TYPE OF DATASET {microarray, RNA-Seq}

REFRENCES:
1. Goldfarb and A. Idrani (1982). Dual and Primal-Dual Methods for Solving Strictly Convex Quadratic Programs. In J.P. Hennart (ed.), Numerical Analysis, Springer-Verlag, Berlin, pages226-239.
2. D. Goldfarb and A. Idrani (1983). A numerically stable dual method for solving strictly convex quadratic programs. Mathematical Programming, 27, 1-33.

FIG. 8A

List of selected Fetal Tissue Specific Transcripts

| Gene Symbol | Gene Full Name | Tissue |
|---|---|---|
| ACTB | actin, beta | Housekeeping |
| ADAM12 | ADAM metallopeptidase domain 12 | Placenta |
| AFP | alpha-fetoprotein | Fetal liver |
| ALPP | alkaline phosphatase, placental | Placenta |
| APOA4 | apolipoprotein A-IV | Fetal liver |
| BACE2 | beta-site APP-cleaving enzyme 2 | Placenta |
| CALCB | calcitonin-related polypeptide beta | Dorsal root ganglion |
| CGB | chorionic gonadotropin, beta polypeptide | Placenta |
| CRP | C-reactive protein, pentraxin-related | Fetal liver |
| DCX | doublecortin | Fetal brain |
| DLX2 | distal-less homeobox 2 | Fetal brain |
| EPB42 | erythrocyte membrane protein band 4.2 | BM-CD71+Early erythroid |
| EPX | eosinophil peroxidase | Fetal liver |
| EVX1 | even-skipped homeobox 1 | Fetal liver |
| FGA | fibrinogen alpha chain | Fetal liver |
| FOXG1 | forkhead box G1 | Fetal brain |
| GAPDH | glyceraldehyde-3-phosphate dehydrogenase | Housekeeping |
| GH2 | growth hormone 2 | Placenta |

| Gene | Description | Tissue |
|---|---|---|
| GNAZ | guanine nucleotide binding protein (G protein), alpha z polypeptide | Fetal brain |
| GPR116 | G protein-coupled receptor 116 | Fetal lung |
| GYPE | glycophorin E (MNS blood group) | BM-CD71+Early erythroid |
| HSD17B1 | hydroxysteroid (17-beta) dehydrogenase 1 | Placenta |
| JUP | junction plakoglobin | Bronchial epithelial cells |
| KRT81 | keratin 81 | Placenta |
| MEF2C | myocyte enhancer factor 2C | Fetal brain |
| MN1 | meningioma (disrupted in balanced translocation) 1 | Fetal brain |
| NPY1R | neuropeptide Y receptor Y1 | Fetal brain |
| NTSR1 | neurotensin receptor 1 (high affinity) | Fetal brain |
| OAZ1 | ornithine decarboxylase antizyme 1 | Housekeeping |
| PSG7 | pregnancy specific beta-1-glycoprotein 7 (gene/pseudogene) | Placenta |
| PTGER3 | prostaglandin E receptor 3 (subtype EP3) | Fetal brain |
| RHCE | Rh blood group, CcEe antigens | BM-CD71+Early erythroid |
| SATB2 | SATB homeobox 2 | Fetal brain |
| SERPINA7 | serpin peptidase inhibitor, clade A (alpha-1 antiproteinase, antitrypsin), member 7 | Cervix |
| SLC4A1 | solute carrier family 4, anion exchanger, member 1 (erythrocyte membrane protein band 3, Diego blood group) | BM-CD71+Early erythroid |
| SLITRK3 | SLIT and NTRK-like family, member 3 | Placenta |
| VGLL1 | vestigial like 1 (Drosophila) | Placenta |
| ZNF238 | zinc finger protein 238 | Fetal brain |

Example of raw qPCR data for fetal brain transcript ZNF238 obtained from subject sample P53 shows the changes across the three trimesters & post-partum.

Example of raw qPCR data for fetal brain transcript ZNF238 obtained from subject sample P53 shows the melting curve of the same experiments of 9A.

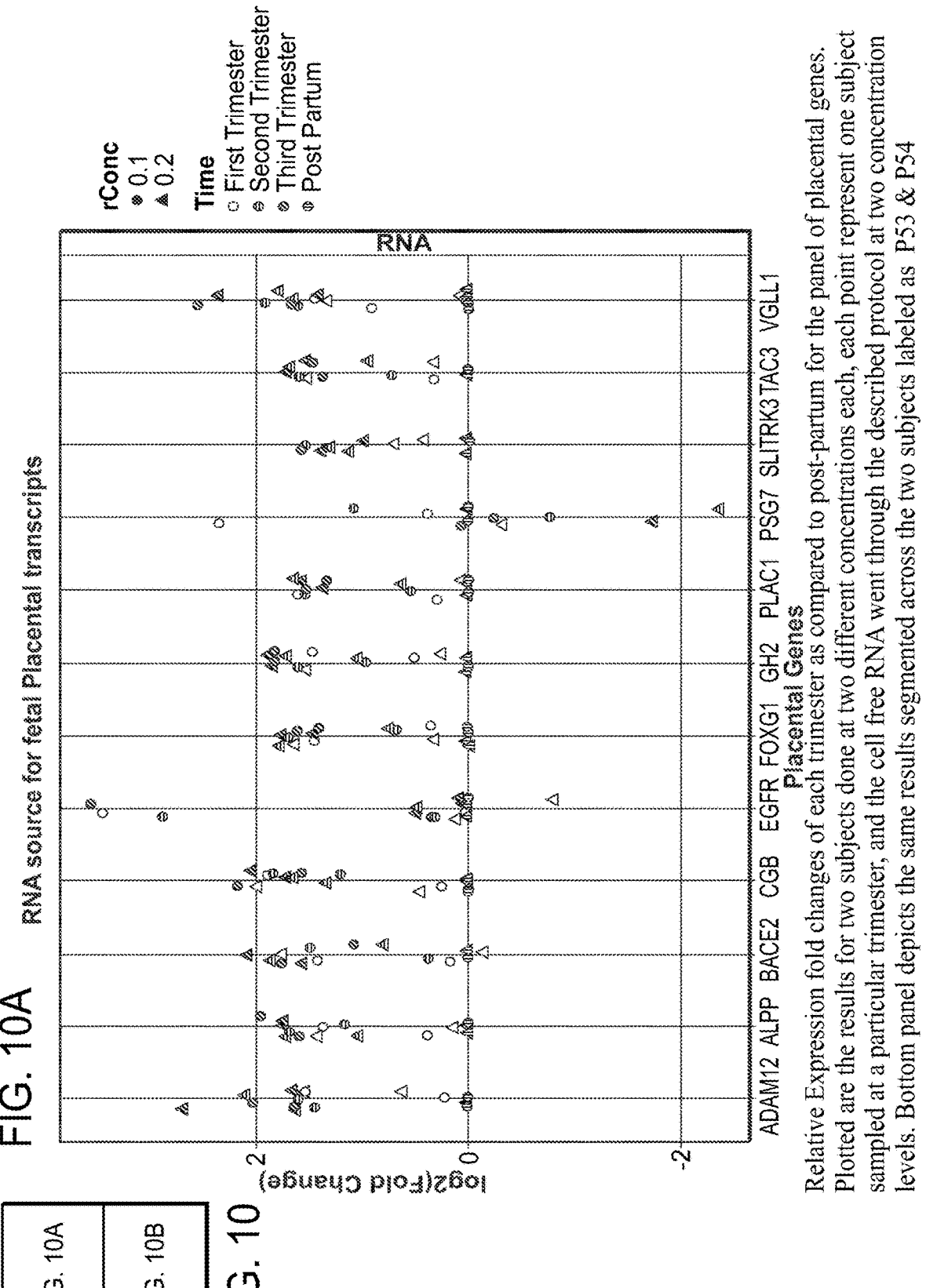

FIG. 10A        RNA source for fetal Placental transcripts

FIG. 10
FIG. 10A
FIG. 10B

Relative Expression fold changes of each trimester as compared to post-partum for the panel of placental genes. Plotted are the results for two subjects done at two different concentrations each, each point represent one subject sampled at a particular trimester, and the cell free RNA went through the described protocol at two concentration levels. Bottom panel depicts the same results segmented across the two subjects labeled as P53 & P54

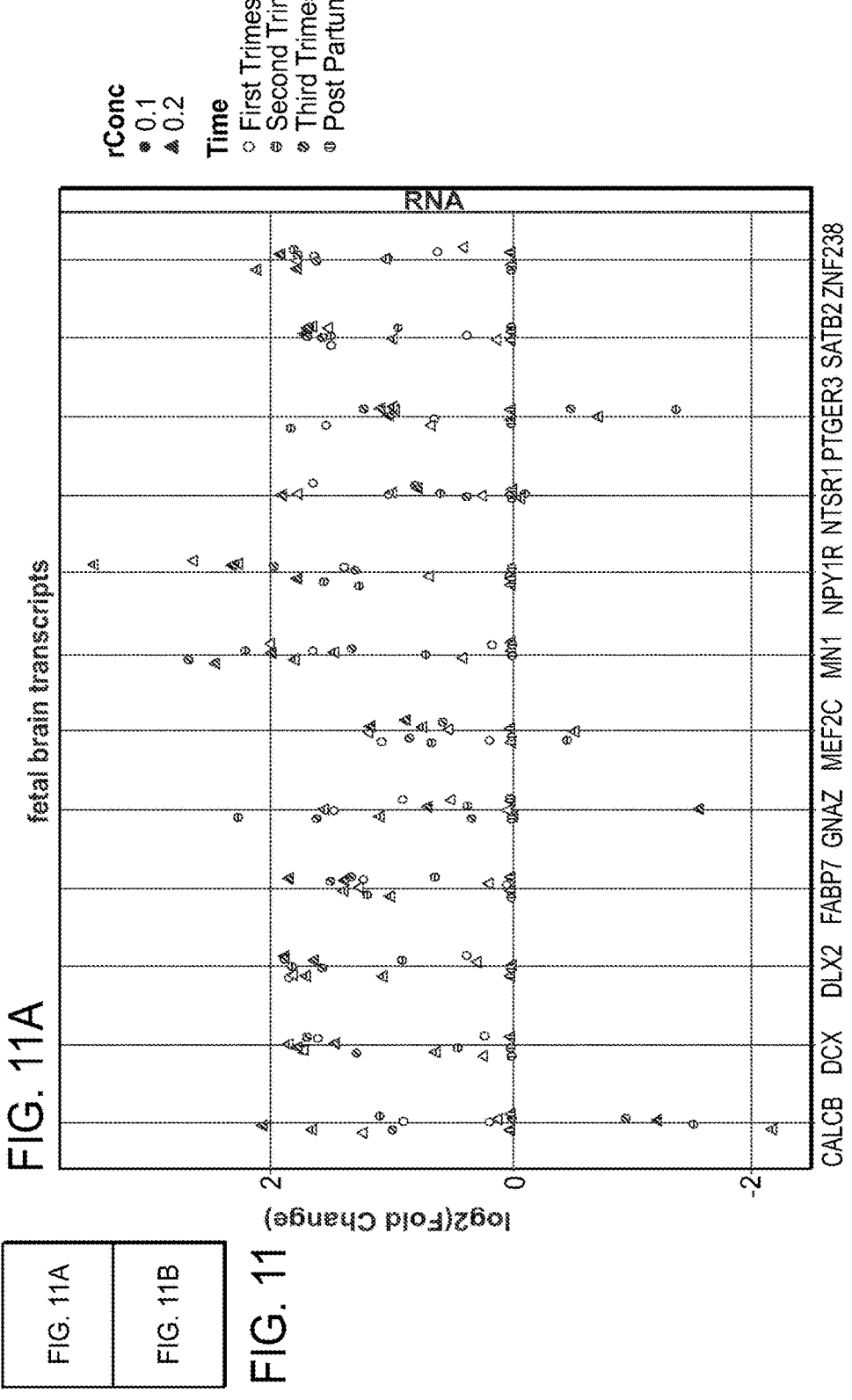

| FIG. 11A |
| FIG. 11B |

Relative Expression fold changes of each trimester as compared to post-partum for the panel of Fetal Brain genes. Plotted are the results for two subjects done at two different concentrations each, each point represent one subject sampled at a particular trimester, and the cell free RNA went through the described protocol at two concentration levels. Bottom panel depicts the same results segmented across the two subjects labeled as P53 & P54.

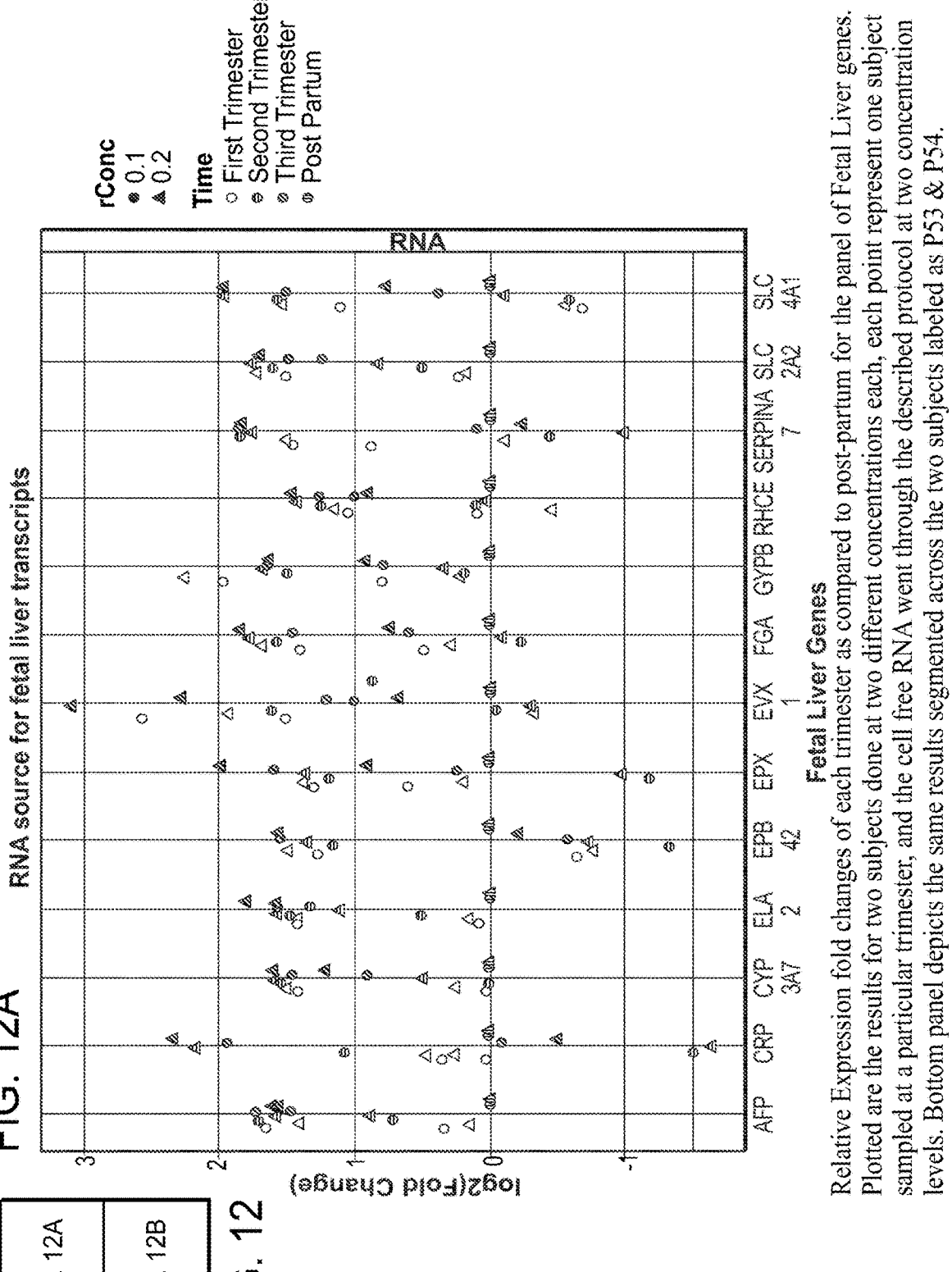

FIG. 12A

RNA source for fetal liver transcripts

Relative Expression fold changes of each trimester as compared to post-partum for the panel of Fetal Liver genes. Plotted are the results for two subjects done at two different concentrations each, each point represent one subject sampled at a particular trimester, and the cell free RNA went through the described protocol at two concentration levels. Bottom panel depicts the same results segmented across the two subjects labeled as P53 & P54.

FIG. 12B
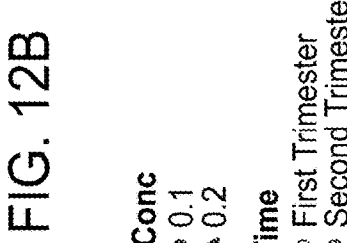
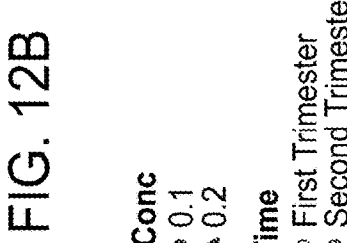

| Donors | Whole Blood (%) | Bone marrow (%) | Hypothalamus (%) | Smooth Muscle (%) | Lung (%) | Thymus (%) | Lymph node (%) | Thyroid (%) |
|---|---|---|---|---|---|---|---|---|
| d1 | 38.13 | 22.94 | 7.73 | 6.70 | 6.27 | 3.56 | 12.67 | 2.00 |
| d2 | 42.64 | 13.88 | 6.10 | 7.40 | 6.14 | 2.85 | 18.06 | 2.93 |
| d3 | 47.61 | 10.16 | 7.87 | 7.43 | 3.07 | 4.68 | 16.18 | 2.99 |
| d4 | 43.64 | 14.30 | 4.86 | 6.38 | 6.70 | 4.06 | 16.33 | 3.73 |

Figure 13. Relative Composition of different organs contribution towards plasma cell free transcriptome

| Donors | hypothalamus (%) | spleen (%) |
|---|---|---|
| d1 | 64.85 | 35.15 |
| d2 | 63.13 | 36.87 |
| d3 | 64.56 | 35.44 |
| d4 | 65.29 | 34.71 |

Figure 14. Decomposition of Organ contribution towards cell free transcriptome using RNA-seq data Heatmap of Delta Ct values as compared to ACTB showing the presence of tissue specific transcripts in Cell-free RNA identified by qPCR Detecting a Sample
Level of RNA in a
Biological Sample Comparing the
Sample Level of RNA
to a Reference Level
of RNA Determining
Whether a Difference
Exists Between the
Sample Level and the
Reference Level Characterizing the
Tissue as Abnormal
if a Difference is
Detected

FIG. 16

Experimental Design

Time Course plasma sample:

1st, 2nd, 3rd Trimester & Post Partum

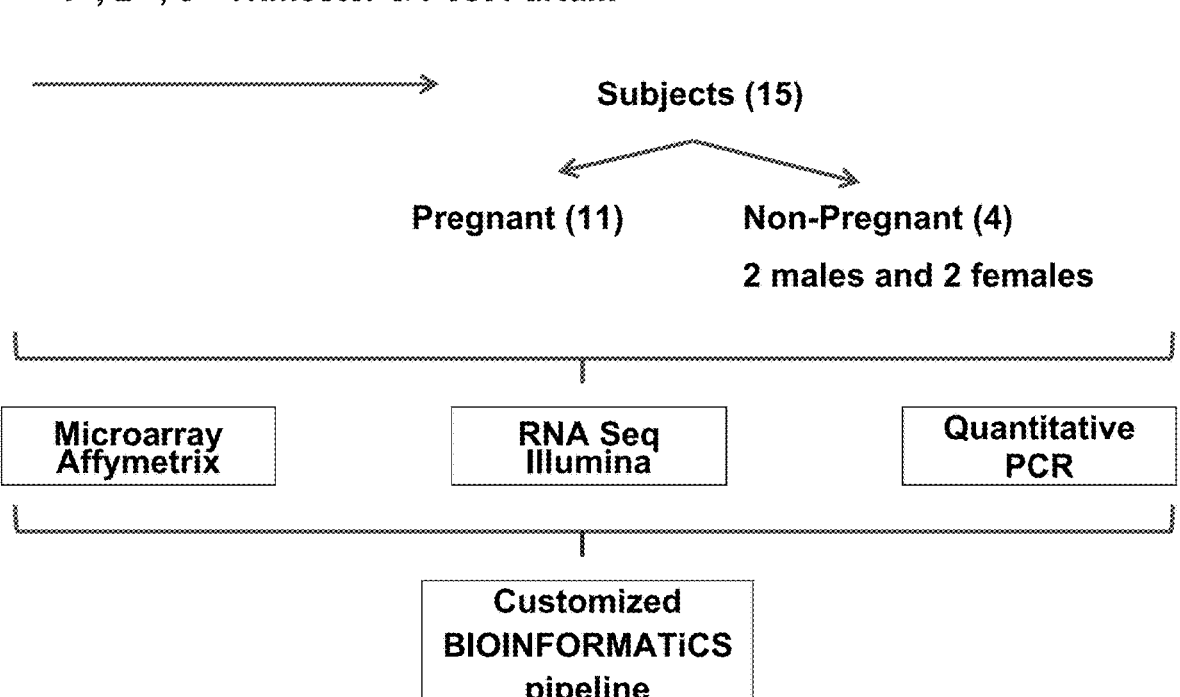

Subjects (15)

Pregnant (11)    Non-Pregnant (4)

2 males and 2 females

| Microarray Affymetrix | RNA Seq Illumina | Quantitative PCR |

Customized BIOINFORMATiCS pipeline

4 pregnant women and 4 non-pregnant control subjects were recruited. For all the pregnant patients, blood was drawn at 1st, 2nd, 3rd Trimester and postpartum. The cell-free plasma RNA were then extracted, amplified and characterized by Affymetrix microarray, Illumina Sequencer and quantitative PCR.

FIG. 18

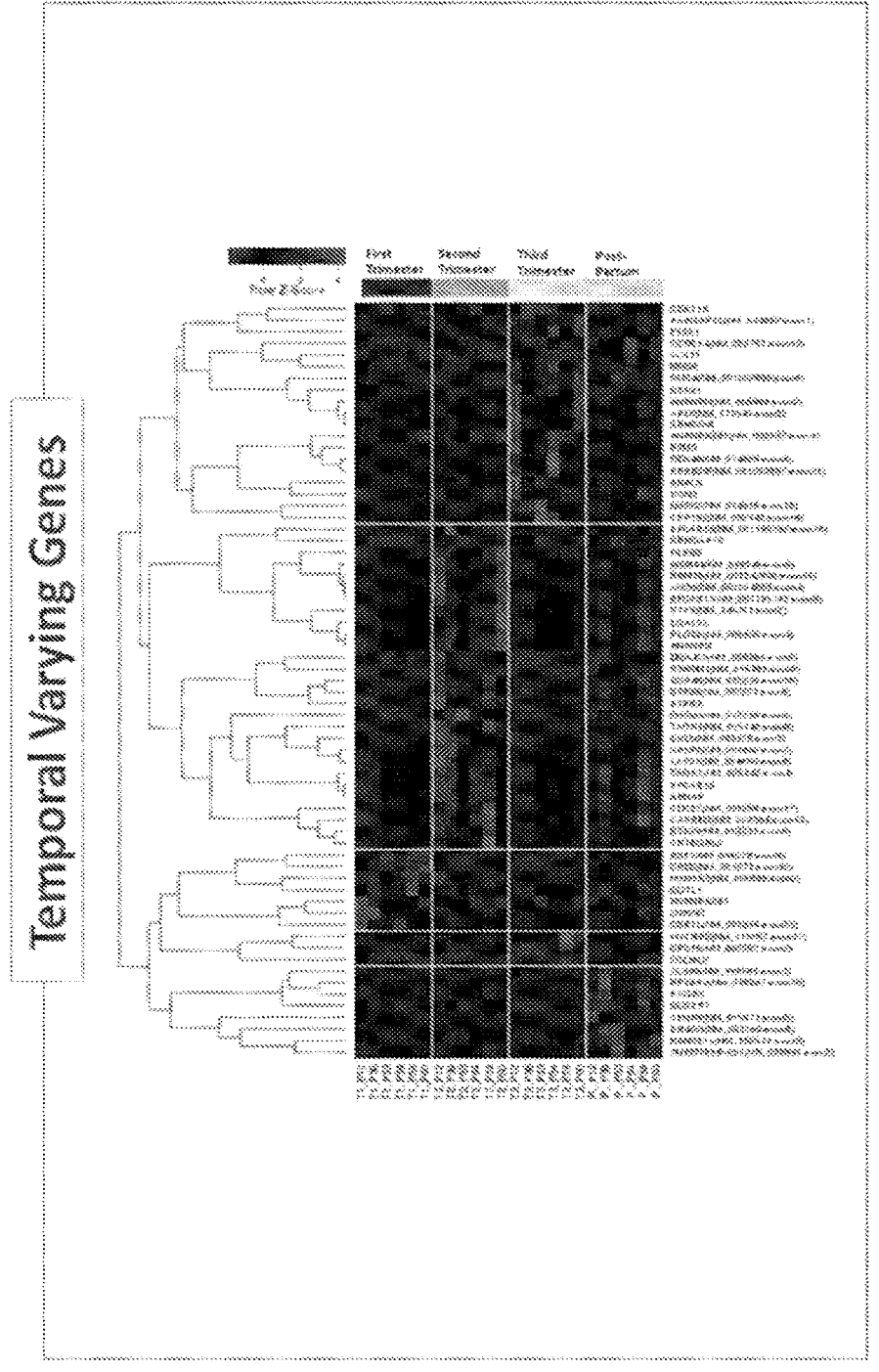

Temporal Varying Genes

Heatmap of Time varying genes identified from microarray analysis. . Unsupervised clustering was performed on genes across different time points. Cluster of genes belongs to the CGB family of genes which are known to be expressed at high levels during the first trimester exhibited corresponding high levels of RNA in the first trimester.

FIG. 20

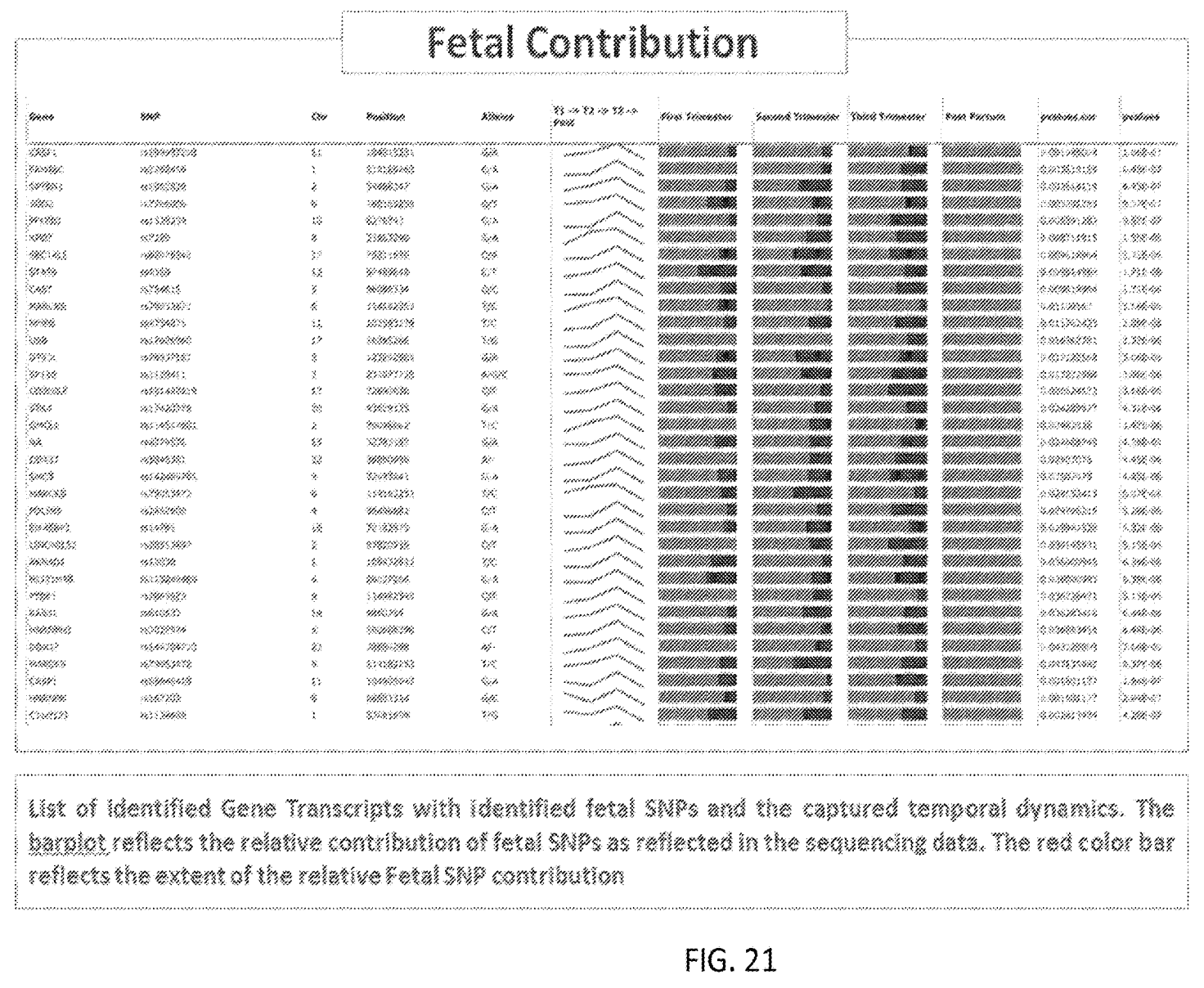

Fetal Contribution

List of Identified Gene Transcripts with identified fetal SNPs and the captured temporal dynamics. The barplot reflects the relative contribution of fetal SNPs as reflected in the sequencing data. The red color bar reflects the extent of the relative Fetal SNP contribution

FIG. 21

Placental Specific Transcripts

Time Course of Placental Specific Genes, measured by qPCR. Plot showing the Delta Ct value with respect to the housekeeping gene ACTB across the different trimesters of pregnancy including after birth. General trends show elevated levels during the trimesters with a decline to low levels after the baby is born.

Fetal Brain Specific Transcripts

Time Course of Fetal Brain Specific Genes, measured by qPCR. Plot showing the Delta Ct value with respect to the housekeeping gene ACTB across the different trimesters of pregnancy including after birth. General trends show elevated levels during the trimesters with a decline to low levels after the baby is born.

Fetal Liver Specific Transcripts

*Time Course of Fetal Liver Specific Genes, measured by qPCR. Plot showing the Delta Ct value with respect to the housekeeping gene ACTB across the different trimesters of pregnancy including after birth. General trends show elevated levels during the trimesters with a decline to low levels after the baby is born.*

Tissue Composition

CONSIDER: observed cell free transcriptome in typical adult plasma as a summation of RNAs from different tissue types $$Y = \sum \pi_i X_i + \varepsilon$$

Y -> observed cell free transcriptome in maternal plasma
X -> Transcriptome in Tissue i
$\pi$ -> Fractional contribution of Tissue i to observed cell free transcriptome where $\sum \pi_i = 1$ & $\pi \geq 0$
$\varepsilon$ -> normally distributed error

FIG. 25

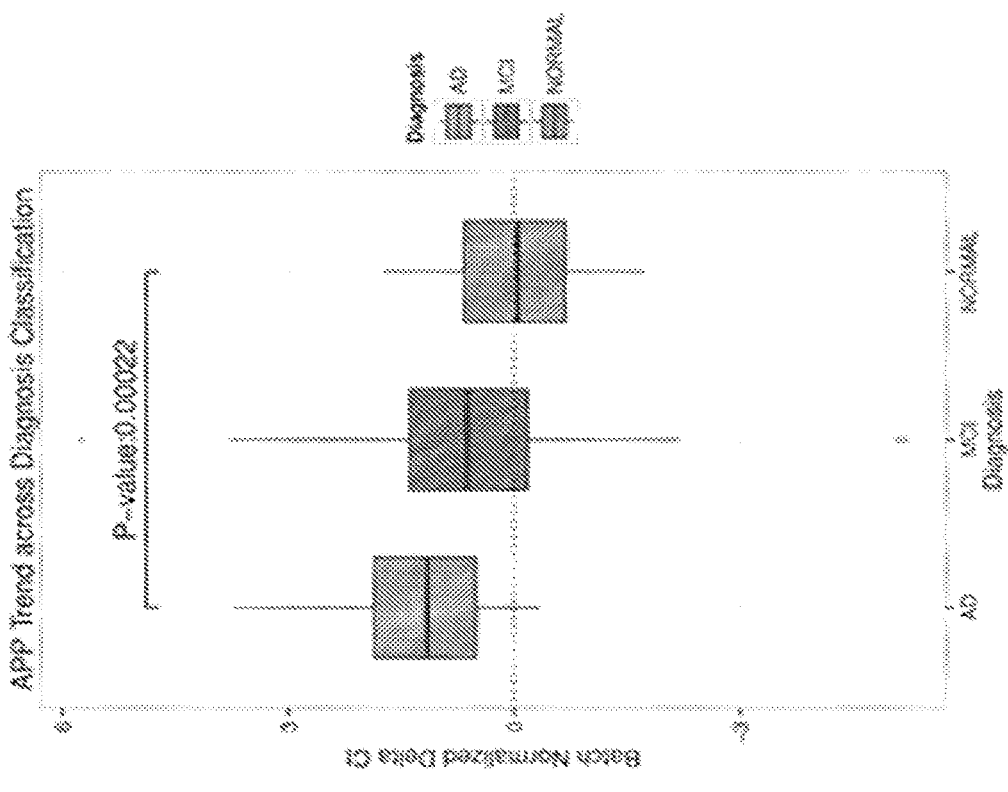
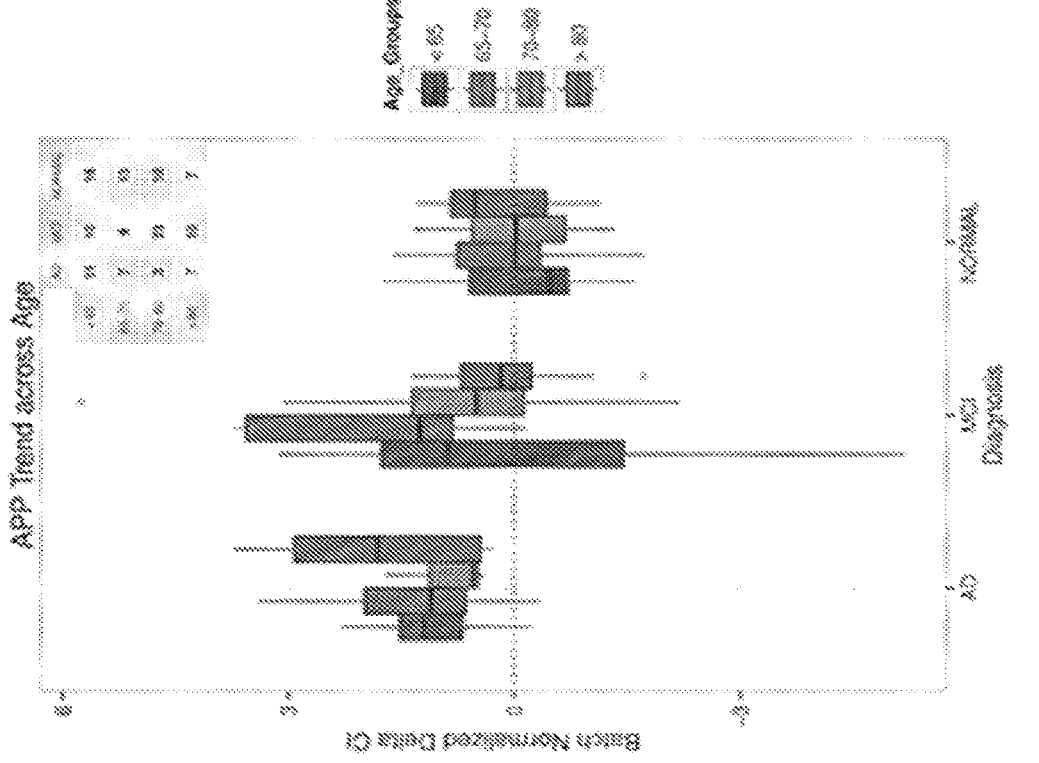
FIG. 28

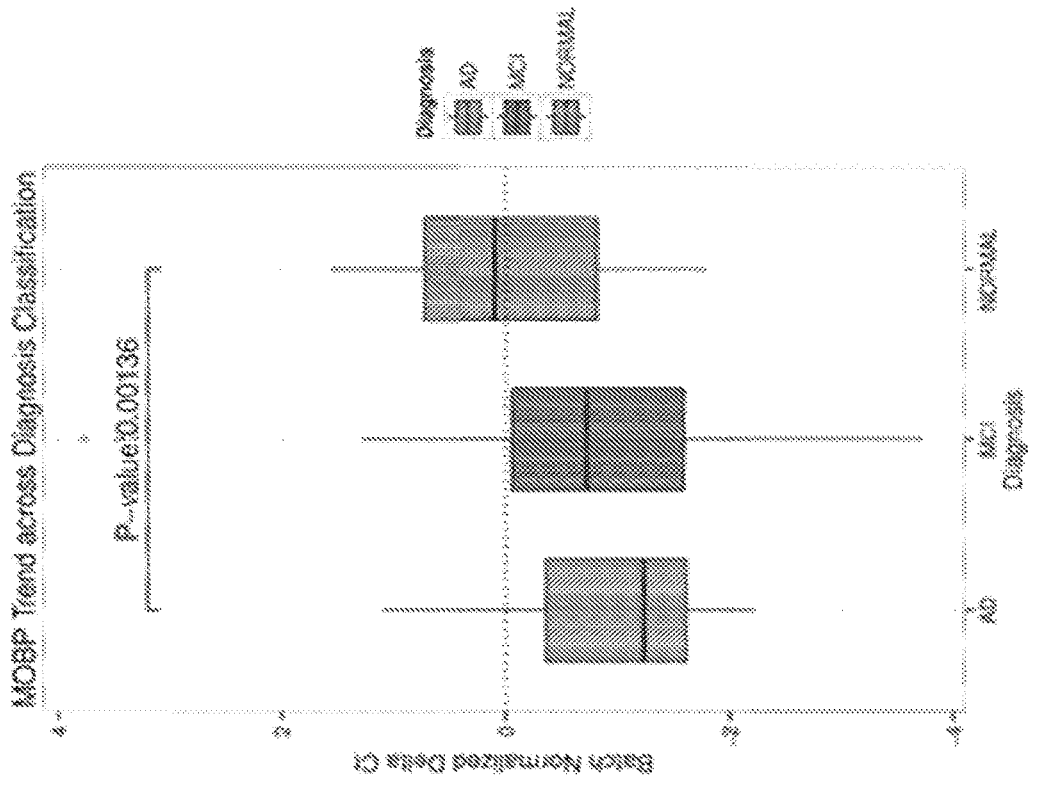
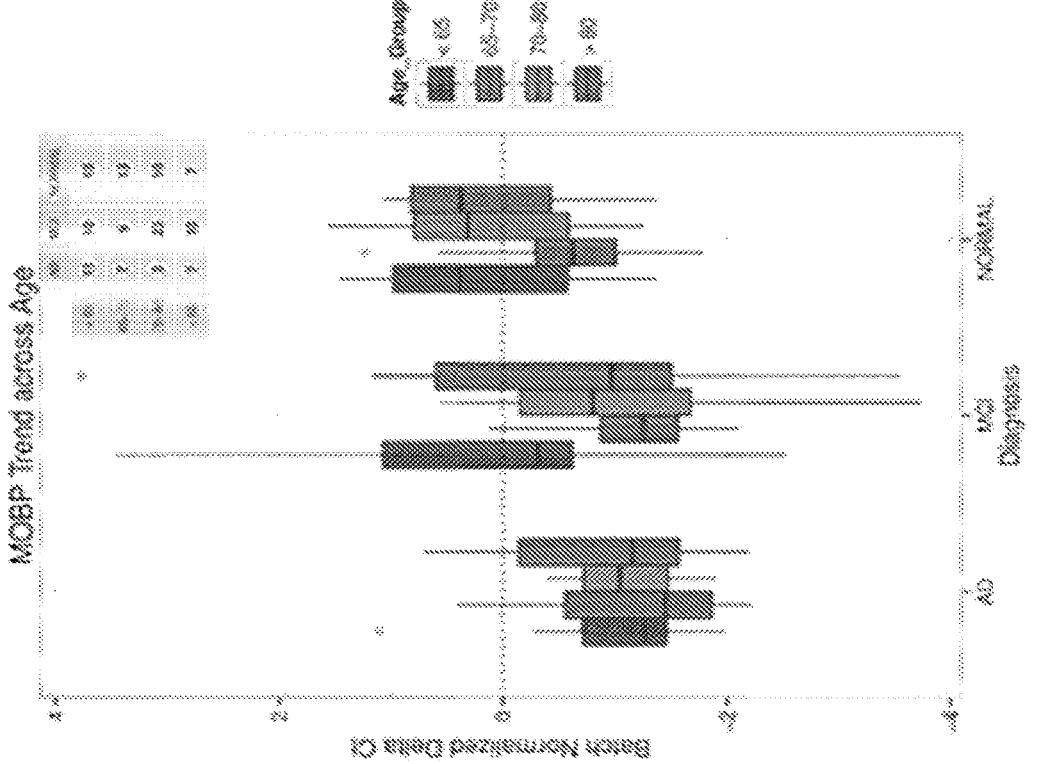
FIG. 29

AUC: 0.794

METHODS FOR SEQUENCING CELL-FREE RNA

CROSS REFERENCE

This application is a Continuation and claims the benefit of U.S. application Ser. No. 16/836,498, filed Mar. 31, 2020, which is a Continuation and claims the benefit of U.S. application Ser. No. 15/034,746, filed May 5, 2016, now abandoned, which is a Continuation and claims the benefit of U.S Application No. PCT/US2014/064355, filed Nov. 6, 2014, and priority to U.S. Provisional No. 61/900,927, filed Nov. 6, 2013, and is a continuation-in-part of U.S. Non-Provisional Ser. No. 13/752,131, filed Jan. 28, 2013, now abandoned, which claims the benefit of and priority to U.S. Provisional No. 61/591,642, filed on Jan. 27, 2012. The entirety of each foregoing application is incorporated herein by reference.

TECHNICAL FIELD

The present invention relates to assessing neurological disorders based on nucleic acid specific to brain tissue.

BACKGROUND

Dementia is a catchall term used to characterize cognitive declines that interfere with one's ability to perform everyday activities. Signs of dementia include declines in the following mental functions: memory, communication and language, ability to focus and pay attention, reasoning, judgment, motor skills, and visual perception. While there are several neurological disorders that cause dementia, Alzheimer's disease is the most common, accounting for 60 to 80 percent of all dementia cases.

Alzheimer's disease is a progressive disease that gradually destroys memory and mental functions in patients. Symptoms manifest initially as a decline in memory followed by deterioration of other cognitive functions as well as by abnormal behavior. Individuals with Alzheimer's disease usually begin to show dementia symptoms later in life (e.g., 65 years or older), but a small percentage of individuals in their 40s and 50s experience early onset Alzheimer's disease. Alzheimer's disease is associated with the damage and degeneration of neurons in several regions of the brain. The neuropathic characteristics of Alzheimer's disease include the presence of plaques and tangles, synaptic loss, and selective neuronal cell death. Plaques are abnormal levels of protein fragments called beta-amyloid that accumulate between nerve cells. Tangles are twisted fibers of a protein known as tau that accumulate within nerve cells.

While the above-described neuropathic characteristics are hallmarks of the disease, the exact cause of Alzheimer's disease is unknown and there are no specific tests that confirm whether an individual has Alzheimer's disease. For diagnosis of Alzheimer's, clinicians assess a combination of clinical criteria, which may include a neurological exam, mental status tests, and brain imaging. Efforts are being made to determine the genetic causes in order to help definitively diagnose Alzheimer's disease. However, only a handful of genetic markers associated with Alzheimer's have been characterized to date, and diagnostic tests for those markers require invasive brain biopsies.

SUMMARY

The present invention provides methods for assessing neurological conditions using circulating nucleic acid (such as DNA or RNA) that is specific to brain tissue. In particular embodiments, the invention involves a comparative analysis of levels of circulating nucleic acid in a patient that are specific to brain tissue with reference levels of circulating nucleic acid that are specific to brain tissue. The present invention recognizes that abnormal deviations in circulating nucleic acid result from tissue-specific nucleic acid being released into the blood in large amounts as tissue begins to fail and degrade. By focusing on genes the expression of which is highly specific to brain tissue, methods of the invention allow one to characterize the extent of brain degradation based on statistically-significant levels of circulating brain-specific transcripts; and use that characterization to diagnose and determine the stage of the neurological disease. Accordingly, methods of the invention allow one to characterize neurological disorders without focusing on small subset of known biomarkers, but rather focusing on the extent to which nucleic acid is released into blood from brain tissue affected by disease. Methods of the invention are particularly useful in diagnosing and determining the stage of Alzheimer's disease.

In particular embodiments, methods of the invention include obtaining RNA from a blood sample of a patient suspected of having a neurological disorder, and determining a level of the sample RNA that originated from brain tissue. In certain embodiments, the RNA is converted to cDNA. The level of the sample RNA specific to brain tissue is then compared to a reference level of RNA that is specific to brain tissue. The reference level may be derived from a subject or patient population having a neurological disorder or from a normal/control subject or patient population. Depending on the reference level chosen, similarities or variances between the level of sample RNA and the reference level of RNA are indicative of the neurological disorder, the type of neurological disorder and/or the stage of the neurological disorder. In certain embodiments, only similarities or variances of statistical significance are indicative of the neurological disorder. Whether a variance is significant depends upon the chosen reference population.

Additional aspects of the invention involve assessing a neurological disorder using a set of predictive variables correlated with a neurological disorder. In such aspects, methods of the invention involve detecting RNA present in a biological sample obtained from a patient suspected of having a neurological disorder. In certain embodiments, the RNA is converted to cDNA. Sample levels of one or more RNA transcripts that are specific to brain tissue are determined, and the sample levels of RNA transcripts specific to brain tissue are compared to a set of predictive variables correlated with a neurological disorder. The predictive variables may include reference levels of RNA transcripts that are specific to brain tissue and correspond to one or more stages of the neurological disorders. In certain embodiments, the predictive variables may include brain-specific reference levels of transcripts that correlate to other factors such as age, sex, environmental exposure, familial history of dementia, dementia symptoms. The stage of a neurological disorder of the patient may be indicated based on variances or similarities between the level of sample RNA and the predictive variables.

RNA obtained from the blood sample may be converted into synthetic cDNA. In such instances, the sample levels of cDNA that correspond to RNA originating from brain tissue may be compared to reference levels of RNA or references levels of DNA that correspond to RNA originating from brain tissue. For example, methods of the invention may include the steps of detecting circulating RNA in a sample obtained from a patient suspected of having a neurological disorder and converting the circulating RNA from the sample into cDNA. The next steps involve determining levels of the sample cDNA that correspond to RNA originating from brain tissue, and comparing the determined levels of the cDNA to a reference level of cDNA. The reference level of cDNA may also correspond to RNA originating from brain tissue. The neurological condition of the patient may then be indicated based similarities or differences between the patient cDNA levels and the reference cDNA levels.

Methods of the invention are also useful to identify one or more biomarkers associated with a neurological disorder. In such aspects, brain-specific transcripts of an individual or patient population suspected of having or actually having a neurological disorder (e.g. exhibiting impaired cognitive functions) are compared to a reference (e.g. brain-specific transcripts of a healthy, normal population). The brain-specific transcripts of the individual or patient population that are differentially expressed as compared to the reference may then be identified as biomarkers of the neurological disorder. In certain embodiments, only differentially expressed brain-specific transcripts that are statistically significant are identified as biomarkers. Methods of determining statistical significance are known in the art.

The reference level of RNA or cDNA specific to brain tissue may pertain to a patient population having a particular condition or pertain to a normal/control patient population. In one embodiment, the reference level of RNA or cDNA specific to brain tissue may be levels of RNA or cDNA specific to brain tissue in a normal patient population. In another embodiment, the reference level of RNA or cDNA may be the level of RNA or cDNA specific to brain tissue in a patient population having a certain neurological disorder. The certain neurological disorder may be mild cognitive impairment or moderate-to-severe cognitive impairment. The various levels of cognitive impairment may be indicative of a stage of Alzheimer's disease. In further embodiments, the reference level of RNA or cDNA may be the level of RNA or cDNA specific to brain tissue having a certain neurological disorder at a certain age. Other embodiments may include reference levels that correspond to a variety of predictive variables, including type of neurological disorder, stage of neurological disorder, age, sex, environmental exposure, familial history of dementia, dementia symptoms.

Methods of the invention involve assaying biological samples for circulating nucleic acid (RNA or DNA). Suitable biological samples may include blood, blood fractions, plasma, saliva, sputum, urine, semen, transvaginal fluid, and cerebrospinal fluid. Preferably, the sample is a blood sample. The blood sample may be plasma or serum.

The present invention also provides methods for profiling the origin of the cell-free RNA to assess the health of an organ or tissue. Deviations in normal cell-free transcriptomes are caused when organ/tissue-specific transcripts are released in to the blood in large amounts as those organs/tissue begin to fail or are attacked by the immune system or pathogens. As a result inflammation process can occur as part of body's complex biological response to these harmful stimuli. The invention, according to certain aspects, utilizes tissue-specific RNA transcripts of healthy individuals to deduce the relative optimal contributions of different tissues in the normal cell-free transcriptome, with each tissue-specific RNA transcript of the sample being indicative of the apotopic rate of that tissue. The normal cell-free transcriptome serves as a baseline or reference level to assess tissue health of other individuals. The invention includes a comparative measurement of the cell-free transcriptome of a sample to the normal cell free transcriptome to assess the sample levels of tissue-specific transcripts circulating in plasma and to assess the health of tissues contributing to the cell-free transcriptome.

In addition to cell-free transcriptomes reference levels of normal patient populations, methods of the invention also utilize reference levels for cell-free transcriptomes specific to other patient populations. Using methods of the invention one can determine the relative contribution of tissue-specific transcripts to the cell-free transcriptome of maternal subjects, fetus subjects, and/or subjects having a condition or disease.

By analyzing the health of tissue based on tissue-specific transcripts, methods of the invention advantageously allow one to assess the health of a tissue without relying on disease-related protein biomarkers. In certain aspects, methods of the invention assess the health of a tissue by comparing a sample level of RNA in a biological sample to a reference level of RNA specific to a tissue, determining whether a difference exists between the sample level and the reference level, and characterizing the tissue as abnormal if a difference is detected. For example, if a patient's RNA expression levels for a specific tissue differs from the RNA expression levels for the specific tissue in the normal cell-free transcriptome, this indicates that patient's tissue is not functioning properly.

In certain aspects, methods of the invention involve assessing health of a tissue by characterizing the tissue as abnormal if a specified level of RNA is present in the blood. The method may further include detecting a level of RNA in a blood sample, comparing the sample level of RNA to a reference level of RNA specific to a tissue, determining whether a difference exists between the sample level and the reference level, and characterizing the tissue as abnormal if the sample level and the reference level are the same.

The present invention also provides methods for comprehensively profiling fetal specific cell-free RNA in maternal plasma and deconvoluting the cell-free transcriptome of fetal origin with relative proportion to different fetal tissue types. Methods of the invention involve the use of next-generation sequencing technology and/or microarrays to characterize the cell-free RNA transcripts that are present in maternal plasma at different stages of pregnancy. Quantification of these transcripts allows one to deduce changes of these genes across different trimesters, and hence provides a way of quantification of temporal changes in transcripts.

Methods of the invention allow diagnosis and identification of the potential for complications during or after pregnancy. Methods also allow the identification of pregnancy-associated transcripts which, in turn, elucidates maternal and fetal developmental programs. Methods of the invention are useful for preterm diagnosis as well as elucidation of transcript profiles associated with fetal developmental pathways generally. Thus, methods of the invention are useful to characterize fetal development and are not limited to characterization only of disease states or complications associated with pregnancy. Exemplary embodiments of the methods are described in the detailed description, claims, and figures provided below.

BRIEF DESCRIPTION OF THE DRAWINGS

FIG. 4 depicts a ranking of the top 20 transcripts differentially expressed between pre-term and normal pregnancy.

FIG. 5 depicts results of a Gene Ontology analysis on the top 20 common RNA transcripts of FIG. 4, showing those transcripts enriched for proteins that are attached (integrated or loosely bound) to the plasma membrane or on the membranes of the platelets.

FIG. 6 depicts that the gene expression profile for PVALB across the different trimesters shows the premature births [highlighted in blue] has higher levels of cell free RNA transcripts found as compared to normal pregnancy.

FIG. 7 outlines exemplary process steps for determining the relative tissue contributions to a cell-free transcriptome of a sample. FIG. 7 is split across FIGS. 7A and 7B, as indicated by the graphical figure outline.

FIG. 8 depicts the panel of selected fetal tissue-specific transcripts generated in Example 2. FIG. 8 is split across FIGS. 8A and 8B, as indicated by the graphical figure outline.

FIG. 10 illustrates relative expression of placental genes across maternal time points (first trimester, second trimester, third trimester, and post partum). FIG. 10 is split across FIGS. 10A and 10B, as indicated by the graphical figure outline. In FIG. 10, relative expression fold changes of each trimester as compared to post-partum for the panel of placental genes. Plotted are the results for two subjects done at two different concentrations each, each point represent one subject sampled at a particular trimester, and the cell free RNA went through the described protocol at two concentration levels.

FIG. 11 illustrates relative expression of fetal brain genes across maternal time points (first trimester, second trimester, third trimester, and post partum), FIG. 11 is split across FIGS. 11A and 11B, as indicated by the graphical figure outline. In FIG. 11A, relative expression folds changes of each trimester as compared to post-partum for the panel of Fetal Brain genes. Plotted are the results for two subjects done at two different concentrations each, each point represent one subject sampled at a particular trimester, and the cell free RNA went through the described protocol at two concentration levels.

FIG. 12 illustrates relative expression of fetal liver genes across maternal time points (first trimester, second trimester, third trimester, and post partum). FIG. 12 is split across FIGS. 12A and 12B, as indicated by the graphical figure outline. In FIG. 12A, relative expression fold changes of each trimester as compared to post-partum for the panel of Fetal Liver genes. Plotted are the results for two subjects done at two different concentrations each, each point represent one subject sampled at a particular trimester, and the cell free RNA went through the described protocol at two concentration levels. FIG. 12B depicts the same results segmented across the two subjects labeled as P53 & P54.

FIG. 13 illustrates the relative composition of different organs contribution towards a plasma adult cell free transcriptome.

FIG. 14 illustrates a decomposition of decomposition of organ contribution towards a plasma adult cell free transcriptome using RNA-seq data.

FIG. 16 depicts a flow-diagram of a method of the invention according to certain embodiments.

FIG. 18 illustrates an experimental design comparing microarray, RNA-seq and quantitative PCR for a customized bioinformatics pipeline. In the experiment, 11 pregnant women and 4 non-pregnant control subjects were recruited. For all the pregnant patients, blood was drawn at 1st, 2nd, 3rd trimester and postpartum. The cell-free plasma RNA were then extracted, amplified and characterized by Affymetrix microarray, Illumina sequencer and quantitative PCR.

FIG. 20 illustrates another heat map of temporal varying genes obtained from microarray analysis. Unsupervised clustering was performed on genes across different time points. Cluster of genes belongs to the CGB family of genes which are known to be expressed at high levels during the first trimester exhibited corresponding high levels of RNA in the first trimester.

FIG. 21 illustrates a list of genes identified with fetal SNPs using the experimental design of FIG. 18. List of identified Gene Transcripts with identified fetal SNPs and the captured temporal dynamics. The barplot reflects the relative contribution of fetal SNPs as reflected in the sequencing data. The red color bar reflects the extent of the relative Fetal SNP contribution.

As shown in FIG. 22, the time course of placental specific genes is measured by qPCR. Plot showing the Delta Ct value with respect to the housekeeping gene ACTB across the different trimesters of pregnancy including after birth. General trends show elevated levels during the trimesters with a decline to low levels after the baby is born.

As shown in FIG. 23, the time course of fetal brain specific genes is measured by qPCR. Plot showing the Delta Ct value with respect to the housekeeping gene ACTB across the different trimesters of pregnancy including after birth. General trends show elevated levels during the trimesters with a decline to low levels after the baby is born.

As shown in FIG. 24, the time course of fetal liver specific genes is measured by qPCR. Plot showing the Delta Ct value with respect to the housekeeping gene ACTB across the different trimesters of pregnancy including after birth. General trends show elevated levels during the trimesters with a decline to low levels after the baby is born.

FIG. 25 illustrates tissue composition of the adult cell free transcriptome in typical adult plasma as a summation of RNAs from different tissue types.

FIG. 28 depicts the measured APP levels in patients. The left panel shows the levels of APP transcripts across different age groups in the study. The right panel shows the different levels of the APP transcripts of the combined population of patients.

FIG. 29 depicts the measured MOBP levels in patients. The left panel shows the levels of the MOBP transcripts across different age groups in the study. The right panel shows the different levels of the MOBP transcripts of the combined population of patients.

DETAILED DESCRIPTION

Figure 2:
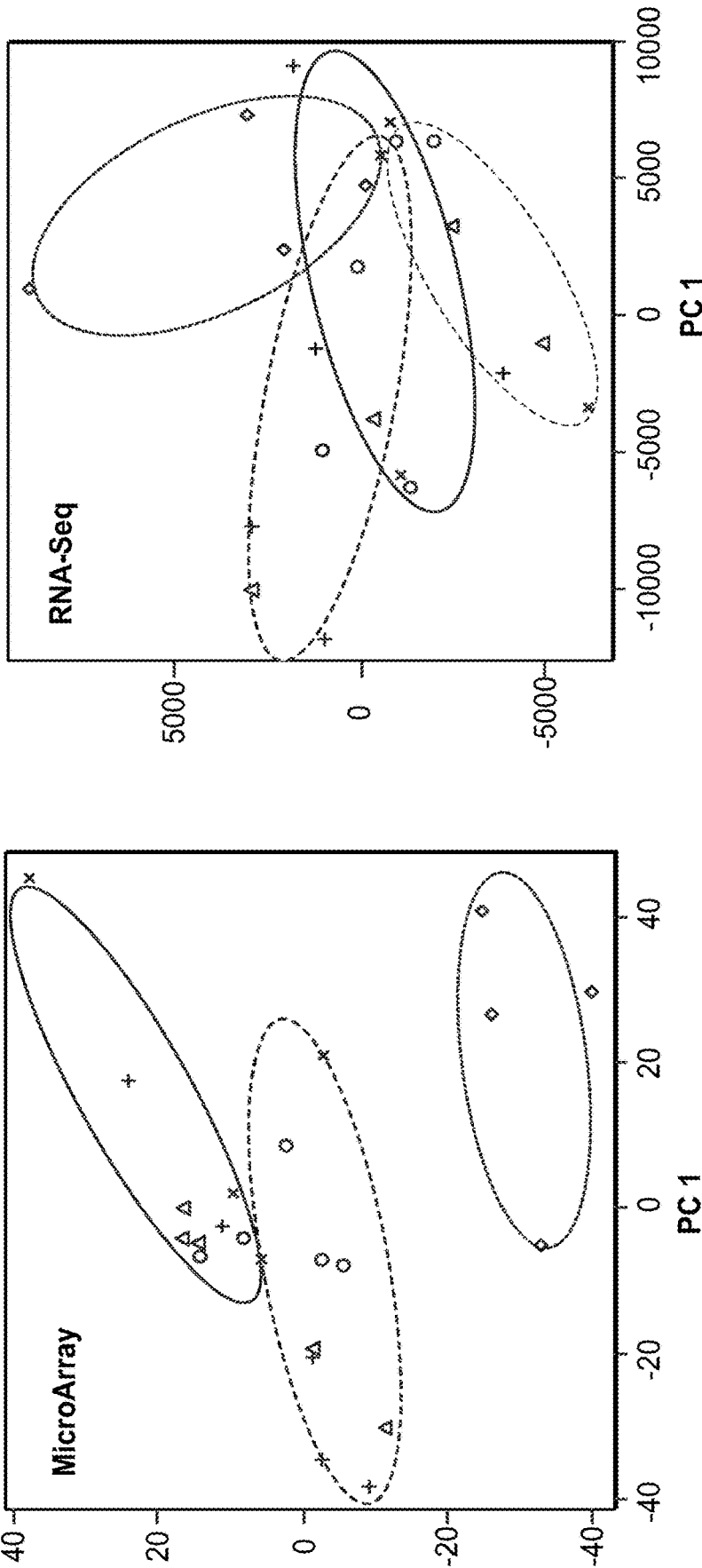
FIG. 2 shows plots of the two main principal components for cell free RNA transcript levels obtained in Example 1.

Methods and materials described herein apply a combination of next-generation sequencing and microarray techniques for detecting, quantitating and characterizing RNA present in a biological sample. In certain embodiments, the biological sample contains a mixture of genetic material from different genomic sources, i.e. pregnant female and a fetus.

Unlike other methods of digital analysis in which the nucleic acid in the sample is isolated to a nominal single target molecule in a small reaction volume, methods of the present invention are conducted without diluting or distributing the genetic material in the sample. Methods of the invention allow for simultaneous screening of multiple transcriptomes, and provide informative sequence information for each transcript at the single-nucleotide level, thus providing the capability for non-invasive, high throughput screening for a broad spectrum of diseases or conditions in a subject from a limited amount of biological sample.

In one particular embodiment, methods of the invention involve analysis of mixed fetal and maternal RNA in the maternal blood to identify differentially expressed transcripts throughout different stages of pregnancy that may be indicative of a preterm or pathological pregnancy. Differential detection of transcripts is achieved, in part, by isolating and amplifying plasma RNA from the maternal blood throughout the different stages of pregnancy, and quantitating and characterizing the isolated transcripts via microarray and RNA-Seq.

Methods and materials specific for analyzing a biological sample containing RNA (including non-maternal, maternal, maternal-fetus mixed) as described herein, are merely one example of how methods of the invention can be applied and are not intended to limit the invention. Methods of the invention are also useful to screen for the differential expression of target genes related to cancer diagnosis, progression and/or prognosis using cell-free RNA in blood, stool, sputum, urine, transvaginal fluid, breast nipple aspirate, cerebrospinal fluid, etc.

In certain embodiments, methods of the invention generally include the following steps: obtaining a biological sample containing genetic material from different genomic sources, isolating total RNA from the biological sample containing biological sample containing a mixture of genetic material from different genomic sources, preparing amplified cDNA from total RNA, sequencing amplified cDNA, and digital counting and analysis, and profiling the amplified cDNA.

Figure 16:
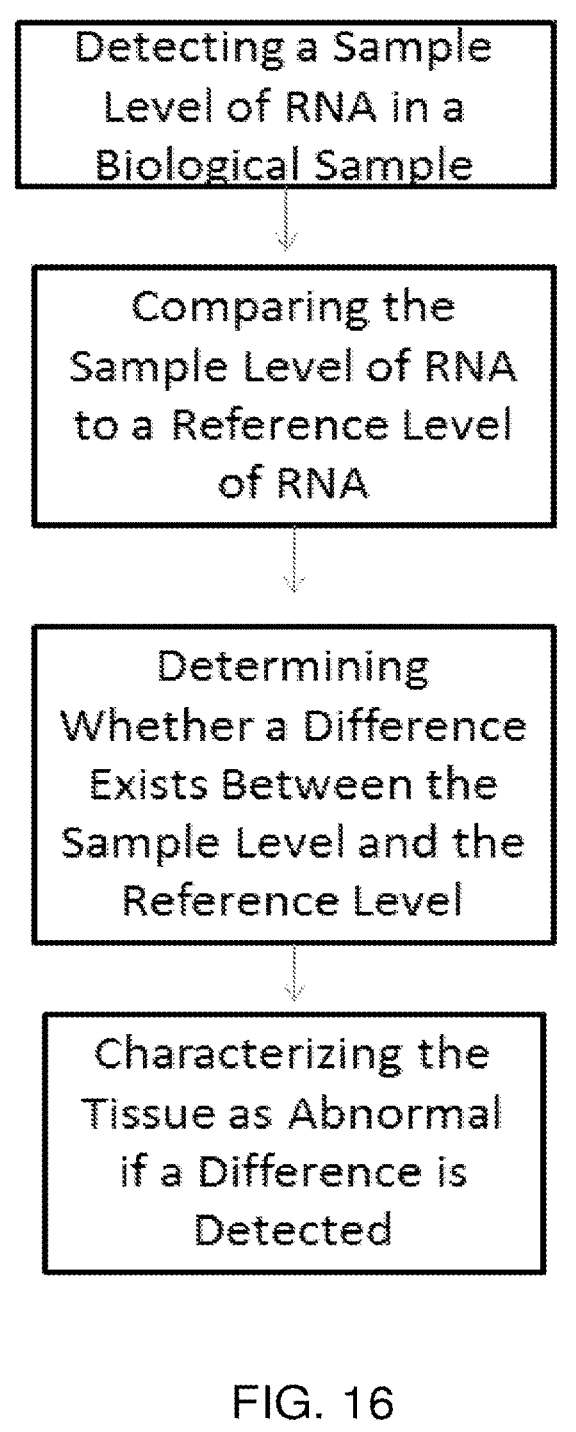

Methods of the invention also involve assessing the health of a tissue contributing to the cell-free transcriptome. In certain embodiments, the invention involves assessing the cell-free transcriptome of a biological sample to determine tissue-specific contributions of individual tissues to the cell-free transcriptome. According to certain aspects, the invention assesses the health of a tissue by detecting a sample level of RNA in a biological sample, comparing the sample level of RNA to a reference level of RNA specific to the tissue, and characterizing the tissue as abnormal if a difference is detected. This method is applicable to characterize the health of a tissue in non-maternal subjects, pregnant subjects, and live fetuses. FIG. 16 depicts a flow-diagram of this method according to certain embodiments.

In certain aspects, methods of the invention employ a deconvolution of a reference cell-free RNA transcriptome to determine a reference level for a tissue. Preferably, the reference cell-free RNA transcriptome is a normal, healthy transcriptome, and the reference level of a tissue is a relative level of RNA specific to the tissue present in the blood of healthy, normal individuals. Methods of the invention assume that apoptotic cells from different tissue types release their RNA into plasma of a subject. Each of these tissues expresses a specific number of genes unique to the tissue type, and the cell-free RNA transcriptome of a subject is a summation of the different tissue types. Each tissue may express one or more numbers of genes. In certain embodiments, the reference level is a level associated with one of the genes expressed by a certain tissue. In other embodiments, the reference level is a level associated with a plurality of genes expressed by a certain tissue. It should be noted that a reference level or threshold amount for a tissue-specific transcript present in circulating RNA may be zero or a positive number.

For healthy, normal subjects, the relative contributions of circulating RNA from different tissue types are relatively stable, and each tissue-specific RNA transcript of the cell-free RNA transcriptome for normal subjects can serve as a reference level for that tissue. Applying methods of the invention, a tissue is characterized as unhealthy or abnormal if a sample includes a level of RNA that differs from a reference level of RNA specific to the tissue. The tissue of the sample may be characterized as unhealthy if the actual level of RNA is statistically different from the reference level. Statistical significance can be determined by any method known in the art. These measurements can be used to screen for organ health, as diagnostic tool, and as a tool to measure response to pharmaceuticals or in clinical trials to monitor health.

If a difference is detected between the sample level of RNA and the reference level of RNA, such difference suggests that the associated tissue is not functioning properly. The change in circulating RNA may be the precursor to organ failure or indicate that the tissue is being attacked by the immune system or pathogens. If a tissue is identified as abnormal, the next step(s), according to certain embodiments, may include more extensive testing of the tissue (e.g. invasive biopsy of the tissue), prescribing course of treatment specific to the tissue, and/or routine monitoring of the tissue.

Methods of the invention can be used to infer organ health non-invasively. This non-invasive testing can be used to screen for appendicitis, incipient diabetes and pathological conditions induced by diabetes such as nephropathy, neuropathy, retinopathy etc. In addition, the invention can be used to determine the presence of graft versus host disease in organ transplants, particularly in bone marrow transplant recipients whose new immune system is attacking the skin, GI tract or liver. The invention can also be used to monitor the health of solid organ transplant recipients such as heart, lung and kidney. The methods of the invention can assess likelihood of prematurity, preeclampsia and anomalies in pregnancy and fetal development. In addition, methods of the invention could be used to identify and monitor neurological disorders (e.g. multiple sclerosis and Alzheimer's disease) that involve cell specific death (e.g. of neurons or due to demyelination) or that involve the generation of plaques or protein aggregation.

A cell-free transcriptome for purposes of determining a reference level for tissue-specific transcripts can be the cell-free transcriptome of one or more normal subjects, maternal subjects, subjects having a certain conditions and diseases, or fetus subjects. In the case of certain conditions, the reference level of a tissue is a level of RNA specific to the tissue present in blood of one or more subjects having a certain disease or condition. In such aspect, the method includes detecting a level of RNA in a blood, comparing the sample level of RNA to a reference level of RNA specific to a tissue, determining whether a difference exists between the sample level and the reference level, and characterizing the as abnormal if the sample level and the reference level are the same.

A deconvolution of a cell-free transcriptome is used to determine the relative contribution of each tissue type towards the cell-free RNA transcriptome. The following steps are employed to determine the relative RNA contributions of certain tissues in a sample. First, a panel of tissue-specific transcripts is identified. Second, total RNA in plasma from a sample is determined using methods known in the art. Third, the total RNA is assessed against the panel of tissue-specific transcripts, and the total RNA is considered a summation these different tissue-specific transcripts. Quadratic programming can be used as a constrained optimization method to deduce the relative optimal contributions of different organs/tissues towards the cell-free transcriptome of the sample.

One or more databases of genetic information can be used to identify a panel of tissue-specific transcripts. Accordingly, aspects of the invention provide systems and methods for the use and development of a database. Particularly, methods of the invention utilize databases containing existing data generated across tissue types to identify the tissue-specific genes. Databases utilized for identification of tissue-specific genes include the Human 133A/GNF1H Gene Atlas and RNA-Seq Atlas, although any other database or literature can be used. In order to identify tissue-specific transcripts from one or more databases, certain embodiments employ a template-matching algorithm to the databases. Template matching algorithms used to filter data are known in the art, see e.g., Pavlidis P. Noble W S (2001) Analysis of strain and regional variation in gene expression in mouse brain. *Genome Biol* 2: research0042.1-0042.15.

In certain embodiments, quadratic programming is used as a constrained optimization method to deduce relative optimal contributions of different organs/tissues towards the cell-free transcriptome in a sample. Quadratic programming is known in the art and described in detail in Goldfarb and A. Idnani (1982). Dual and Primal-Dual Methods for Solving Strictly Convex Quadratic Programs. In J. P. Hennart (ed.), Numerical Analysis, Springer-Verlag, Berlin, pages226-239, and D. Goldfarb and A. Idnani (1983). A numerically stable dual method for solving strictly convex quadratic programs. Mathematical Programming, 27, 1-33.

FIG. 7 outlines exemplary process steps for determining the relative tissue contributions to a cell-free transcriptome of a sample. Using information provided by one or more tissue-specific databases, a panel of tissue-specific genes is generated with a template-matching function. A quality control function can be applied to filter the results. A blood sample is then analyzed to determine the relative contribution of each tissue-specific transcript to the total RNA of the sample. Cell-free RNA is extracted from the sample, and the cell-free RNA extractions are processed using one or more quantification techniques (e.g. standard mircoarrays and RNA-sequence protocols). The obtained gene expression values for the sample are then normalized. This involves rescaling of all gene expression values to the housekeeping genes. Next, the sample's total RNA is assessed against the panel of tissue-specific genes using quadratic programming in order to determine the tissue-specific relative contributions to the sample's cell-free transcriptome. The following constraints are employed to obtain the estimated relative contributions during the quadratic programming analysis: a) the RNA contributions of different tissues are greater than or equal to zero, and b) the sum of all contributions to the cell-free transcriptome equals one.

Method of the invention for determining the relative contributions for each tissue can be used to determine the reference level for the tissue. That is, a certain population of subjects (e.g., maternal, normal, cancerous, Alzheimer's (and various stages thereof)) can be subject to the deconvolution process outlined in FIG. 7 to obtain reference levels of tissue-specific gene expression for that patient population. When relative tissue contributions are considered individually, quantification of each of these tissue-specific transcripts can be used as a measure for the reference apoptotic rate of that particular tissue for that particular population. For example, blood from one or more healthy, normal individuals can be analyzed to determine the relative RNA contribution of tissues to the cell-free RNA transcriptome for healthy, normal individuals. Each relative RNA contribution of tissue that makes up the normal RNA transcriptome is a reference level for that tissue.

According to certain embodiments, an unknown sample of blood can be subject to process outlined in FIG. 7 to determine the relative tissue contributions to the cell-free RNA transcriptome of that sample. The relative tissue contributions of the sample are then compared to one or more reference levels of the relative contributions to a reference cell-free RNA transcriptome. If a specific tissue shows a contribution to the cell-free RNA transcriptome in the sample that is greater or less than the contribution of the specific tissue in a reference cell-free RNA transcriptome, then the tissue exhibiting differential contribution may be characterized accordingly. If the reference cell-free transcriptome represents a healthy population, a tissue exhibiting a differential RNA contribution in a sample cell-free transcriptome can be classified as unhealthy.

The biological sample can be blood, saliva, sputum, urine, semen, transvaginal fluid, cerebrospinal fluid, sweat, breast milk, breast fluid (e.g., breast nipple aspirate), stool, a cell or a tissue biopsy. In certain embodiments, the samples of the same biological sample are obtained at multiple different time points in order to analyze differential transcript levels in the biological sample over time. For example, maternal plasma may be analyzed in each trimester. In some embodiments, the biological sample is drawn blood and circulating nucleic acids, such as cell-free RNA. The cell-free RNA may be from different genomic sources is found in the blood or plasma, rather than in cells.

In a particular embodiment, the drawn blood is maternal blood. In order to obtain a sufficient amount of nucleic acids for testing, it is preferred that approximately 10-50 mL of blood be drawn. However, less blood may be drawn for a genetic screen in which less statistical significance is required, or in which the RNA sample is enriched for fetal RNA.

Methods of the invention involve isolating total RNA from a biological sample. Total RNA can be isolated from the biological sample using any methods known in the art. In certain embodiments, total RNA is extracted from plasma. Plasma RNA extraction is described in Enders et al., "The Concentration of Circulating Corticotropin-releasing Hormone mRNA in Maternal Plasma Is Increased in Preeclampsia," Clinical Chemistry 49:727-731, 2003. As described there, plasma harvested after centrifugation steps is mixed Trizol LS reagent (Invitrogen) and chloroform. The mixture is centrifuged, and the aqueous layer transferred to new tubes. Ethanol is added to the aqueous layer. The mixture is then applied to an RNeasy mini column (Qiagen) and processed according to the manufacturer's recommendations.

In the embodiments where the biological sample is maternal blood, the maternal blood may optionally be processed to enrich the fetal RNA concentration in the total RNA. For example, after extraction, the RNA can be separated by gel electrophoresis and the gel fraction containing circulatory RNA with a size of corresponding to fetal RNA (e.g., <300 bp) is carefully excised. The RNA is extracted from this gel slice and eluted using methods known in the art.

Alternatively, fetal specific RNA may be concentrated by known methods, including centrifugation and various enzyme inhibitors. The RNA is bound to a selective membrane (e.g., silica) to separate it from contaminants. The RNA is preferably enriched for fragments circulating in the plasma, which are less than less 300 bp. This size selection is done on an RNA size separation medium, such as an electrophoretic gel or chromatography material.

Flow cytometry techniques can also be used to enrich for fetal cells in maternal blood (Herzenberg et al., PNAS 76:1453-1455 (1979); Bianchi et al., PNAS 87:3279-3283 (1990); Bruch et al., Prenatal Diagnosis 11:787-798 (1991)). U.S. Pat. No. 5,432,054 also describes a technique for separation of fetal nucleated red blood cells, using a tube having a wide top and a narrow, capillary bottom made of polyethylene. Centrifugation using a variable speed program results in a stacking of red blood cells in the capillary based on the density of the molecules. The density fraction containing low-density red blood cells, including fetal red blood cells, is recovered and then differentially hemolyzed to preferentially destroy maternal red blood cells. A density gradient in a hypertonic medium is used to separate red blood cells, now enriched in the fetal red blood cells from lymphocytes and ruptured maternal cells. The use of a hypertonic solution shrinks the red blood cells, which increases their density, and facilitates purification from the more dense lymphocytes. After the fetal cells have been isolated, fetal RNA can be purified using standard techniques in the art.

Further, an agent that stabilizes cell membranes may be added to the maternal blood to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, Ginkgo biloba extract, diphenylhydantoin, perftoran, polyvinylpyrrolidone, phosphatidylserine, tegretol, PABA, disodium cromglycate, nedocromil sodium, phenyloin, zinc citrate, mexitil, dilantin, sodium hyaluronate, or polaxamer 188.

An example of a protocol for using this agent is as follows: The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at –80° C. Approximately two milliliters of the "buffy coat," which contains maternal cells, is placed into a separate tube and stored at –80° C.

Methods of the invention also involve preparing amplified cDNA from total RNA. cDNA is prepared and indiscriminately amplified without diluting the isolated RNA sample or distributing the mixture of genetic material in the isolated RNA into discrete reaction samples. Preferably, amplification is initiated at the 3' end as well as randomly throughout the whole transcriptome in the sample to allow for amplification of both mRNA and non-polyadenylated transcripts. The double-stranded cDNA amplification products are thus optimized for the generation of sequencing libraries for Next Generation Sequencing platforms. Suitable kits for amplifying cDNA in accordance with the methods of the invention include, for example, the Ovation® RNA-Seq System.

Methods of the invention also involve sequencing the amplified cDNA. While any known sequencing method can be used to sequence the amplified cDNA mixture, single molecule sequencing methods are preferred. Preferably, the amplified cDNA is sequenced by whole transcriptome shotgun sequencing (also referred to herein as ("RNA-Seq"). Whole transcriptome shotgun sequencing (RNA-Seq) can be accomplished using a variety of next-generation sequencing platforms such as the Illumina Genome Analyzer platform, ABI Solid Sequencing platform, or Life Science's 454 Sequencing platform.

Methods of the invention further involve subjecting the cDNA to digital counting and analysis. The number of amplified sequences for each transcript in the amplified sample can be quantitated via sequence reads (one read per amplified strand). Unlike previous methods of digital analysis, sequencing allows for the detection and quantitation at the single nucleotide level for each transcript present in a biological sample containing a genetic material from different genomic sources and therefore multiple transcriptomes.

After digital counting, the ratios of the various amplified transcripts can compared to determine relative amounts of differential transcript in the biological sample. Where multiple biological samples are obtained at different time-points, the differential transcript levels can be characterized over the course of time.

Differential transcript levels within the biological sample can also be analyzed using via microarray techniques. The amplified cDNA can be used to probe a microarray containing gene transcripts associated with one or conditions or diseases, such as any prenatal condition, or any type of cancer, inflammatory, or autoimmune disease.

It will be understood that methods and any flow diagrams disclosed herein can be implemented by computer program instructions. These program instructions may be provided to a computer processor, such that the instructions, which execute on the processor, create means for implementing the actions specified in the flowchart blocks or described in methods for assessing tissue disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes or even in a different sequence than illustrated without departing from the scope or spirit of the invention.

The computer program instructions can be, stored on any suitable computer-readable medium including, but not limited to, RAM, ROM, EEPROM, flash memory or other memory technology. CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

In certain aspects, methods of the invention can be used to determine cell-free RNA transcripts specific to the certain tissue, and use those transcripts to diagnose disorders and diseases associated with that tissue. In certain embodiments, methods of the invention can be used to determine cell-free RNA transcripts specific to the brain, and use those transcripts to diagnose neurological disorders (such as Alzheimer's disease). For example, methods of profiling cell-free RNA described herein can be used to differentiate subjects with neurological disorders from normal subjects because cell-free RNA transcripts associated with certain neurological disorders present at statistically-significant different levels than the same cell-free RNA transcripts in normal healthy populations. As a result, one is able to utilize levels of those RNA transcripts for clear and simple diagnostic tests.

In accordance with certain embodiments, cell-free RNA transcripts that source from brain tissue can be further examined as potential biomarkers for neurological disorders. In certain embodiments, once a brain-specific cell-free RNA transcript is determined, levels of the brain-specific cell-free RNA transcripts in normal patients are compared to patients with certain neurological disorders. In instances where the levels of brain specific cell-free RNA transcript consistently exhibit a statistically significant difference between subjects with a certain neurological disorder and normal subjects, then that brain-specific cell-free RNA transcript can be used as a biomarker for that neurological disorder. For example, the inventors have found that measurements of PSD3 and APP cell-free RNA transcript levels in plasma for Alzheimer disorder patients are statistically different from the levels of PSD3 and APP cell-free RNA in normal subjects.

According to certain aspects, a neurological disorder is indicated in a patient based on a comparison of the patient's circulating nucleic acid that is specific to brain tissue and circulating nucleic acid of a reference or multiple references that is specific to brain tissue. In particular, the circulating nucleic acid is RNA, but may also be DNA. In certain embodiments, levels of brain-specific circulating RNA present in a reference population are used as thresholds that are indicative with a condition. The condition may be a normal healthy condition or may be a diseased condition (e.g. neurological disorder, Alzheimer's disease generally or particular stage of Alzheimer's disease). When the threshold is indicative of a diseased condition, the patient's transcript levels that are underexpressed or overexpressed in comparison to the threshold may indicate that the patient does not have the disease. When the threshold is indicative of normal condition, the patient's transcript levels that are underexpressed or overexpressed in comparison to the threshold may indicate that the patient has the disease.

Reference RNA levels (e.g. levels of circulating RNA) may be obtained by statistically analyzing the brain-specific transcript levels of a defined patient population. The reference levels may pertain to a healthy patient population or a patient population with a particular neurological disorder. In further examples, the references levels may be tailored to a more specific patient population. For example, a reference level may correlate to a patient population of a certain age and/or correspond to a patient population exhibiting symptoms associated with a particular stage of a neurological disorder. Other factors for tailoring the patient population for reference levels may include sex, familial history, environmental exposure, and/or phenotypic traits.

Brain-specific genes or transcripts may be determined by deconvolving the cell-free transcriptome as described above and outlined in FIG. 7. Brain-specific genes or transcripts may also be determined by directly analyzing brain tissue. In addition, Tables 1 and 2, as listed in Example 4 below, provide genes whose expression profiles are unique to certain tissue types. Particularly, Tables 1 and 2 list brain-specific genes corresponding with hypothalamus as well as genes corresponding with the whole brain (e.g. most brain tissue), prefrontal cortex, thalamus, etc. In certain embodiments, brain-specific genes or transcripts include APP, PSD3, MOBP, MAG, SLC2A1, TCF7L2, CDH22, CNTF, and PAQR6.

The brain-specific transcripts used in methods of the invention may correspond to cell-free transcripts released from certain types of brain tissue. The types of brain tissue include the pituitary, hypothalamus, thalamus, corpus callosum, cerebrum, cerebral cortex, and combinations thereof. In particular embodiments, the brain-specific transcripts correspond with the hypothalamus. The hypothalamus is bounded by specialized brain regions that lack an effective blood/brain barrier, and thus transcripts released from the hypothalamus are likely to be introduced into blood or plasma.

Figure 19:
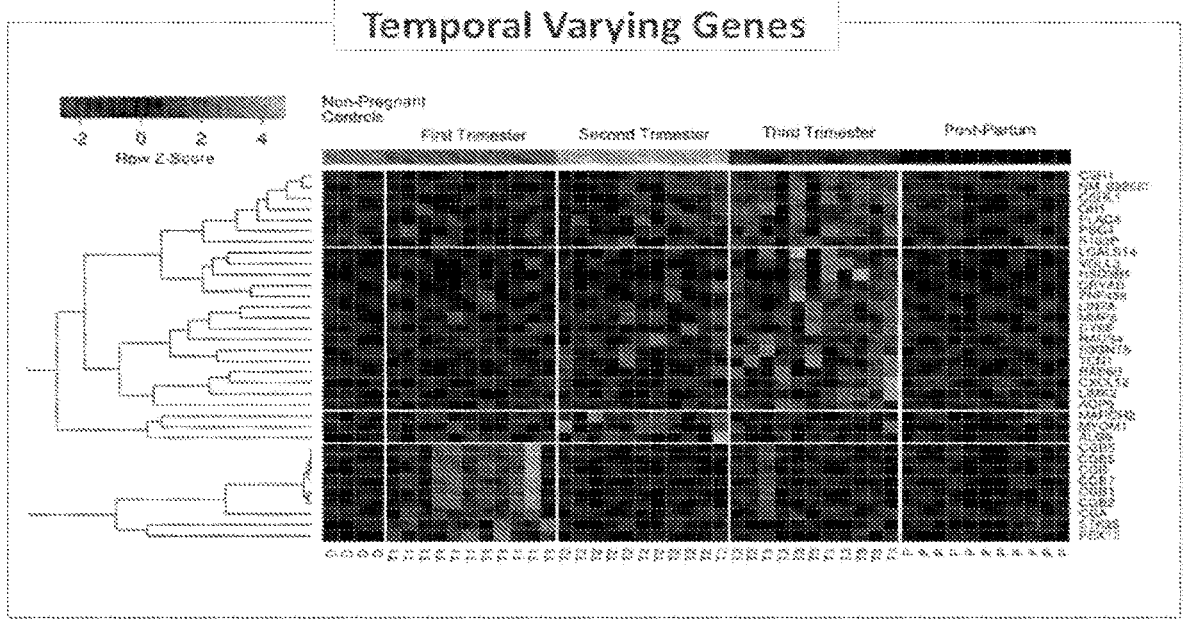
FIG. 19 illustrates a heat map of temporal varying genes obtained from microarray analysis. Unsupervised clustering was performed on genes across different time points. Cluster of genes belongs to the CGB family of genes which are known to be expressed at high levels during the first trimester exhibited corresponding high levels of RNA in the first trimester.

FIG. 19 illustrates the difference in levels of PSD3 and APP cell-free RNA between subjects with Alzheimer's and normal subjects. Measurements of PSD3 and APP cell free RNA transcripts levels in plasma shows that the levels of these two transcripts are elevated in AD patients and can be used to cleanly group the AD patients from the normal patients. Shown in the figure are only two potential transcripts showing significant diagnostic potential. High throughput microfluidics chip allow for simultaneous measurements of other brain specific transcripts which can improve the classification process.

In particular aspects, brain-specific transcripts are used to characterize and diagnose neurological disorders. The neurological disorder characterized may include degenerative neurological disorders, such as Alzheimer's disease, Parkinson's disease, Huntington's disease, and some types of multiple sclerosis. The most common neurological disorder is Alzheimer's disease. In some instances, the neurological disorder is classified by the extent of cognitive impairment, which may include no impairment, mild impairment, moderate impairment, and severe impairment.

Alzheimer's disease is characterized into stages based on the cognitive symptoms that occur as the disease progresses. Stage 1 involves no impairment (normal function). The person does not experience any memory problems or signs of dementia. Stage 2 involves a very mild decline in cognitive functions. During Stage 2, a person may experience mild memory loss, but cognitive impairment is not likely noticeable by friends, family, and treating physicians. Stage 3 involves a mild cognitive decline, in which friends, family, and treating physicians may notice difficulties in the individual's memory and ability to perform tasks. For example, trouble identifying certain words, noticeable difficulty in performing tasks in social or work settings, forgetting just-read materials. Stage 4 involves moderate cognitive decline, which is noticeable and causes a significant impairment on the individual's daily life. In Stage 4, the individual will have trouble performing everyday complex tasks, such as managing financings and planning social gatherings, will have trouble remembering their own personal history, and becomes moody or withdrawn. Stage 5 involves moderately severe cognitive decline, in which gaps in memory and thinking are noticeable and the individual will begin to need help with certain activities. In Stage 5, individuals will be confused about the day, will have trouble with recalling particular details (such as phone number and street address), but will be able to remember significant details about themselves and their loved ones. Stage 6 involves severe cognitive decline, as the individual's memory continues to worsen. Individuals in Stage 6 will likely need extensive help with daily activities because they lose awareness of their surroundings and while they often remember certain tasks, they forget how to complete them or make mistakes (e.g. wearing pajamas during the day, forgetting to rinse after shampooing, wearing shoes on wrong side of the foot). Stage 7 involves very severe cognitive decline and is the final stage of Alzheimer's disease. In Stage 7, individuals lose their ability to respond to the environment, remember others, carry on a conversation, and control movement. Individuals need help with daily care, eating, dressing, using the bathroom, and have abnormal reflexes and tense muscles. Individuals may still be verbal, but will not make sense or relate to the present.

In certain embodiments, methods for assessing a neurological disorder involve a comparison of one or more brain-specific transcripts of an individual to a set of predictive variables correlated with the neurological disorder. The set of predictive variables may include a variety of reference levels that are brain specific. For instance, the set of predictive variables may include brain-specific transcript levels of a plurality of references. For example, one reference level may correspond to a normal patient population and another reference level may correspond to a patient population with the neurological disorder. In further examples, the references may correspond to more specific patient populations. For example, each reference level may correlate to a patient population of a certain age and/or correspond to a patient population exhibiting symptoms associated with a particular stage of a neurological disorder. Other factors for tailoring the patient population for reference levels may include sex, familial history, environmental exposure, and/or phenotypic traits.

Statistical analyses can be used to determine brain-specific reference levels of certain patient populations (such as those discussed above). Statistical analyses for identifying trends in patient populations and comparing patient populations are known in the art. Suitable statistical analyses include, but are not limited to, clustering analysis, principle component analysis, non-parametric statistical analyses (e.g. Wilcoxon tests), etc.

In addition, statistical analyses may be used to statistically significant deviations between the individual's circulating nucleic specific to brain tissue and that of a reference. When the reference is based on a diseased population, statistically significant deviations of the individual's brain-specific circulating RNA to those of the diseased population are indicative of no neurological disorder. When the reference is based on a normal population, statistically significant deviations of the individual's brain-specific circulating RNA to those of the normal population are indicative of a neurological disorder. Methods of determining statistical significance are known in the art. P-values and odds ratio can be used for statistical inference. Logistic regression models are common statistical classification models. In addition, Chi-Square tests and T-test may also be used to determine statistical significance.

Methods of the invention can also be used to identify one or more biomarkers associated with a neurological disorder. In such aspects, brain-specific transcripts of an individual or patient population suspected of having or actually having a neurological disorder (e.g. exhibiting impaired cognitive functions) are compared to reference brain-specific transcript (e.g. a healthy, normal control). The brain-specific transcripts of the individual or patient population that are differentially expressed as compared to the reference may then be identified as biomarkers of the neurological disorder. In certain embodiments, only differentially expressed brain-specific transcripts that are statistically significant are identified as biomarkers.

In certain embodiments, methods of the invention provide recommend a course of treatment based on the clinical indications determined by comparing of the patient's circulating brain-specific RNA and the reference. Depending on the diagnosis, the course of treatment may include medicinal therapy, behavioral therapy, sleep therapy, and combinations thereof. The course of treatment and diagnosis may be provided in a read-out or a report.

EXAMPLES

Example 1: Profiling Maternal Plasma Cell-Free RNA by RNA Sequencing-A Comprehensive Approach Overview:

The plasma RNA profiles of 5 pregnant women were collected during the first trimester, second trimester, postpartum, as well as those of 2 non-pregnant female donors and 2 male donors using both microarray and RNA-Seq.

Among these pregnancies, there were 2 pregnancies with clinical complications such as premature birth and one pregnancy with bi-lobed placenta. Comparison of these pregnancies against normal cases reveals genes that exhibit significantly different gene expression pattern across different temporal stages of pregnancy. Application of such technique to samples associated with complicated pregnancies may help identify transcripts that can be used as molecular markers that are predictive of these pathologies.

Study Design and Methods:

Subjects

Samples were collected from 5 pregnant women were during the first trimester, second trimester, third trimester, and post-partum. As a control, blood plasma samples were also collected from 2 non-pregnant female donors and 2 male donors.

Blood Collection and Processing

Blood samples were collected in EDTA tube and centrifuged at 1600 g for 10 min at 4° C. Supernatant were placed in 1 ml aliquots in a 1.5 ml microcentrifuge tube which were then centrifuged at 16000 g for 10 min at 4° C. to remove residual cells. Supernatants were then stored in 1.5 ml microcentrifuge tubes at −80° C. until use.

RNA Extraction and Amplification

The cell-free maternal plasma RNAs was extracted by Trizol LS reagent. The extracted and purified total RNA was converted to cDNA and amplified using the RNA-Seq Ovation Kit (NuGen). (The above steps were the same for both Microarray and RNA-Seq sample preparation).

The cDNA was fragmented using DNase I and labeled with Biotin, following by hybridization to Affymetrix GeneChip ST 1.0 microarrays. The Illumina sequencing platform and standard Illumina library preparation protocols were used for sequencing.

Data Analysis:

Correlation Between Microarray and RNA-Seq

The RMA algorithm was applied to process the raw microarray data for background correction and normalization. RPKM values of the sequenced transcripts were obtained using the CASAVA 1.7 pipeline for RNA-seq. The RPKM in the RNA-Seq and the probe intensities in the microarray were converted to log 2 scale. For the RNA-Seq data, to avoid taking the log of 0, the gene expressions with RPKM of 0 were set to 0.01 prior to taking logs. Correlation coefficients between these two platforms ranges were then calculated.

Differential Expression of RNA Transcripts Levels Using RNA-Seq

Differential gene expression analysis was performed using edgeR, a set of library functions which are specifically written to analyze digital gene expression data. Gene Ontology was then performed using DAVID to identify for significantly enriched GO terms.

Principle Component Analysis & Identification of Significant Time Varying Genes

Principle component analysis was carried out using a custom script in R. To identify time varying genes, the time course library of functions in R were used to implement empirical Bayes methods for assessing differential expression in experiments involving time course which in our case are the different trimesters and post-partum for each individual patients.

Results and Discussion

RNA-Seq Reveals that Pregnancy-Associated Transcripts are Detected at Significantly Different Levels Between Pregnant and Non-Pregnant Subjects.

A comparison of the transcripts level derived using RNA-Seq and Gene Ontology Analysis between pregnant and non-pregnant subjects revealed that transcripts exhibiting differential transcript levels are significantly associated with female pregnancy, suggesting that RNA-Seq are enabling observation of real differences between these two class of transcriptome due to pregnancy. The top rank significantly expressed gene is PLAC4 which has also been known as a target in previous studies for developing RNA based test for trisomy 21. A listing of the top detected female pregnancy associated differentially expressed transcripts is shown in FIG. 1.

Principle Component Analysis (PCA) on Plasma Cell Free RNA Transcripts Levels in Maternal Plasma Distinguishes Between Pre-Mature and Normal Pregnancy Using the plasma cell free transcript level profiles as inputs for Principle Component Analysis, the profile from each patient at different time points clustered into different pathological clusters suggesting that cell free plasma RNA transcript profile in maternal plasma may be used to distinguish between pre-term and non-preterm pregnancy.

Plasma Cell free RNA levels were quantified using both microarray and RNA-Seq. Transcripts expression levels profile from microarray and RNA-Seq from each patient are correlated with a Pearson correlation of approximately 0.7. Plots of the two main principal components for cell free RNA transcript levels is shown in FIG. 2.

Figures 1, 2, 3A:
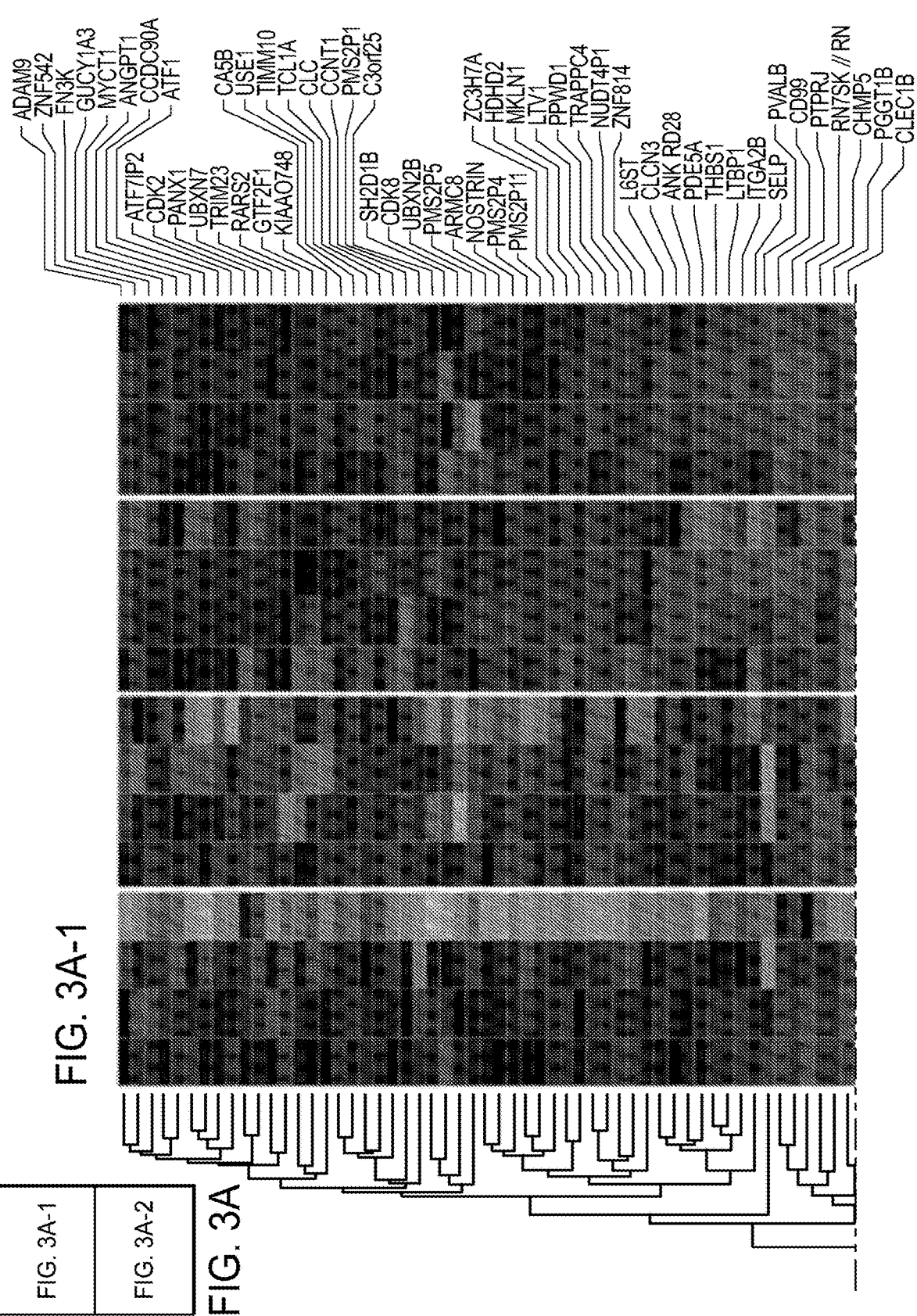
FIG. 1 depicts a listing of the top detected female pregnancy associated differentially expressed transcripts.
FIG. 3A depicts a heatmap of the top 100 cell free transcript levels exhibiting different temporal levels in pre-term and normal pregnancy using microarrays. The heat map of FIG. 3A is split across FIG. 3A-1 and FIG. 3A-2, as indicated by the graphical figure outline.
Figures 2, 3A:
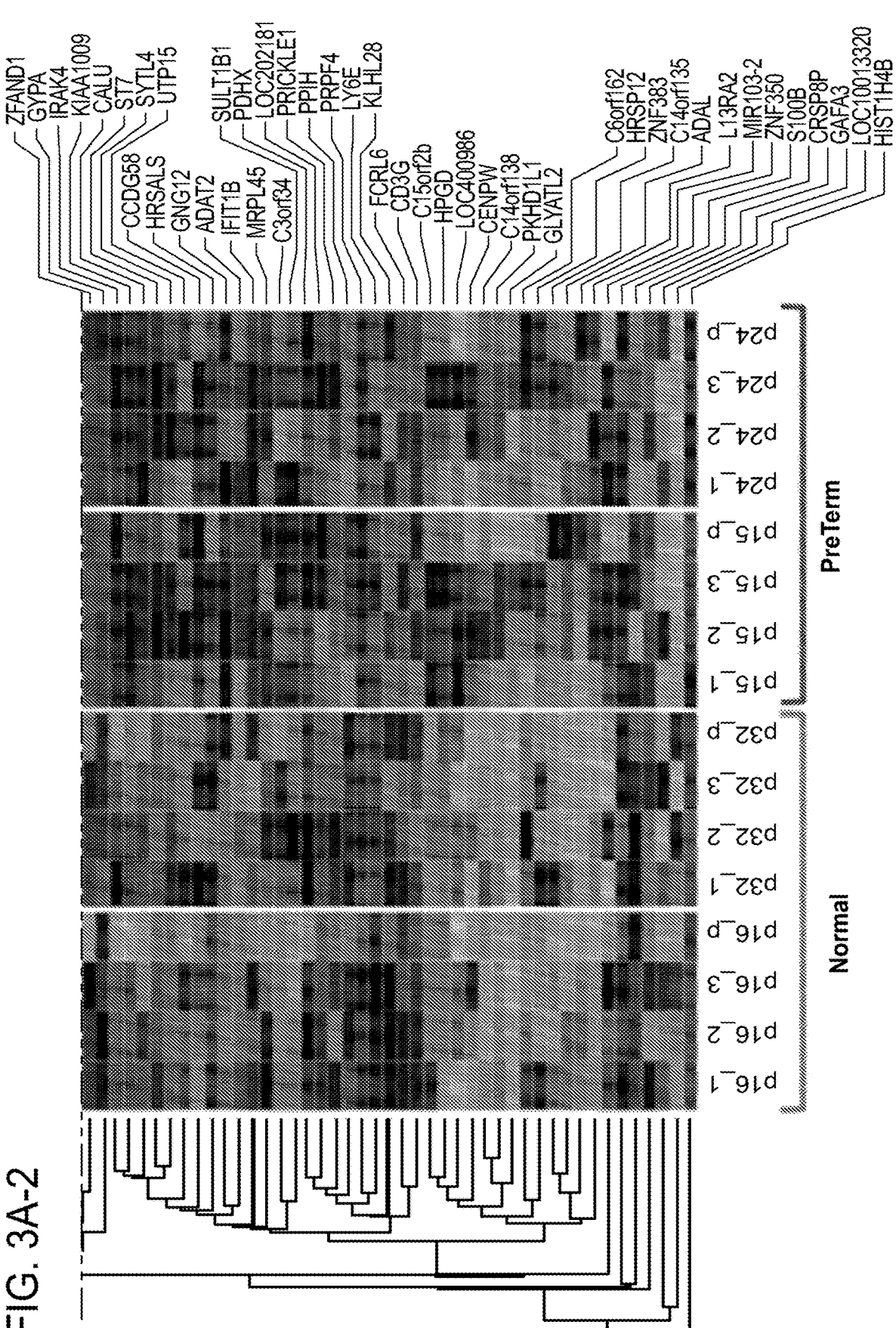
Figures 2, 3B:
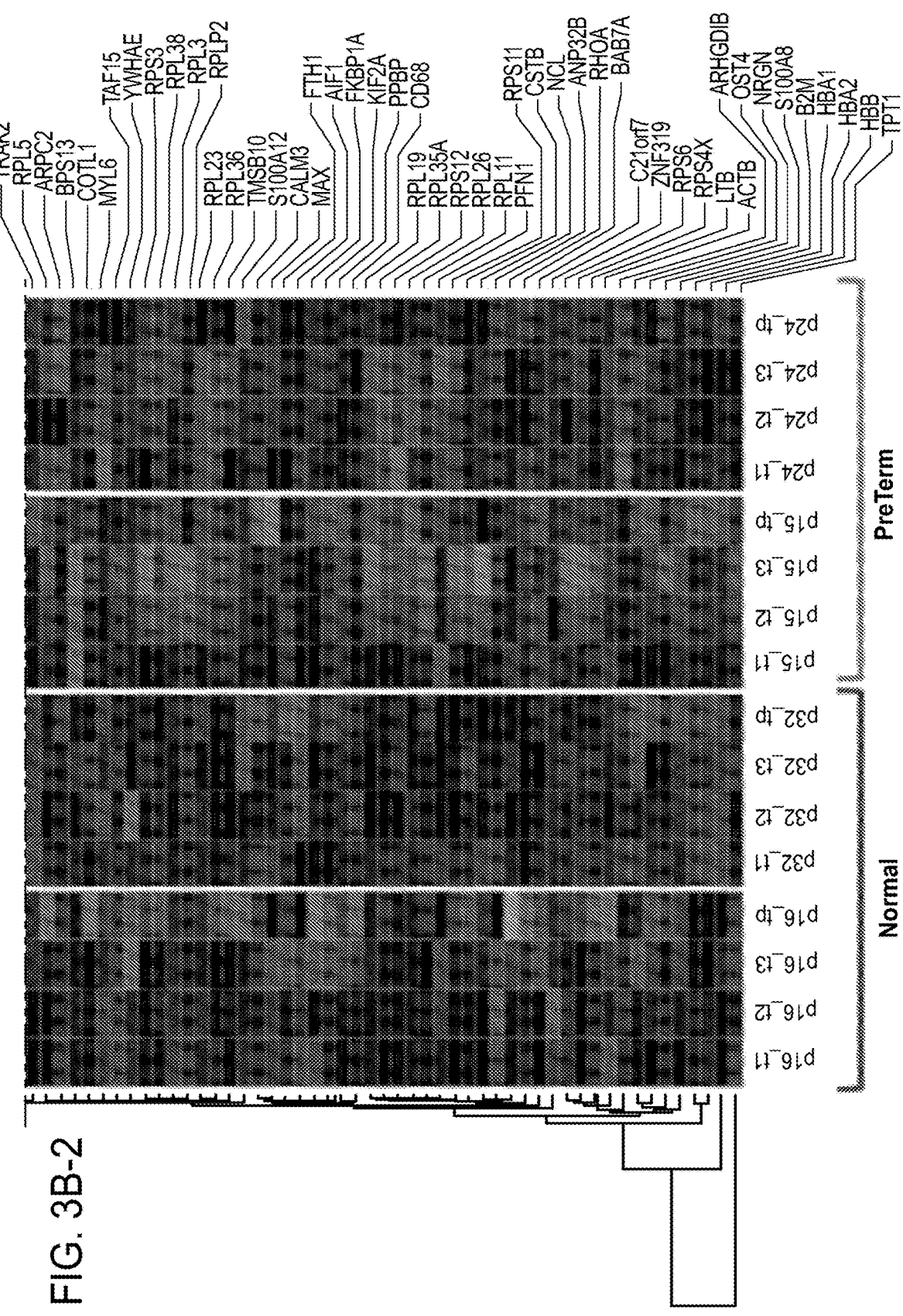
FIG. 3B depicts heatmap of the top 100 cell free transcript levels exhibiting different temporal levels in preterm and normal pregnancy using RNA-Seq. The heat map of FIG. 3B is split across FIG. 3B-1 and FIG. 3B-2, as indicated by the graphical figure outline.

Identification of Cell Free RNA Transcripts in Maternal Plasma Exhibiting Significantly Different Time Varying Trends Between Pre-Term and Normal Pregnancy Across all Three Trimesters and Post-Partum A heatmap of the top 100 cell free transcript levels exhibiting different temporal levels in preterm and normal pregnancy using microarrays is shown in FIG. 3A. A heatmap of the top 100 cell free transcript levels exhibiting different temporal levels in preterm and normal pregnancy using RNA-Seq is shown in FIG. 3B.

Common Cell Free RNA Transcripts Identified by Microarray and RNA-Seq which Exhibit Significantly Different Time Varying Trends Between Pre-Term and Normal Pregnancy Across all Three Trimesters and Post-Partum A ranking of the top 20 transcripts differentially expressed between pre-term and normal pregnancy is shown in FIG. 4. These top 20 common RNA transcripts were analyzed using Gene Ontology and were shown to be enriched for proteins that are attached (integrated or loosely bound) to the plasma membrane or on the membranes of the platelets (see FIG. 5).

Gene Expression Profiles for PVALB

The protein encoded by PVALB gene is a high affinity calcium ion-binding protein that is structurally and functionally similar to calmodulin and troponin C. The encoded protein is thought to be involved in muscle relaxation. As shown in FIG. 6, the gene expression profile for PVALB across the different trimesters shows the premature births [highlighted in blue] has higher levels of cell free RNA transcripts found as compared to normal pregnancy.

Conclusion:

Results from quantification and characterization of maternal plasma cell-free RNA using RNA-Seq strongly suggest that pregnancy associated transcripts can be detected.

Furthermore, both RNA-Seq and microarray methods can detect considerable gene transcripts whose level showed differential time trends that has a high probability of being associated with premature births.

The methods described herein can be modified to investigate pregnancies of different pathological situations and can also be modified to investigate temporal changes at more frequent time points.

Example 2: Quantification of Tissue-Specific Cell-Free RNA Exhibiting Temporal Variation During Pregnancy Overview:

Cell-free fetal DNA found in maternal plasma has been exploited extensively for non-invasive diagnostics. In contrast, cell-free fetal RNA which has been shown to be similarly detected in maternal circulation has yet been applied widely as a form of diagnostics. Both fetal cell-free RNA and DNA face similar challenges in distinguishing the fetal from maternal component because in both cases the maternal component dominates. To detect cell-free RNA of fetal origin, focus can be placed on genes that are highly expressed only during fetal development, which are subsequently inferred to be of fetal in origin and easily distinguished from background maternal RNA. Such a perspective is collaborated by studies that has established that cell-free fetal RNA derived from genes that are highly expressed in the placenta are detectable in maternal plasma during pregnancy.

A significant characteristic that set RNA apart from DNA can be attributed to RNA transcripts dynamic nature which is well reflected during fetal development. Life begins as a series of well-orchestrated events that starts with fertilization to form a single-cell zygote and ends with a multi-cellular organism with diverse tissue types. During pregnancy, majority of fetal tissues undergoes extensive remodeling and contain functionally diverse cell types. This underlying diversity can be generated as a result of differential gene expression from the same nuclear repertoire: where the quantity of RNA transcripts dictate that different cell types make different amount of proteins, despite their genomes being identical. The human genome comprises approximately 30,000 genes. Only a small set of genes are being transcribed to RNA within a particular differentiated cell type. These tissue specific RNA transcripts have been identified through many studies and databases involving developing fetuses of classical animal models. Combining known literature available with high throughput data generated from samples via sequencing, the entire collection of RNA transcripts contained within maternal plasma can be characterized.

Fetal organ formation during pregnancy depends on successive programs of gene expression. Temporal regulation of RNA quantity is necessary to generate this progression of cell differentiation events that accompany fetal organ genesis. To unravel similar temporal dynamics for cell free RNA, the expression profile of maternal plasma cell free RNA, especially the selected fetal tissue specific panel of genes, as a function across all three trimesters during pregnancy and post-partum were analyzed. Leveraging high throughput qPCR and sequencing technologies capability for simultaneous quantification of cell free fetal tissue specific RNA transcripts, a system level view of the spectrum of RNA transcripts with fetal origins in maternal plasma was obtained. In addition, maternal plasma was analyzed to deconvolute the heterogeneous cell free transcriptome of fetal origin a relative proportion of the different fetal tissue types. This approach incorporated physical constraints regarding the fetal contributions in maternal plasma, specifically the fraction of contribution of each fetal tissues were required to be non-negative and sum to one during all three trimesters of the pregnancy. These constraints on the data set enabled the results to be interpreted as relative proportions from different fetal organs. That is, a panel of previously selected fetal tissue-specific RNA transcripts exhibiting temporal variation can be used as a foundation for applying quadratic programing in order to determine the relative tissue-specific RNA contribution in one or more samples.

When considered individually, quantification of each of these fetal tissue specific transcripts within the maternal plasma can be used as a measure for the apoptotic rate of that particular fetal tissue during pregnancy. Normal fetal organ development is tightly regulated by cell division and apoptotic cell death. Developing tissues compete to survive and proliferate, and organ size is the result of a balance between cell proliferation and death. Due to the close association between aberrant cell death and developmental diseases, therapeutic modulation of apoptosis has become an area of intense research, but with this comes the demand for monitoring the apoptosis rate of specific. Quantification of fetal cell-free RNA transcripts provide such prognostic value, especially in premature births where the incidence of apoptosis in various organs of these preterm infants has been have been shown to contribute to neurodevelopmental deficits and cerebral palsy of preterm infants.

Sample Collection and Study Design

Selection of Fetal Tissue Specific Transcript Panel

To detect the presence of these fetal tissue-specific transcripts, a list of known fetal tissue specific genes was prepared from known literature and databases. The specificity for fetal tissues was validated by cross referencing between two main databases: TISGeD (Xiao, S.-J., Zhang, C. & Ji, Z.-L. TiSGeD: a Database for Tissue-Specific Genes. *Bioinformatics* (Oxford, England) 26, 1273-1275 (2010)) and BioGPS (Wu. C. et al. BioGPS: an extensible and customizable portal for querying and organizing gene annotation resources. *Genome biology* 10, R130 (2009); Su, A. I. et al. A gene atlas of the mouse and human protein-encoding transcriptomes. *Proceedings of the National Academy of Sciences of the United States of America* 101, 6062-7 (2004)). Most of these selected transcripts are associated with known fetal developmental processes. This list of genes was overlapped with RNA sequencing and microarray data to generate the panel of selected fetal tissue-specific transcripts shown in FIG. 8.

Subjects

Samples of maternal blood were collected from normal pregnant women during the first trimester, second trimester, third trimester, and post-partum. For positive controls, fetal tissue specific RNA from the various fetal tissue types were bought from Agilent. Negative controls for the experiments were performed with the entire process with water, as well as with samples that did not undergoes the reverse transcription process.

Blood Collection and Processing

At each time-point, 7 to 15 mL of peripheral blood was drawn from each subject. Blood was centrifuged at 1600 g for 10 mins and transferred to microcentrifuge tubes for further centrifugation at 16000 g for 10 mins to remove residual cells. The above steps were carried out within 24 hours of the blood draw. Resulting plasma is stored at −80 Celsius for subsequent RNA extractions.

RNA Extraction

Cell free RNA extractions were carried using Trizol followed by Qiagen's RNeasy Mini Kit. To ensure that there are no contaminating DNA, DNase digestion is performed after RNA elution using RNase free DNase from Qiagen. Resulting cell free RNA from the pregnant subjects was then processed using standard microarrays and Illumina RNA-seq protocols. These steps generate the sequencing library that we used to generate RNA-seq data as well as the microarray expression data. The remaining cell free RNA are then used for parallel qPCR.

Parallel qPCR of Selected Transcripts

Accurate quantification of these fetal tissue specific transcripts was carried out using the Fluidigm BioMark system (See e.g. Spurgeon, S. L., Jones, R. C. & Ramakrishnan, R. High throughput gene expression measurement with real time PCR in a microfluidic dynamic array. *PloS one* 3, e1662 (2008)). This system allows for simultaneous query of a panel of fetal tissue specific transcripts. Two parallel forms of inquiry were conducted using different starting source of material. One was using the cDNA library from the Illumina sequencing protocol and the other uses the eluted RNA directly. Both sources of material were amplified with evagreen primers targeting the genes of interest. Both sources, RNA and cDNA, were preamplified. cDNA is preamplified using evagreen PCR supermix and primers. RNA source is preamplified using the CellsDirect One-Step qRT-PCR kit from Invitrogen. Modifications were made to the default One-Step qRT-PCR protocol to accommodate a longer incubation time for reverse transcription. 19 cycles of preamplification were conducted for both sources and the collected PCR products were cleaned up using Exonuclease I Treatment. To increase the dynamic range and the ability to quantify the efficiency of the later qPCR steps, serial dilutions were performed on the PCR products from 5 fold, 10 fold and 10 fold dilutions. Each of the collected maternal plasma from individual pregnant women across the time points went through the same procedures and was loaded onto 48×48 Dynamic Array Chips from Fluidigm to perform the qPCR. For positive control, fetal tissue specific RNA from the various fetal tissue types were bought from Agilent. Each of these RNA from fetal tissues went through the same preamplification and clean-up steps. A pool sample with equal proportions of different fetal tissues was created as well for later analysis to deconvolute the relative contribution of each tissue type in the pooled samples. All collected data from the Fluidigm BioMark system were pre-processed using Fluidigm Real Time PCR Analysis software to obtain the respective Ct values for each of the transcript across all samples. Negative controls of the experiments were performed with the entire process with water, as well as with samples that did not undergoes the reverse transcription process.

Figure 9A:
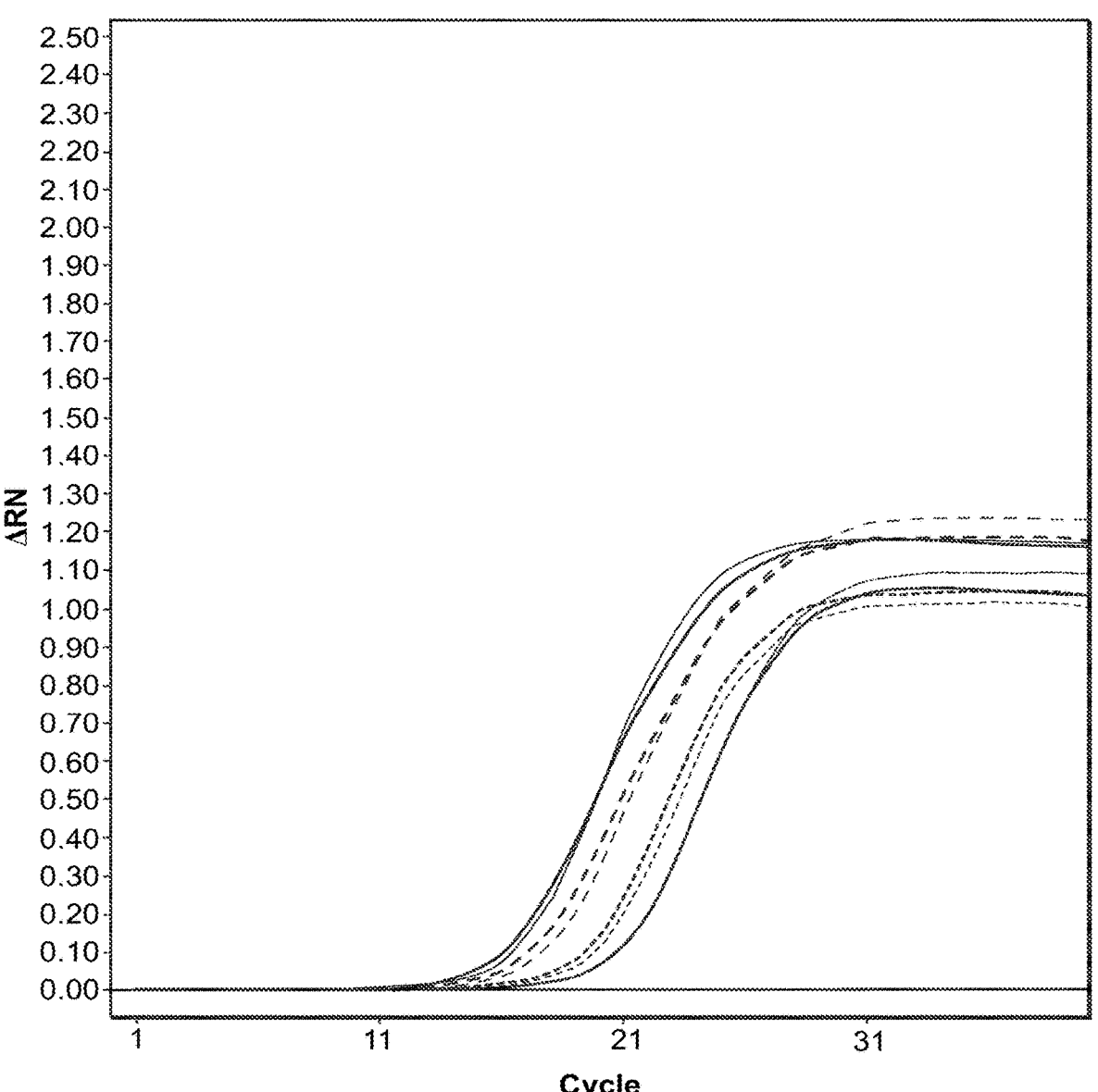
FIGS. 9A and 9B depict the raw data of parallel quantification of the fetal tissue-specific transcripts showing changes across maternal time-points (first trimester, second trimester, third trimester, and post partum) using the actual cell free RNA as well as the cDNA library of the same cell free RNA.
Figure 9B:
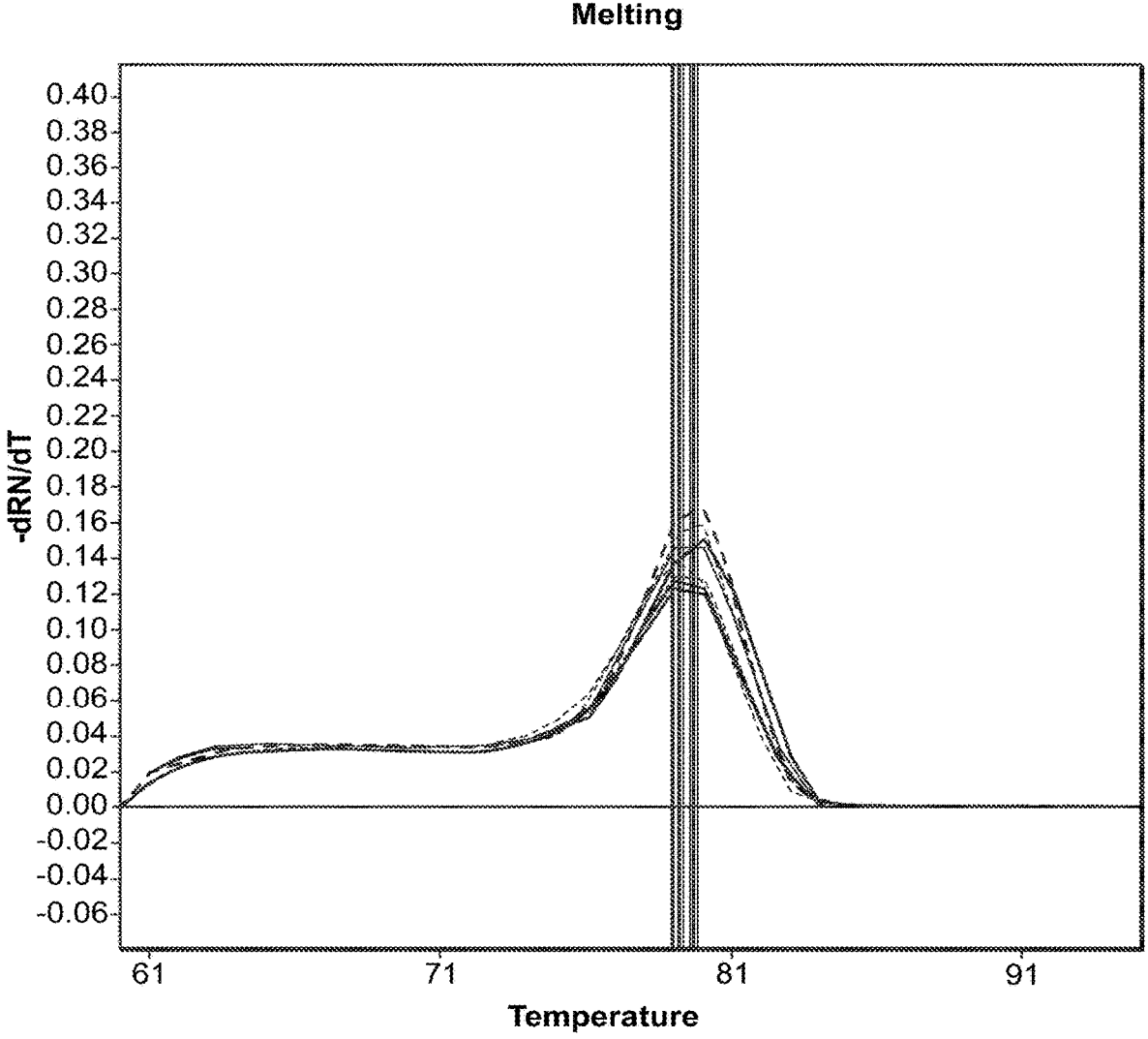

Data Analysis:

Fetal tissue specific RNA transcripts clear from the maternal peripheral bloodstream within a short period after birth. That is, the post-partum cell-free RNA transcriptome of maternal blood lacks fetal tissue specific RNA transcripts. As a result, it is expected that the quantity of these fetal tissue-specific transcripts to be higher before than after birth. The data of interest were the relative quantitative changes of the tissue specific transcripts across all three trimesters of pregnancy as compared to this baseline level after the baby is born. As described the methods, the fetal tissue-specific transcripts were quantified in parallel both using the actual cell-free RNA as well as the cDNA library of the same cell-free RNA. An example of the raw data obtained is shown in FIGS. 9A and 9B. The qPCR system gave a better quality readout using the cell-free RNA as the initial source. Focusing on the qPCR results from the direct cell-free RNA source, the analysis was conducted by comparing the fold changes level of each of these fetal tissue specific transcripts across all three trimesters using the post-partum level as the baseline for comparison. The Delta-Delta Ct method was employed (Schmittgen, T. D. & Livak, K. J. Analyzing real-time PCR data by the comparative CT method. Nature Protocols 3, 1101-1108 (2008)). Each of the transcript expression level was compared to the housekeeping genes to get the delta Ct value. Subsequently, to compare each trimesters to after birth, the delta-delta Ct method was applied using the post-partum data as the baseline.

Figure 10B:
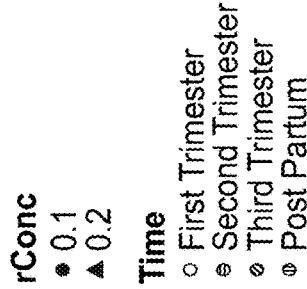
FIG. 10B depicts the same results segmented across the two subjects labeled as P53 & P54.
Figure 11B:
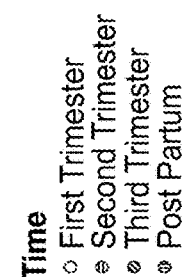
FIG. 11B depicts the same results segmented across the two subjects labeled as P53 & P54.

Results and Discussion:

As shown in FIGS. 10, 11, and 12, the tissue-specific transcripts are generally found to be at a higher level during the trimesters as compared to after-birth. In particular, the tissue-specific panel of placental, fetal brain and fetal liver specific transcripts showed the same bias, where these transcripts are typically found to exist at higher levels during pregnancy then compared to after birth. Between the different trimesters, a general trend showed that the quantity of these transcripts increase with the progression into pregnancy.

Biological Significance of Quantified Fetal Tissue-Specific RNA: Most of the transcripts in the panel were involved in fetal organ development and many are also found within the amniotic fluid. Once such example is ZNF238. This transcript is specific to fetal brain tissue and is known to be vital for cerebral cortex expansion during embryogenesis when neuronal layers are formed. Loss of ZNF238 in the central nervous system leads to severe disruption of neurogenesis, resulting in a striking postnatal small-brain phenotype. Using methods of the invention, one can determine whether ZNF238 is presenting in healthy, normal levels according to the stage of development.

Known defects due to the loss of ZNF238 include a striking postnatal small-brain phenotype: microcephaly, agenesis of the corpus callosum and cerebellar hypoplasia. Microcephaly can sometimes be diagnosed before birth by prenatal ultrasound. In many cases, however, it might not be evident by ultrasound until the third trimester. Typically, diagnosis is not made until birth or later in infancy upon finding that the baby's head circumference is much smaller than normal. Microcephaly is a life-long condition and currently untreatable. A child born with microcephaly will require frequent examinations and diagnostic testing by a doctor to monitor the development of the head as he or she grows. Early detection of ZNf238 differential expression using methods of the invention provides for prenatal diagnosis and may hold prognostic value for drug treatments and dosing during course of treatment.

Beyond ZNF238, many of the characterized transcripts may hold diagnostic value in developmental diseases involving apoptosis, i.e., diseases caused by removal of unnecessary neurons during neural development. Seeing that apoptosis of neurons is essential during development, one could extrapolate that similar apoptosis might be activated in neurodegenerative diseases such as Alzheimer's disease, Huntington's disease, and amyotrophic lateral sclerosis. In such a scenario, the methodology described herein will allow for close monitoring for disease progression and possibly an ideal dosage according to the progression.

Deducing relative contributions of different fetal tissue types: Differential rate of apoptosis of specific tissues may directly correlate with certain developmental diseases. That is, certain developmental diseases may increase the levels of a particular specific RNA transcripts being observed in the maternal transcriptome. Knowledge of the relative contribution from various tissue types will allow for observations of these types of changes during the progression of these diseases. The quantified panel of fetal tissue specific transcripts during pregnancy can be considered as a summation of the contributions from the various fetal tissues (See FIG. 25).

Expressing, $$Y_i = \sum_j \pi_i x_{ij} + \varepsilon$$

where Y is the observed transcript quantity in maternal plasma for gene i, X is the known transcript quantity for gene i in known fetal tissue j and & the normally distributed error. Additional physical constraints includes:

1. Summation of all fraction contributing to the observed quantification is 1, given by the condition: $\Sigma\pi_i=1$
2. All the contribution from each tissue type has to greater than or equal zero. There is no physical meaning to having a negative contribution. This is given by $\pi_i\geq0$, since $\pi$ is defined as the fractional contribution of each tissue types.

Consequently to obtain the optimal fractional contribution of each tissue type, the least-square error is minimized. The above equations are then solved using quadratic programming in R to obtain the optimal relative contributions of the tissue types towards the maternal cell free RNA transcripts. In the workflow, the quantity of RNA transcripts are given relative to the housekeeping genes in terms of Ct values obtained from qPCR. Therefore, the Ct value can be considered as a proxy of the measured transcript quantity. An increase in Ct value of one is similar to a two-fold change in transcript quantity. i.e. 2 raised to the power of 1. The process beings with normalizing all of the data in CT relative to the housekeeping gene, and is followed by quadratic programming.

As a proof of concept for the above scheme, different fetal tissue types (Brain, Placenta, Liver, Thymus, Lung) were mixed in equal proportions to generate a pool sample. Each fetal tissue types (Brain, Placenta, Liver, Thymus. Lung) along with the pooled sample were quantified using the same Fluidigm Biomark System to obtain the Ct values from qPCR for each fetal tissue specific transcript across all tissues and the pooled sample. These values were used to perform the same deconvolution. The resulting fetal fraction of each of the fetal tissue organs (Brain, Placenta, Liver, Thymus, Lung) was 0.109, 0.206, 0.236, 0.202 & 0.245 respectively.

Conclusion:

In summary, the panel of fetal specific cell free transcripts provides valuable biological information across different fetal tissues at once. Most particularly, the method can deduce the different relative proportions of fetal tissue-specific transcripts to total RNA, and, when considered individually, each transcript can be indicative of the apoptotic rate of the fetal tissue. Such measurements have numerous potential applications for developmental and fetal medicine. Most human fetal development studies have relied mainly on postnatal tissue specimens or aborted fetuses. Methods described herein provide quick and rapid assay of the rate of fetal tissue/organ growth or death on live fetuses with minimal risk to the pregnant mother and fetus. Similar methods may be employed to monitor major adult organ tissue systems that exhibit specific cell free RNA transcripts in the plasma.

Example 3: Additional Study for Quantification of Tissue-Specific Cell-Free RNA Exhibiting Temporal Variation During Pregnancy High-throughput methods of microarray and next-generation sequencing were used to characterize the landscape of cell-free RNA transcriptome of healthy adults and of pregnant women across all three trimesters of pregnancy and post-partum. The results confirm the study presented in Example 2, by showing that it is possible to monitor the gene expression status of many tissues and the temporal expression of certain genes can be measured across the stages of human development. The study also investigated the role of cell-free RNA in adult's suffering from neurodegenerative disorder Alzheimer's and observed a marked increase of neuron-specific transcripts in the blood of affected individuals. Thus, this study shows that the same principles of observing tissue-specific RNA to assess development can also be applied to assess the deterioration of brain tissue associated with neurological disorders.

Overview

An additional study following the guidance of Example 2 was conducted to illustrate the temporal variation among tissue-specific cell-free RNA across trimesters. FIG. 18 outlines the experimental design for this study, which examined cell-free plasma samples of 15 subjects, of which 11 were pregnant and 4 were not pregnant (2 males; 2 females). The blood samples were taken over several time-points: 1st, 2nd, and 3rd Trimester and Post-Partum. The cell-free plasma RNA were then extracted, amplified, and characterized by Affymetrix microarray, Illumina Sequencer, and quantitative PCR. For each plasma sample. ~20 million sequencing reads were generated, ~80% of which could be mapped against the human reference genome (hg 19). As the plasma RNA is of low concentration and vulnerable to degradation, contamination from the plasma DNA is a concern. To assess the quality of the sequencing library, the number of reads assigned to different regions was counted: 34% mapped to exons, 18% mapped to introns, and 24% mapped to ribosomal RNA and tRNA. Therefore, dominant portion of the reads originated from RNA transcripts rather than DNA contamination. To validate the RNA-seq measurements, all of the plasma samples were also analyzed with gene expression microarrays.

Figure 26:
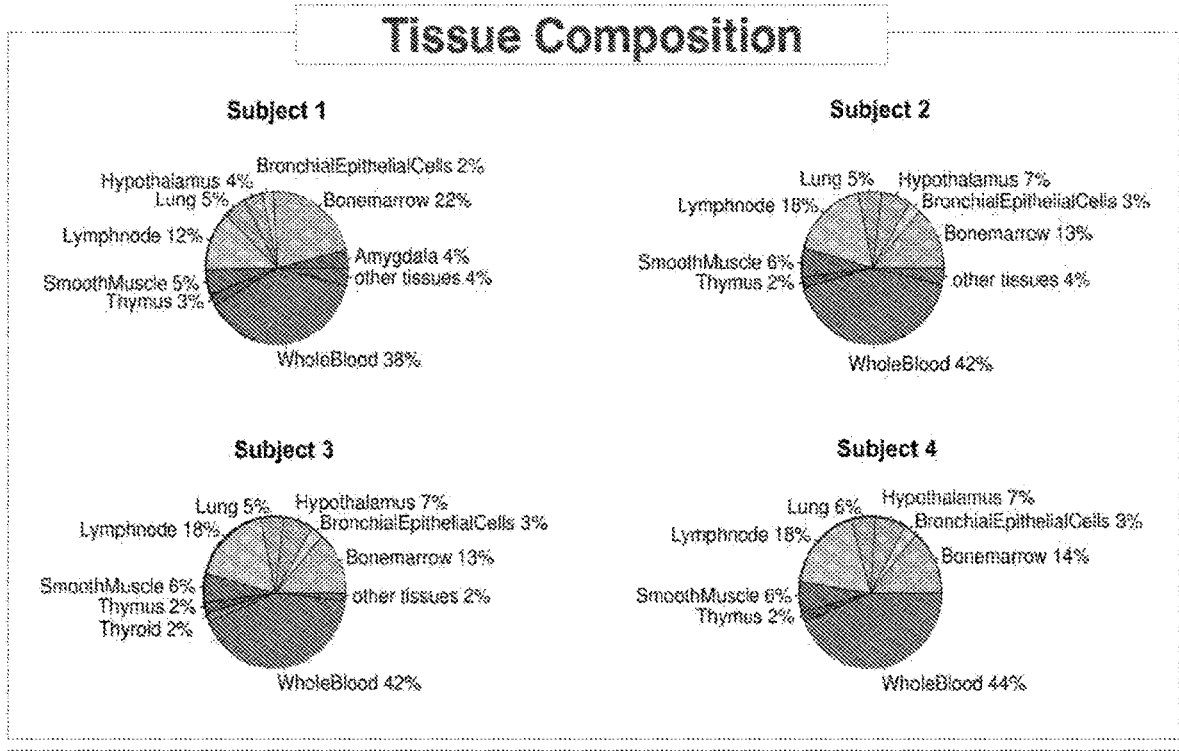
FIG. 26 illustrates decomposition of Cell-free RNA transcriptome of normal adult into their respective tissues types using microarray data and quadratic programming.

Apoptotic cells from different tissue types release their RNA into the cell-free RNA component in plasma. Each of these tissues expresses a number of genes unique to their tissue type, and the observed cell-free RNA transcriptomes can be considered as a summation of contributions from these different tissue types. Using expression data of different tissue types available in public databases, the cell-free RNA transcriptome from our four nonpregnant subjects were deconvoluted using quadratic programming to reveal the relative contributions of different tissue types (FIG. 26). These contributions identified different tissue types which are consistent among different control subjects. Whole blood, as expected, is the major contributor (~40%) toward the cell-free RNA transcriptome. Other major contributing tissue types include the bone marrow and lymph nodes. One also sees consistent contributions from smooth muscle, epithelial cells, thymus, and hypothalamus.

Results and Discussion

Within the cohort, about 100 genes were analyzed whose RNA transcripts contained paternal SNPs that were distinct from the maternal inheritance to explicitly demonstrate that the fetus contributes a substantial amount of RNA to the mother's blood (See FIG. 21). To accurately quantify and verify the relative fetal contribution, the following were genotyped: a mother and her fetus and inferred paternal genotype. The weighted average fraction of fetal-originated cell-free RNA was quantified using paternal SNPs. Cell-free RNA fetal fraction depends on gene expression and varies greatly across different genes. In general, the fetal fraction of cell-free RNA increases as the pregnancy progress and decreases after delivery. The weighted average fetal fraction started at 0.4% in the first trimester, increased to 3.4% in the second trimester, and peaked at 15.4% in the third trimester.

Although fetal RNA should be cleared after delivery, there was still 0.3% of fetal RNA as calculated, which can be attributed to background noise arising from misalignment and sequencing errors.

In addition to monitoring fetal tissue-specific mRNA, noncoding transcripts present in the cell-free compartment across pregnancy were identified. These noncoding transcripts include long noncoding RNAs (lncRNAs), as well as circular RNAs (circRNA). Additional PCR assays were designed to specifically amplify and validate the presence of these circRNA in plasma, circRNAs have recently been shown to be widely expressed in human cells and have greater stability than their linear counterparts, potentially making them reliable biomarkers for capturing transient events. Several of the circRNA species appear to be specifically expressed during different trimesters of pregnancy. The identification of these cell-free noncoding RNAs during pregnancy improve our ability to monitor the health of the mother and fetus.

There is a general increase in the number of genes detected across the different trimesters followed by a steep drop after the pregnancy. Such an increase in the number of genes detected suggests that unique transcripts are expressed specifically during particular time intervals in the developing fetus. FIGS. 18 and 19 show the heatmap of genes whose level changed over time during pregnancy, as detected by microarray. ANOVA was applied to identify genes that varied in expression in a statistically significant manner across different trimesters. An additional condition filtering for transcripts that were expressed at low levels in both the postpartum plasma of pregnant subjects and in nonpregnant controls. Using these conditions, 39 genes from RNA-seq and 34 genes from microarray were identified, of which there were 17 genes in common. Gene Ontology (GO) performed on the identified genes using Database for Annotation, Visualization and Integrated Discovery (DAVID) revealed that the identified gene list is enriched for the following GO terms: female pregnancy (Bonferroni-corrected $P=5.5\times10^{-5}$), extracellular region (corrected $P=6.6\times 10^{-3}$), and hormone activity (corrected $P=6.3\times10^{-9}$). These RNA transcripts show a general trend of having low expression postpartum and the highest expression during the third trimester. Most of these transcripts are specifically expressed in the placenta, and their levels reach a maximum in the later stages of pregnancy.

Other nonplacental transcripts that share similar temporal trends. Two such significant transcripts were RAB6B and MARCH2, which are known to be expressed specifically in CD71+ erythrocytes. Erythrocytes enriched for CD71+ have been shown to contain fetal hemoglobin and are interpreted to be of fetal origin. The presence of transcripts with known specificity to different fetal tissue types reflects the fact that the cell-free transcriptome during the period of pregnancy can be considered as a summation of transcriptomes from various different fetal tissues on top of a maternal background.

Figure 22:
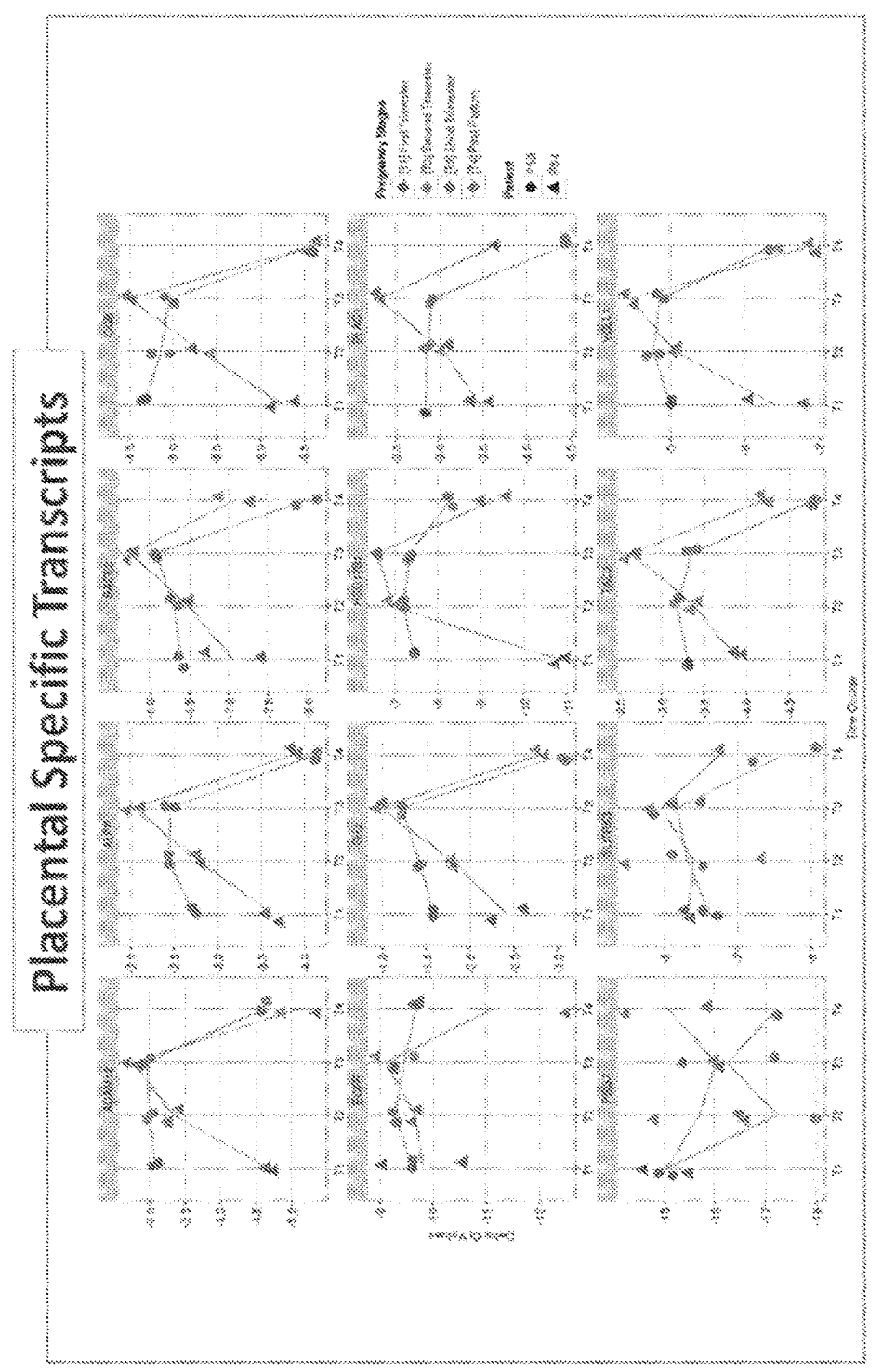
FIG. 22 identifies placental specific transcripts measured by qPCR in the experimental design of FIG. 18.
Figure 23:
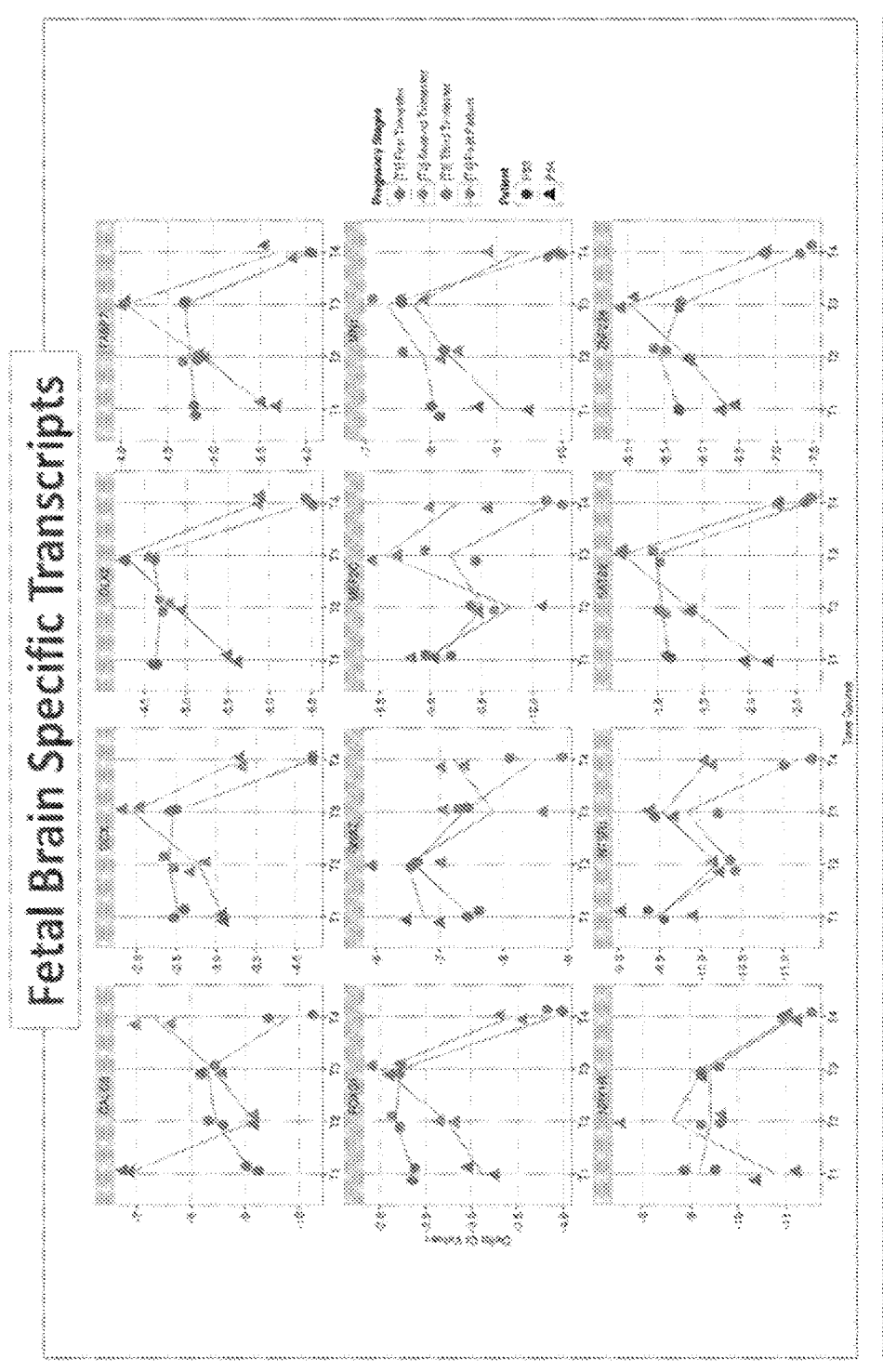
FIG. 23 identifies fetal brain specific transcripts measured byq.
Figure 24:
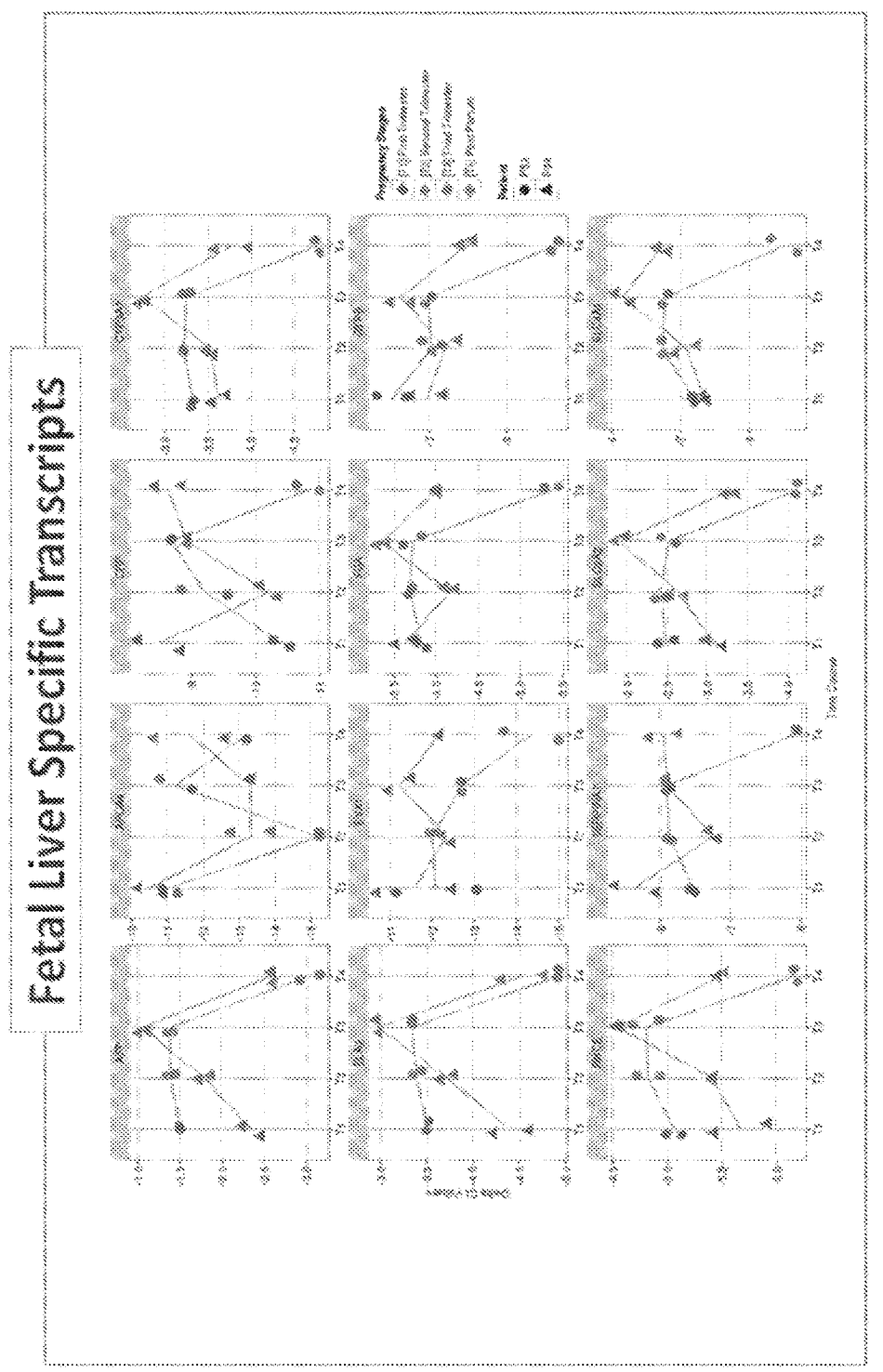
FIG. 24 identifies fetal liver specific transcripts measured by qPCR.

This analysis detected the presence of numerous transcripts that are specifically expressed in several other fetal tissues, although the available sequencing depth resulted in limited concordance between samples. To verify the presence of these and other potential fetal tissue-specific transcripts, a panel of fetal tissue-specific transcripts was devised for detailed quantification using the more sensitive method of quantitative PCR (qPCR). Three main sources were focused on, which are of interest to fetal neurodevelopment and metabolism: placenta, fetal brain, and fetal liver. In FIGS. 22-24, the levels of these groups of fetal tissue-specific transcripts at different trimesters were systematically compared to the level seen in maternal serum after delivery. To illustrate the temporal trends, housekeeping genes were used as a baseline, and $\Delta Ct$ analysis was applied to find the level of relative expression these fetal tissue-specific transcripts with respect to the housekeeping genes. Many of these tissue-specific transcripts expressed at substantially higher levels during the pregnancy compared with postpartum. There was a general trend of an increase in the quantity of these transcripts across advancing gestation.

The placental qPCR assay focused on genes that are known to be highly expressed in the placenta, many of which encode for proteins that have been shown to be present in the maternal blood. The serum levels of these proteins are known to be involved in pregnancy complications such as preeclampsia and premature births. Examples in our panel includes ADAM12, which encodes for disintegrin, and metalloproteinase domain-containing protein 12. These proteinases are highly expressed in human placenta and are present at high concentrations in maternal serum as early as the first trimester. ADAM12 serum concentrations are known to be significantly reduced in pregnancies complicated by fetal trisomy 18 and trisomy 21 and may therefore be of potential use in conjunction with cell-free DNA for the detection of chromosomal abnormalities. Similarly, placental alkaline phosphatase, encoded by the ALPP gene, is a tissue-specific isoform expressed increasingly throughout pregnancy until term in the placenta. It is anchored to the plasma membrane of the syncytiotrophoblast and to a lesser extent of cytotrophoblastic cells. This enzyme is also released into maternal serum, and variations of its concentration are related with several clinical disorders such as preterm delivery. Another gene in the panel, BACE2, encoded the β site APP-cleaving enzyme, which generates amyloid-β protein by endoproteolytic processing. Brain deposition of amyloid-β protein is a frequent complication of Down syndrome patients, and BACE-2 is known to be overexpressed in Down syndrome.

Other transcripts in our placental assay are known to be transcribed at high levels in the placenta, and levels of these mRNAs are important for normal placental function and development in pregnancy. TAC3 is mainly expressed in the placenta and is significantly elevated in preeclamptic human placentas at term. Similarly, PLAC1 is essential for normal placental development. PLAC1 deficiency results in a hyperplastic placenta, characterized by an enlarged and dysmorphic junctional zone. An increase in cell-free mRNA of PLAC1 has been suggested to be correlated with the occurrence of preeclampsia.

On the fetal liver tissue-specific panel, one of the characterized transcripts is AFP. AFP encodes for α-fetoprotein and is transcribed mainly in the fetal liver. AFP is the most abundant plasma protein found in the human fetus. Clinically, AFP protein levels are measured in pregnant women in either maternal blood or amniotic fluid and serve as a screening marker for fetal aneuploidy, as well as neural tube and abdominal wall defects. Other fetal liver-specific transcripts that were characterized are highly involved in metabolism. An example is fetal liver-specific monooxygenase CYP3A7, which catalyzes many reactions involved in synthesis of cholesterol and steroids and is responsible for the metabolism of more than 50% of all clinical pharmaceuticals. In drug-treated diabetic pregnancies in which glucose levels in the woman are uncontrolled, neural tube and cardiac defects in the early developing brain, spine, and heart depend on functional GLUT2 carriers, whose transcripts are well characterized in the panel. Mutations in this gene results in Fanconi-Bickel syndrome, a congenital defect of facilitative glucose transport. Monitoring of fetal liver-specific transcripts during the drug regime may enable analysis of the fetuses' response to drug therapy that the mother is undergoing.

Example 4: Deconvolution of Adult Cell-Free Transcriptome

Overview:

The plasma RNA profiles of 4 healthy, normal adults were analyzed. Based on the gene expression profile of different tissue types, the methods described quantify the relative contributions of each tissue type towards the cell-free RNA component in a donor's plasma. For quantification, apoptotic cells from different tissue types are assumed to release their RNA into the plasma. Each of these tissues expressed a specific number of genes unique to the tissue type, and the observed cell-free RNA transcriptome is a summation of these different tissue types.

Study Design and Methods:

To determine the contribution of tissue-specific transcripts to the cell-free adult transriptome, a list of known tissue-specific genes was prepared from known literature and databases. Two database sources were utilized: Human U133A/GNF1H Gene Atlas and RNA-Seq Atlas. Using the raw data from these two database, tissue-specific genes were identified by the following method. A template-matching process was applied to data obtained from the two databases for the purpose of identifying tissue-specific gene. The list of tissue specific genes identified by the method is provided in Table 1 below. The specificity and sensitivity of the panel is constrained by the number of tissue samples in the database. For example, the Human U133A/GNF1H Gene Atlas dataset includes 84 different tissue samples, and a panel's specificity from that database is constrained by the 84 sample sets. Similarly, for the RNA-seq atlas, there are 11 different tissue samples and specificity is limited to distinguishing between these 11 tissues. After obtaining a list of tissue-specific transcripts from the two databases, the specificity of these transcripts was verified with literature as well as the TisGED database.

The adult cell-free transcriptome can be considered as a summation of the tissue-specific transcripts obtained from the two databases. To quantitatively deduce the relative proportions of the different tissues in an adult cell-free transcriptome, quadratic programming is performed as a constrained optimization method to deduce the relative optimal contributions of different organs/tissues towards the cell free-transcriptome. The specificity and accuracy of this process is dependent on the table of genes (Table 2 below) and the extent by which that they are detectable in RNA-seq and microarray.

Subjects: Plasma samples were collected from 4 healthy, normal adults.

Initial Results:

Deconvolution of our adult cell-free RNA transcriptome from microarray using the above methods revealed the relative contributions of the different tissue and organs are tabulated in FIG. 13.

FIG. 13 shows that the normal cell free transcriptome for adults is consistent across all 4 subjects. The relative contributions between the 4 subjects do not differ greatly, suggesting that the relative contributions from different tissue types are relatively stable between normal adults. Out of the 84 tissue types available, the deduced optimal major contributing tissues are from whole blood and bone marrow.

An interesting tissue type contributing to circulating RNA is the hypothalamus. The hypothalamus is bounded by specialized brain regions that lack an effective blood-brain barrier; the capillary endothelium at these sites is fenestrated to allow free passage of even large proteins and other molecules which in our case we believed that RNA transcripts from apoptotic cells in that region could be released into the plasma cell free RNA component.

The same methods were performed on the subjects using RNA-seq. The results described herein are limited due to the amount of tissue-specific RNA-Seq data available. However, it is understood that tissue-specific data is expanding with the increasing rate of sequencing of various tissue rates, and future analysis will be able to leverage those datasets. For RNA-seq data (as compared to microarray), whole blood nor the bone marrow samples are not available. The cell free transcriptome can only be decomposed to the available 11 different tissue types of RNA-seq data, of which, only relative contributions from the hypothalamus and spleen were observed, as shown in FIG. 14.

Figure 15:
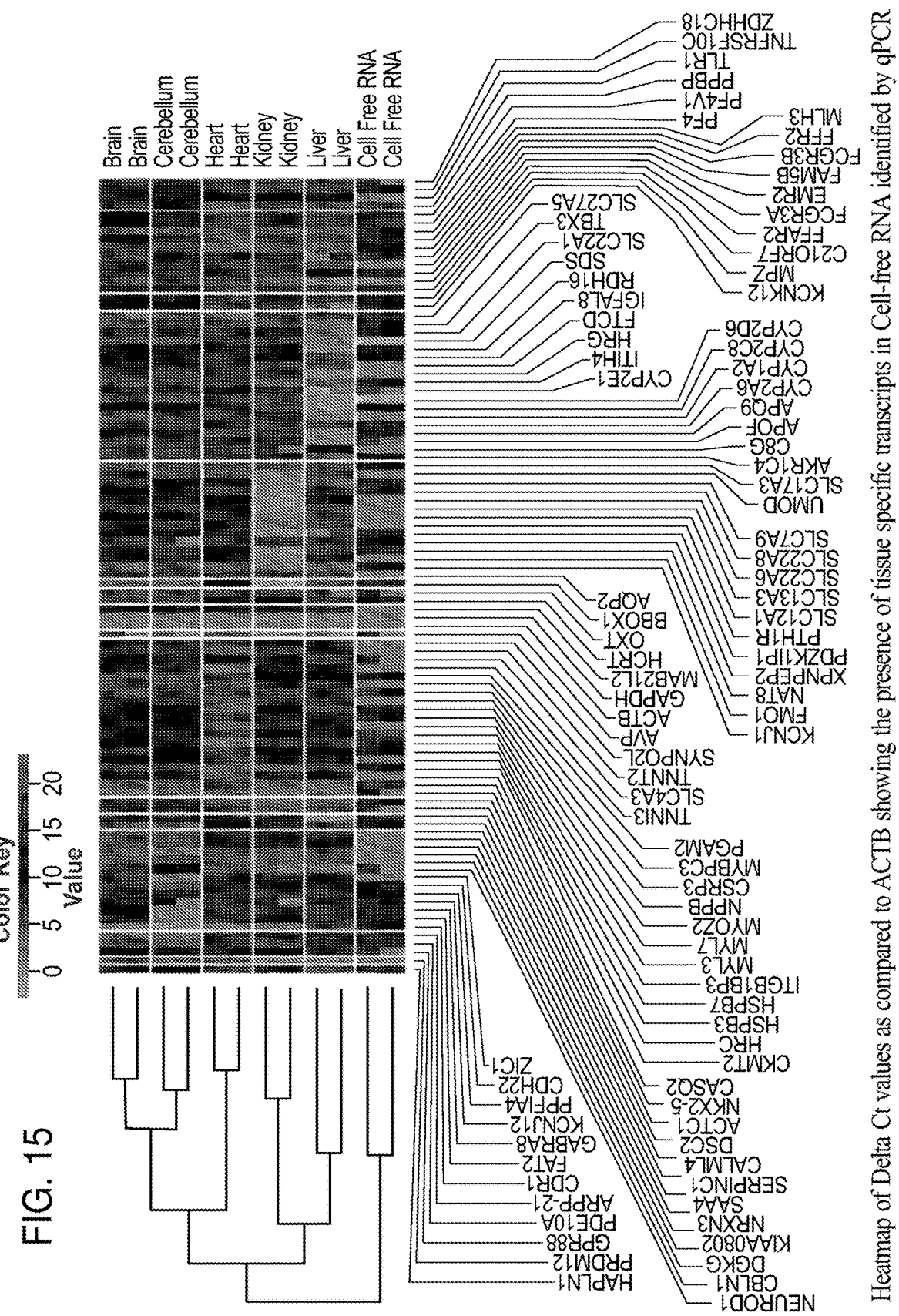
FIG. 15 shows a heat map of the tissue specific transcripts of Table 2 of Example 3, being detectable in the cell free RNA.

A list of 84 tissue-specific genes (as provided in Table 2) was further selected for verification with qPCR. The Fluidigm BioMark Platform was used to perform the qPCR on RNA derived from the following tissues: Brain, Cerebellum, Heart, Kidney, Liver and Skin. Similar qPCR workflow was applied to the cell free RNA component as well. The delta ct values by comparing with the housekeeping genes: ACTB was plotted in the heatmap format in FIG. 15, which shows that these tissue specific transcripts are detectable in the cell free RNA.

Tables for Example 4

The following table lists the tissue-specific genes for Example 4 that was obtained using raw data from the Human U133A/GNF1H Gene Atlas and RNA-Seq Atlas databases.

TABLE 1

List of Tissue-Specific Genes Determined by Deconvolution of Adult Transcriptome

| Gene | Tissue |
| --- | --- |
| A4GALT | Uterus Corpus |
| A4GNT | Superior Cervical Ganglion |
| AADAC | small intestine |
| AASS | Ovary |
| ABCA12 | Tonsil |
| ABCA4 | retina |
| ABCB4 | CD19 B cells neg. sel. |
| ABCB6 | CD71 Early erythroid |
| ABCB7 | CD71 Early erythroid |
| ABCC2 | Pancreatic Islet |
| ABCC3 | Adrenal Cortex |
| ABCC9 | Dorsal Root Ganglion |
| ABCF3 | Adrenal gland |
| ABCG1 | Lung |
| ABCG2 | CD71 Early erythroid |
| ABHD4 | Adipocyte |
| ABHD5 | Whole Blood |
| ABHD6 | pineal night |
| ABHD8 | Whole Brain |
| ABO | Heart |
| ABT1 | X721 B lymphoblasts |
| ABTB2 | Placenta |
| ACAA1 | Liver |
| ACACB | Adipocyte |
| ACAD8 | Kidney |
| ACADL | Thyroid |

TABLE 1-continued

List of Tissue-Specific Genes Determined
by Deconvolution of Adult Transcriptome

| Gene | Tissue |
|---|---|
| ACADS | Liver |
| ACADSB | Fetal liver |
| ACAN | Trachea |
| ACBD4 | Liver |
| ACCN3 | Prefrontal Cortex |
| ACE2 | Testis Germ Cell |
| ACHE | CD71 Early erythroid |
| ACLY | Adipocyte |
| ACOT1 | Adipocyte |
| ACOX2 | Liver |
| ACP2 | Liver |
| ACP5 | Lung |
| ACP6 | CD34 |
| ACPP | Prostate |
| ACR | Testis Interstitial |
| ACRV1 | Testis Interstitial |
| ACSBG2 | Testis Interstitial |
| ACSF2 | Kidney |
| ACSL4 | Fetal liver |
| ACSL5 | Small intestine |
| ACSL6 | GD71 Early erythroid |
| ACSM3 | Leukemia chronic myelogenous K562 |
| ACSM5 | Liver |
| ACSS3 | Adipocyte |
| ACTA1 | Skeletal Muscle |
| ACTC1 | Heart |
| ACTG1 | CD71 Early Erythroid |
| ACTL7A | Testis interstitial |
| ACTL7B | Testis interstitial |
| ACTN3 | Skeletal Muscle |
| ACTR8 | Superior Cervical Ganglion |
| ADA | Leukemia lymphoblastic MOLT 4 |
| ADAM12 | Placenta |
| ADAM17 | CD33 myeloid |
| ADAM2 | Testis interstitial |
| ADAM21 | Appendix |
| ADAM23 | Thalamus |
| ADAM28 | CD19 Bcells neg. sel. |
| ADAM30 | Testis Germ Cell |
| ADAM5P | Testis Interstitial |
| ADAM7 | Testis Leydig cell |
| ADAMTS12 | Atrioventricular Node |
| ADAMTS20 | Appendix |
| ADAMTS3 | CD105 Endothelial |
| ADAMTS8 | Lung |
| ADAMTS9 | Dorsal Root Ganglion |
| ADAMTSL2 | Ciliary Ganglion |
| ADAMTSL3 | retina |
| ADAMTSL4 | Atrioventricular Node |
| ADARB2 | Skeletal Muscle |
| ADAT1 | CD71 Early Erythroid |
| ADCK4 | Ciliary Ganglion |
| ADCY1 | Fetal brain |
| ADCY9 | Lung |
| ADCYAP1 | Pancreatic Islet |
| ADH7 | Tongue |
| ADIPOR1 | Bone marrow |
| ADM2 | Pituitary |
| ADORA3 | Olfactory Bulb |
| ADRA1D | Skeletal Muscle |
| ADRA2A | Lymph node |
| ADRA2B | Superior Cervical Ganglion |
| ADRB1 | pineal night |
| AFFF3 | Trigeminal ganglion |
| AFF4 | Testis Intersitial |
| AGPAT2 | Adipocyte |
| AGPAT3 | CD33 Myeloid |
| AGPAT4 | CD71 Early Erythroid |
| AGPS | Testis interstitial |
| AGR2 | Trachea |
| AGRN | Colorectal adenocarcinoma |
| AGRP | Superior Cervical Ganglion |
| AGXT | Liver |
| AIFM1 | X721 B lymphoblasts |
| AIM2 | CD19 Bcells neg. sel. |

TABLE 1-continued

List of Tissue-Specific Genes Determined
by Deconvolution of Adult Transcriptome

| Gene | Tissue |
|---|---|
| AJAP1 | BDCA4 Dentritic Cells |
| AKAP10 | CD33 myeloid |
| AKAP3 | Testis interstitial |
| AKAP6 | Medulla oblongata |
| AKAP7 | Fetal brain |
| AKAP8L | CD71 Early Erythroid |
| AKR1C4 | Liver |
| AKR7A3 | Liver |
| AKT2 | Thyroid |
| ALAD | CD71 Early Erythroid |
| ALDH3B2 | Tongue |
| ALDH6A1 | Kidney |
| ALDH7A1 | Ovary |
| ALDOA | Skeletal Muscle |
| ALG12 | CD4 T cells |
| ALG13 | CD19 Bcells neg. sel. |
| ALG3 | Liver |
| ALOX12 | Whole Blood |
| ALOX1212 | Tonsil |
| ALOX15B | Prostate |
| API | small intestine |
| ALPK3 | Skeletal Muscle |
| ALPL | Whole Blood |
| ALPP | Placenta |
| ALPPL2 | Placenta |
| ALX1 | Superior Cervical Ganglion |
| ALX4 | Superior Cervical Ganglion |
| AMBNI | pineal day |
| AMDHD2 | BDCA4 Dentritic Cells |
| AMEN | Subthalamic Nucleus |
| AMHR2 | Heart |
| AMPD1 | Skeletal Muscle |
| AMPD2 | pineal night |
| AMPD3 | CD71 Early Erythroid |
| ANAPC1 | X721 B lymphoblasts |
| ANG | Liver |
| ANGEL2 | CD8 T cells |
| ANGPT1 | CD35 |
| ANGPT2 | Ciliary Ganglion |
| ANGPTL2 | Uterus Corpus |
| ANGPTL3 | Fetal liver |
| ANK1 | CD71 Early Erythroid |
| ANKFY1 | CD8 T cells |
| ANKH | Cerebellum Peduncles |
| ANKLE2 | Testis |
| ANKRD1 | Skeletal Muscle |
| ANKRD2 | Skeletal Muscle |
| ANKRD34C | Thalamus |
| ANKRD5 | Skeletal Muscle |
| ANKRD53 | Skeletal Muscle |
| ANKRD57 | Bronchial Epithelial Cells |
| ANKS1B | Superior Cervical Ganglion |
| ANIXR1 | Uterus Corpus |
| ANXA13 | small intestine |
| ANXA2P1 | Bronchial Epithelial Cells |
| ANXA2P3 | Bronchial Epithelial Cells |
| AOC:2 | retina |
| AP1G1 | Testis Germ Cell |
| AP1M2 | Kidney |
| AP351 | Heart |
| APBA1 | Dorsal Root Ganglion |
| APBBIIP | Whole Blood |
| APBB2 | Superior Cervical Ganglion |
| APC | Fetal brain |
| APEX2 | Colorectal adenocarcinoma |
| AMP | Trachea |
| AP0A1 | Liver |
| AP0A4 | small intestine |
| APO348R | Whole Blood |
| APOBEC1 | small intestine |
| APOBEC2 | Skeletal Muscle |
| APOBEC313 | Colorectal adenocarcinoma |
| APOC4 | Liver |
| APOF | Liver |
| APOL5 | Bone marrow |

TABLE 1-continued

List of Tissue-Specific Genes Determined
by Deconvolution of Adult Transcriptome

| Gene | Tissue |
|------|--------|
| APOOL | Superior Cervical Ganglion |
| AQP2 | Kidney |
| AQP5 | Testis Interstitial |
| AQP7 | Adipocyte |
| AR | Liver |
| ARCN1 | Trigeminal Ganglion |
| ARFGAP1 | Lymphoma burkitts Raji |
| ARG1 | Fetal liver |
| ARHGAPDA | Trigeminal Ganglion |
| ARHGAP19 | Olfactory Bulb |
| ARHGAP22 | CD36 |
| ARHGAP28 | Testis Interstitial |
| ARHGAP6 | Prostate |
| ARHGE1,1 | CD4 T cells |
| ARHGEF5 | Pancreas |
| ARHGEF7 | Thymus |
| AR1D3A | Placenta |
| ARID313 | X721 B lymphoblasts |
| ARLES | Uterus Corpus |
| ARIVIC4 | Superior Cervical Ganglion |
| ARN1C8 | CD71 Early Erythroid |
| ARIVICX5 | small intestine |
| ARR3 | retina |
| ARSA | Liver |
| ARO | Superior Cervical Ganglion |
| ARSE | Liver |
| ARSF | Globus Pallidus |
| ART1 | Cardiac Myocytes |
| ART3 | Testis |
| ART4 | CD71 Early Erythroid |
| ASB1 | Trigeminal Ganglion |
| ASB7 | Globus Pallidus |
| ASB8 | Superior Cervical Ganglion |
| ASCC2 | CD71 Early Erythroid |
| ASCL2 | Superior Cervical Ganglion |
| ASCL3 | Superior Cervical Ganglion |
| ASF1A | CD71 Early Erythroid |
| ASIP | BDCA4 Dentritic Cells |
| ASL | Liver |
| ASPN | Uterus |
| ASPSCR1 | Colorectal adenocarcinoma |
| ASTE1 | CD8 T cells |
| ASTN2 | pineal day |
| ATF5 | Liver |
| ATG4A | CD71 Early Erythroid |
| NMI | CD14 Monocytes |
| ATN1 | Prefrontal Cortex |
| ATOH1 | Superior Cervical Ganglion |
| ATP10A | CD56 NK Cells |
| ATP1OD | Placenta |
| ATP11A | Superior Cervical Ganglion |
| ATP12A | Trachea |
| ATP13A3 | Smooth Muscle |
| ATP1B3 | Adrenal Cortex |
| ATP2C2 | Colon |
| ATP4A | Adrenal gland |
| ATP4B | Parietal Lobe |
| ATPSG1 | Heart |
| ATP5G3 | Heart |
| ATPS12 | Superior Cervical Ganglion |
| ATP5V0A2 | CD37 |
| ATP6V1B1 | Kidney |
| ATP7A | CD71 Early Erythroid |
| ATRIP | CD14 Monocytes |
| ATXN3L | Superior Cervical Ganglion |
| AIXN711 | Skeletal Muscle |
| AURKC | Testis Seminiferous Tubule |
| AVM | Bronchial Epithelial Cells |
| AWL. | Dorsal Root Ganglion |
| AVP | Hypothalamus |
| AMN1 | CD56 NK Cells |
| AXL | Cardiac Myocytes |
| AZI1 | CD71 Early Erythroid |
| B3GAINT1 | Amygdala |
| B3GALT5 | CD105 Endothelial |

TABLE 1-continued

List of Tissue-Specific Genes Determined
by Deconvolution of Adult Transcriptome

| Gene | Tissue |
|------|--------|
| B3GNT2 | CD71 Early Erythroid |
| B3GNT3 | Placenta |
| B3GNTL1 | CD38 |
| BAAT | Liver |
| BACH2 | Lymphoma burkitts Daudi |
| BAD | Whole Brain |
| BAG2 | Uterus |
| BAG4 | Superior Cervical Ganglion |
| BAI1 | Cingulate Cortex |
| BAIAP2 | Liver |
| BAMP2L2 | Superior Cervical Ganglion |
| BAMW | Colorectal adenocarcinoma |
| BANK1 | CD19 Bcells neg. sel. |
| BARD1 | X721 B lymphoblasts |
| BARX1 | Atrioventricular Node |
| BATF3 | X721 B lymphoblasts |
| BBOX1 | Kidney |
| BBS4 | pineal day |
| BCAM | Thyroid |
| BCAR3 | Placenta |
| BCAS3 | X721 B lymphoblasts |
| BCKDK | Liver |
| BCL10 | Colon |
| BCL2L1 | CD71 Early Erythroid |
| BCL2L10 | Trigeminal Ganglion |
| BCL2L13 | pineal day |
| BCL2L14 | Testis |
| BCL3 | Whole Blood |
| BDH1 | Liver |
| BDKRB1 | Smooth Muscle |
| BDKRB2 | Smooth Muscle |
| BDNF | Smooth Muscle |
| BECN1 | Ciliary Ganglion |
| BEST1 | retina |
| BET1L | Superior Cervical Ganglion |
| BHLHB9 | pineal night |
| B1RC3 | CD19 Bcells neg. sel. |
| BLK | CD19 Bcells neg. sel. |
| BIVRA | CD105 Endothelial |
| BMP1 | Placenta |
| BMP2K | CD71 Early Erythroid |
| BMP3 | Temporal Lobe |
| BWIPS | Trigeminal Ganglion |
| BMP8A | Fetal Thyroid |
| BMP86 | Superior Cervical Ganglion |
| BMPR1B | Skeletal Muscle |
| BNC1 | Bronchial Epithelial Cells |
| BNC2 | Uterus |
| BNIP3L | CD71 Early Erythroid |
| BOK | Thalamus |
| BPHL | Kidney |
| BPI | Bone marrow |
| BPY2 | Adrenal gland |
| BRAF | Superior Cervical Ganglion |
| BRAP | Testis Interstitial |
| BRE | Adrenal gland |
| BRS3 | Skeletal Muscle |
| BRSK2 | Cerebellum Peduncles |
| BSDC1 | CD71 Early Erythroid |
| 3TBD2 | Prefrontal Cortex |
| BTD | Superior Cervical Ganglion |
| BTN2A3 | Appendix |
| BTN3A1 | CD8 T cells |
| BTRC | CD71 Early Erythroid |
| BUBI | X721 B lymphoblasts |
| BYSL | Leukemia chronic Myelogenous K563 |
| C10orf118 | Testis Leydig Cell |
| C10orf 119 | CD33 Myeloid |
| C10orf28 | Superior Cervical Ganglion |
| C10orf57 | Ciliary Ganglion |
| C10orf72 | Adrenal Cortex |
| C10orf76 | CD19 Bcells neg. sel. |
| C10orf81 | Dorsal Root Ganglion |
| C1Oorf84 | Superior Cervical Ganglion |
| C10orf88 | Testis Seminiferous Tubule |

TABLE 1-continued

List of Tissue-Specific Genes Determined
by Deconvolution of Adult Transcriptome

| Gene | Tissue |
| --- | --- |
| C10orf95 | Superior Cervical Ganglion |
| C11orf41 | Fetal brain |
| C11orf48 | Adipocyte |
| C11orf57 | Appendix |
| C11orf67 | Skeletal Muscle |
| C11orf71 | Thyroid |
| C11orf80 | Leukemia lymphoblastic MOLT 5 |
| C12orf4 | CD71 Early Erythroid |
| C12orf43 | Whole Brain |
| C12orf47 | CD8 T cells |
| C12orf49 | CD56 NK Cells |
| C13orf23 | Placenta |
| C13orf27 | Testis Leydig Cell |
| C13orf34 | CD71 Early Erythroid |
| C14orf106 | CD33 Myeloid |
| C14orf118 | Superior Cervical Ganglion |
| Cl4orf138 | CD19 Bcells neg. sel. |
| C14orf162 | Cerebellum |
| C14orf169 | Testis |
| C14orf56 | Superior Cervical Ganglion |
| C15orf2 | Cerebellum |
| C15orf29 | Fetal brain |
| C15orf39 | Whole Blood |
| C15orf44 | Testis |
| C15orf5 | Superior Cervical Ganglion |
| C16orf3 | Dorsal Root Ganglion |
| Cl6orfS3 | pineal day |
| C16orf59 | CD71 Early Erythroid |
| ClCorf68 | Testis |
| C16orf71 | Testis Seminiferous Tubule |
| C17orf42 | X721 B lymphoblasts |
| C1lot153 | Dorsal Root Ganglion |
| C17orfS9 | Dorsal Root Ganglion |
| Cl7orf68 | CD8 T cells |
| C17orf73 | Cardiac Myocytes |
| C17orf80 | Testis Germ Cell |
| C1iorf81 | Testis Interstitial |
| C17orf85 | BDCA4 Dentric Cells |
| C17orf88 | Superior Cervical Ganglion |
| C19orf29 | Leukemia chronic Myelogenous K564 |
| C19orf61 | Leukemia lymphoblastic MOLT 6 |
| C1GALT1C1 | Superior Cervical Ganglion |
| C1orf103 | Leukemia chronic Myelogenous K565 |
| C1orf105 | Testis Interstitial |
| C1orf106 | small intestine |
| Clorfl14 | Testis Interstitial |
| C1orf135 | Testis |
| Clorf14 | Testis Leydig Cell |
| Clorf156 | CD19 Bcells neg. sel. |
| Clorf175 | Testis Interstitial |
| Clorf222 | Testis |
| Clorf25 | CD71 Early Erythroid |
| Clorf27 | pineal night |
| Clorf35 | CD71 Early Erythroid |
| C1orf50 | Testis |
| C1orf66 | Leukemia chronic Myelogenous K566 |
| C1orf68 | Liver |
| C1orf89 | Atrioventricular Node |
| C1orf9 | CD71 Early Erythroid |
| CIQINF1 | Smooth Muscle |
| CIQINF3 | Spinal Cord |
| C2 | Liver |
| C20oRd191 | Superior Cervical Ganglion |
| C20orf29 | Superior Cervical Ganglion |
| C21orf45 | CD105 Endothelial |
| C2lorf7 | Whole Blood |
| C21orf91 | Testis Interstitial |
| C22orf24 | Superior Cervical Ganglion |
| C22126 | Ciliary Ganglion |
| C22orf30 | Trigeminal Ganglion |
| C22orf31 | Uterus Corpus |
| C2CD2 | Adrenal Cortex |
| C2orf18 | Cerebellum |
| C2orf34 | pineal day |
| C2orf42 | Testis |

TABLE 1-continued

List of Tissue-Specific Genes Determined
by Deconvolution of Adult Transcriptome

| Gene | Tissue |
| --- | --- |
| C2orf43 | X721 B lymphoblasts |
| C2orf54 | Trigeminal Ganglion |
| C3AR1 | CD14 Monocytes |
| C3orf37 | Lymphoma burkitts Daudi |
| C3orf64 | pineal day |
| C4orf19 | Placenta |
| C4orf23 | Superior Cervical Ganglion |
| C4orf6 | Superior Cervical Ganglion |
| C5 | Fetal liver |
| CSAR1 | Whole Blood |
| C5orf23 | CD39 |
| C5orf28 | Thyroid |
| C5orf4 | CD71 Early Erythroid |
| CSorf42 | Superior Cervical Ganglion |
| C5orf103 | Testis Interstitial |
| C6orf105 | Colon |
| C5orf108 | Lymphoma burkitts Raji |
| C6orf124 | Fetal brain |
| C6orf162 | Pituitary |
| C5orf208 | Superior Cervical Ganglion |
| C6orf25 | Superior Cervical Ganglion |
| C6orf27 | Superior Cervical Ganglion |
| C6orf35 | Appendix |
| C6orf54 | Skeletal Muscle |
| C6orf64 | Testis |
| C7orf10 | Bronchial Epithelial Cells |
| C7orf25 | Superior Cervical Ganglion |
| C7orfS8 | Leukemia chronic Myelogenous K567 |
| C8G | Liver |
| C8orf17 | Superior Cervical Ganglion |
| CBorf41 | Leukemia lymphoblastic MOLT 7 |
| C9 | Liver |
| C9orf116 | Testis |
| C9orf27 | Trigeminal Ganglion |
| C9orf3 | Uterus |
| C9orf38 | Superior Cervical Ganglion |
| C9orf40 | CD71 Early Erythroid |
| C9orf46 | Bronchial Epithelial Cells |
| C9orf68 | Skeletal Muscle |
| C9orf86 | CD71 Early Erythroid |
| C9orf9 | Testis Interstitial |
| CAI | CD71 Early Erythroid |
| CAI2 | Kidney |
| CA3 | Thyroid |
| CM | Lung |
| CASA | Liver |
| CAB | Superior Cervical Ganglion |
| CA6 | Salivary gland |
| CA7 | Atrioventricular Node |
| CA9 | Skin |
| CAB391 | Prostate |
| CARPS | retina |
| CABYR | Testis Interstitial |
| CACNA1B | Superior Cervical Ganglion |
| CACNA1D | Pancreas |
| CACNA1E | Superior Cervical Ganglion |
| CACNA1F | pineal day |
| CACNA1G | Cerebellum |
| CACNA1H | Adrenal Cortex |
| CACNA1I | Prefrontal Cortex |
| CACNA1S | Skeletal Muscle |
| CACNA2D1 | Superior Cervical Ganglion |
| CACNA2D3 | CD14 Monocytes |
| CACNB1 | Skeletal Muscle |
| CACNAG2 | Cerebellum Peduncles |
| CACNG4 | Skeletal Muscle |
| CADM4 | Prostate |
| CADPS2 | Cerebellum Peduncles |
| CALCA | Dorsal Root Ganglion |
| CALCRL | Fetal lung |
| CALM LS | Skin |
| CAMK1G | Whole Brain |
| CAMK4 | Testis Intersitial |
| CAMTA2 | pineal night |
| CAN D2 | Heart |

TABLE 1-continued

List of Tissue-Specific Genes Determined
by Deconvolution of Adult Transcriptome

| Gene | Tissue |
| --- | --- |
| CANT1 | Prostate |
| CAPNS | Colon |
| CAPN6 | Placenta |
| CAPN7 | Superior Cervical Ganglion |
| CARD14 | CD71 Early Erythroid |
| CASP10 | CD4 T cells |
| CASP2 | Leukemia lymphoblastic MOLT 8 |
| CASP9 | Adrenal Cortex |
| CASQ2 | Heart |
| CASR | Kidney |
| CASS4 | Cingulate Cortex |
| CAVISPERB | Superior Cervical Ganglion |
| CAV3 | Superior Cervical Ganglion |
| CBFA2T3 | BDCA4 Dentritic Cells |
| CBL | Testis Germ Cell |
| CBLC | Bronchial Epithelial Cells |
| CBX2 | Trachea |
| CCBP2 | Superior Cervical Ganglion |
| CCDC132 | Trigeminal Ganglion |
| CCDC19 | Testis Intersitial |
| CCDC21 | CD71 Early Erythroid |
| CCDC25 | CD33 Myeloid |
| CCDC28B | Lymphoma burkitts Raji |
| CCDC33 | Superior Cervical Ganglion |
| CCDC41 | CD40 |
| CCDC46 | Testis Intersitial |
| CCDC51 | Leukemia promyelocytic HL60 |
| CCDC6 | Colon |
| CCDC64 | CD8 T cells |
| CCDC68 | Fetal lung |
| CCDC76 | CD8 T cells |
| CCDC81 | Superior Cervical Ganglion |
| CCDC87 | Testis |
| CCDC88A | BDCA4 Dentritic Cells |
| CCDC88C | CD56 NK Cells |
| CCDC99 | Leukemia lymphoblastic MOLT 9 |
| CCHCR1 | Testis |
| CCIN | Testis Intersitial |
| CCKAR | Uterus Corpus |
| CCL11 | Smooth Muscle |
| CCL13 | small intestine |
| CCL18 | Thymus |
| CCL2 | Smooth Muscle |
| CCL21 | Lymph node |
| CCL22 | X721 B lymphoblasts |
| CCL 24 | Uterus Corpus |
| CCL27 | Skin |
| CCL3 | CD33 Myeloid |
| CCL4 | CD56 NK Cells |
| CCL7 | Smooth Muscle |
| CCND1 | Colorectal adenocarcinoma |
| CCNF | CD71 Early Erythroid |
| CCNJ | Ciliary Ganglion |
| CCNJL | Atrioventricular Node |
| CCNL2 | CD4 T cells |
| CCNO | Testis |
| CCR10 | X721 B lymphoblasts |
| CCR3 | Whole Blood |
| CCR5 | CD8 T cells |
| CCR6 | CD19 Bcells neg. sel. |
| CCRL2 | CD71 Early Erythroid |
| CCRN4L | Appendix |
| CCS | CD71 Early Erythroid |
| CCT4 | Superior Cervical Ganglion |
| CD160 | CD56 NK Cells |
| CD180 | CD19 Bcells neg. sel. |
| CD1C | Thymus |
| CD207 | Appendix |
| CD209 | Lymph node |
| CD22 | Lymphoma burkitts Raji |
| CD226 | Superior Cervical Ganglion |
| CD244 | CD56 NK Cells |
| CD248 | Adipocyte |
| CD320 | Heart |
| CD3EAP | Dorsal Root Ganglion |

TABLE 1-continued

List of Tissue-Specific Genes Determined
by Deconvolution of Adult Transcriptome

| Gene | Tissue |
| --- | --- |
| CD3G | Thymus |
| CD4 | BDCA4 Dentritic Cells |
| CD40 | Lymphoma burkitts Raji |
| CD4OLG | CD41 |
| CD5L | CD105 Endothelial |
| CD799 | Lymphoma burkitts Raji |
| CD80 | X721 B lymphoblasts |
| CD81 | CD71 Early Erythroid |
| CDC14A | Testis |
| CDC25C | Testis Intersitial |
| CDC27 | CD71 Early Erythroid |
| CDC34 | CD71 Early Erythroid |
| CDC42EP2 | Smooth Muscle |
| CDC6 | Colorectal adenocarcinoma |
| CDC73 | Colon |
| CDCA4 | CD71 Early Erythroid |
| CDCP1 | Bronchial Epithelial Cells |
| CDH13 | Uterus |
| CDH15 | Cerebellum |
| CDH18 | Subthalamic Nucleus |
| CDH20 | Superior Cervical Ganglion |
| CDH22 | Cerebellum Peduncles |
| CDH3 | Bronchial Epithelial Cells |
| CDH4 | Amygdala |
| CDH5 | Placenta |
| CDH6 | Trigeminal Ganglion |
| CDH7 | Skeletal Muscle |
| CDK5R2 | Whole Brain |
| CDK6 | CD42 |
| CDK8 | Colorectal adenocarcinoma |
| CDKL2 | Superior Cervical Ganglion |
| CDKL3 | Superior Cervical Ganglion |
| CDKL5 | Superior Cervical Ganglion |
| CDKN2D | CD71 Early Erythroid |
| CDON | Tonsil |
| CDR1 | Cerebellum |
| CDS1 | small intestine |
| CDSN | Skin |
| CDX4 | Superior Cervical Ganglion |
| CDYL | CD71 Early Erythroid |
| CEACAN121 | Bone marrow |
| CEACAM3 | Whole Blood |
| CEACAN5 | Colon |
| CEACAM7 | Colon |
| CEACAN8 | Bone marrow |
| CEBPA | Liver |
| CEBPE | Bone marrow |
| CELSR3 | Fetal brain |
| CEMP1 | Skeletal Muscle |
| CENPE | CD71 Early Erythroid |
| CENPI | Appendix |
| CENPQ | Trigeminal Ganglion |
| CENPT | CD71 Early Erythroid |
| CEP170 | Fetal brain |
| CEP55 | X721 B lymphoblasts |
| CEP63 | Whole Blood |
| CEP76 | CD71 Early Erythroid |
| CER1 | Superior Cervical Ganglion |
| CES1 | Liver |
| CES2 | Liver |
| CES3 | Colon |
| CETN1 | Testis |
| CFHR4 | Liver |
| CFHR5 | Liver |
| CFI | Fetal liver |
| CGB | Placenta |
| CGRFIFI | Testis Intersitial |
| CHAD | Trachea |
| CHAF1A | Leukemia lymphoblastic MOLT 10 |
| CHAF1B | Leukemia lymphoblastic MOLT 11 |
| CHAT | Uterus Corpus |
| CHD3 | Fetal brain |
| CHD8 | Trigeminal Ganglion |
| CHI3L1 | Uterus Corpus |
| CHIA | Lung |

TABLE 1-continued

List of Tissue-Specific Genes Determined
by Deconvolution of Adult Transcriptome

| Gene | Tissue |
| --- | --- |
| CHIN | Lymph node |
| CHKA | Testis Intersitial |
| CHM. | Superior Cervical Ganglion |
| CHNIPIB | Superior Cervical Ganglion |
| CHNIP6 | Heart |
| CHOD1 | Testis Germ Cell |
| CHPF | Colorectal adenocarcinoma |
| CHRM2 | Skeletal Muscle |
| CHRM3 | Prefrontal Cortex |
| CHRM4 | Superior Cervical Ganglion |
| CHRMS | Skeletal Muscle |
| CHRNA2 | Heart |
| CHRHA4 | Skeletal Muscle |
| CHRNA5 | Appendix |
| CHRNA6 | Temporal Lobe |
| CHRNA9 | Appendix |
| CHRNB3 | Superior Cervical Ganglion |
| CHST10 | Whole Brain |
| CHST12 | CD56 NK Cells |
| CHST3 | Testis Germ Cell |
| CHST4 | Uterus Corpus |
| CHST7 | Ovary |
| CHSY1 | Placenta |
| CIB2 | BDCA4 Dentritic Cells |
| CIDEA | Ciliary Ganglion |
| CIDEB | Liver |
| CIDEC | Adipocyte |
| CISH | Leukemia chronic Myelogenous K568 |
| CKAP2 | CD71 Early Erythroid |
| CKM | Skeletal Muscle |
| CLCA4 | Colon |
| CLCF1 | Uterus Corpus |
| CLCN1 | Skeletal Muscle |
| CLCN2 | Olfactory Bulb |
| CLCN5 | Appendix |
| CLCN6 | Whole Brain |
| CLCNKA | Kidney |
| CLCNKB | Kidney |
| CLDN10 | Kidney |
| CLDN11 | Heart |
| CLDN15 | small intestine |
| CLDN4 | Colorectal adenocarcinoma |
| CLDN7 | Colon |
| CLDNB | Salivary gland |
| CLEC11A | CD43 |
| CLEC16A | Lymphoma burkitts Raji |
| CLEC4M | Lymph node |
| CLEC5A | CD33 Myeloid |
| CLGN | Testis Intersitial |
| CL1C2 | CD71 Early Erythroid |
| CL1C5 | Skeletal Muscle |
| CLMN | Testis Intersitial |
| CLN3 | Placenta |
| CLN5 | Thyroid |
| CLN6 | pineal day |
| CLPB | Testis Intersitial |
| CLTCL1 | Testis |
| CLUL1 | retina |
| CMA1 | Adrenal Cortex |
| CMAH | Uterus |
| CMAS | CD71 Early Erythroid |
| CMKLR1 | BDCA4 Dentritic Cells |
| CNGA1 | Uterus Corpus |
| CN1H3 | Amygdala |
| CNNMI | Prefrontal Cortex |
| CNNIV4 | pineal day |
| CNR1 | Fetal brain |
| CNR2 | Uterus Corpus |
| CNTFR | Cardiac Myocytes |
| CNTLN | Trigeminal Ganglion |
| CNTN2 | Thalamus |
| CORM | Placenta |
| COG7 | Prostate |
| COL11A1 | Adipocyte |
| COL13A1 | Cardiac Myocytes |

TABLE 1-continued

List of Tissue-Specific Genes Determined
by Deconvolution of Adult Transcriptome

| Gene | Tissue |
| --- | --- |
| COL14A1 | Uterus |
| COL17A1 | Bronchial Epithelial Cells |
| COL19A1 | Trigeminal Ganglion |
| COL7A1 | Skin |
| COL8A2 | retina |
| COL9A1 | pineal night |
| COL9A2 | retina |
| COLECIO | Appendix |
| COLEC11 | Liver |
| COMP | Adipocyte |
| COMT | Liver |
| COQ4 | Thyroid |
| COQ6 | Testis |
| CORIN | Superior Cervical Ganglion |
| CORO1B | CD14 Monocytes |
| CORO2A | Bronchial Epithelial Cells |
| COX6B1 | Superior Cervical Ganglion |
| CP | Fetal liver |
| CPA3 | CD44 |
| CPM | Adipocyte |
| CPN2 | Liver |
| CPNE6 | Amygdala |
| CPNE7 | Leukemia chronic Myelogenous K569 |
| CPDX | Fetal liver |
| CPT1A | X721 B lymphoblasts |
| CPZ | Placenta |
| CR1 | Whole Blood |
| CREBZF | CD8 T cells |
| CRH | Placenta |
| CRHR1 | Cerebellum Peduncles |
| CRUM | Placenta |
| CR1SP2 | Testis Intersitial |
| CRLF1 | Adipocyte |
| CRLF2 | Skeletal Muscle |
| CRTAC1 | Lung |
| CRTAP | Adipocyte |
| CRY2 | pineal night |
| CRYAA | Kidney |
| CRYBA2 | Pancreatic Islet |
| CRYBA4 | Superior Cervical Ganglion |
| CRYBB1 | Superior Cervical Ganglion |
| CRYBB2 | retina |
| CRYBB3 | Superior Cervical Ganglion |
| CSAD | Fetal brain |
| CSAG2 | Leukemia chronic Myelogenous K570 |
| CSDC2 | Heart |
| CSF2 | Colorectal adenocarcinoma |
| CSF2RA | BDCA4 Dentritic Cells |
| CSF3 | Smooth Muscle |
| CSF3R | Whole Blood |
| CSN3 | Salivary gland |
| CSNK1G3 | CD19 Bcells neg. sel. |
| CSPG4 | Trigeminal Ganglion |
| CST2 | Salivary gland |
| CST4 | Salivary gland |
| CST5 | Salivary gland |
| C5T7 | CD56 NK Cells |
| CSTF2T | CD105 Endothelial |
| CTAG2 | X721 B lymphoblasts |
| CTBS | Whole Blood |
| CTDSPL. | Colorectal adenocarcinoma |
| CTF1 | Superior Cervical Ganglion |
| CTUA4 | Superior Cervical Ganglion |
| CTNNA3 | Testis Intersitial |
| CTP52 | Ciliary Ganglion |
| CTSD | Lung |
| CTSG | Bone marrow |
| CTSK | Uterus Corpus |
| CTTNBP2NL | CD8 T cells |
| CUBN | Kidney |
| CUEDC1 | BDCA4 Dentritic Cells |
| CUL1 | Testis Intersitial |
| CUL7 | Smooth Muscle |
| CXCL1 | Smooth Muscle |
| CXCL3 | Smooth Muscle |

TABLE 1-continued

List of Tissue-Specific Genes Determined
by Deconvolution of Adult Transcriptome

| Gene | Tissue |
| --- | --- |
| CXCL5 | Smooth Muscle |
| CXCL6 | Smooth Muscle |
| CXCR3 | BDCA4 Dentritic Cells |
| CXCRS | CD19 Bcells neg. sel. |
| CXorf1 | pineal day |
| CXorf40A | Adrenal Cortex |
| CXorf56 | Superior Cervical Ganglion |
| CXorf57 | Hypothalamus |
| CYB561 | Prostate |
| CYLC1 | Testis Seminiferous Tubule |
| CYLD | CD4 T cells |
| CYorf15B | CD4 T cells |
| CYP19A1 | Placenta |
| CYP1A1 | Lung |
| CYP1A2 | Liver |
| CYP20A1 | BDCA4 Dentritic Cells |
| CYP26A1 | Fetal brain |
| CYP27A1 | Liver |
| CYP2731 | Bronchial Epithelial Cells |
| CYP2A6 | Liver |
| CYP2A7 | Liver |
| CYP237P1 | Superior Cervical Ganglion |
| CYP2C19 | Atrioventricular Node |
| CYP2CB | Liver |
| CYP2C9 | Liver |
| CYP2D6 | Liver |
| CYP2E1 | Liver |
| CYP2F1 | Superior Cervical Ganglion |
| CYP2W1 | Skin |
| CYP3A43 | Liver |
| CYP3A5 | small intestine |
| CYP3A7 | Fetal liver |
| CYP4F11. | Liver |
| CYP4F2 | Liver |
| CYP4FB | Prostate |
| CYP7B1 | Ciliary Ganglion |
| DACT1 | Fetal brain |
| DAGLA | Amygdala |
| DAO | Kidney |
| DAPK2 | Atrioventricular Node |
| DAZ1 | Testis Leydig Cell |
| DAZL | Testis |
| DB1 | CD71 Early Erythroid |
| DBNDD1 | Trigeminal Ganglion |
| DP | Thyroid |
| D031D2 | Trigeminal Ganglion |
| DCC | Testis Seminiferous Tubule |
| DCHS2 | Cerebellum |
| DC1 | Liver |
| DCLREIA | X721 B lymphoblasts |
| DCP1A | CD4 T cells |
| DCT | retina |
| DCUN1D1 | CD71 Early Erythroid |
| DCLIN1D2 | Heart |
| DCX | Fetal brain |
| DDX10 | Leukemia promyelocytic HL61 |
| DDX17 | Heart |
| DDX23 | Thymus |
| DDX25 | Testis Leydig Cell |
| DDX28 | CD14 Monocytes |
| DDX31 | Superior Cervical Ganglion |
| DDX43 | Testis Seminiferous Tubule |
| DDX5 | Liver |
| DDX51 | BDCA4 Dentritic Cells |
| DDX52 | Colorectal adenocarcinoma |
| DECR2 | Liver |
| DEFA4 | Bone marrow |
| DEFAS | small intestine |
| DEFA6 | small intestine |
| DEFB126 | Testis Germ Cell |
| DEGS1 | Skin |
| DENND1A | X721 B lymphoblasts |
| DENND2A | Atrioventricular Node |
| DENND3 | CD33 Myeloid |
| DENND4A | pineal night |

TABLE 1-continued

List of Tissue-Specific Genes Determined
by Deconvolution of Adult Transcriptome

| Gene | Tissue |
| --- | --- |
| DEPDC5 | Lymphoma burkitts Raji |
| DES | Skeletal Muscle |
| DGAT1 | small intestine |
| DGCR14 | Testis Intersitial |
| DGCR6L | Trigeminal Ganglion |
| DGCR8 | Leukemia chronic Myelogenous K571 |
| DGKA | CD4 T cells |
| DGKB | Caudate nucleus |
| DGKE | Superior Cervical Ganglion |
| DGKG | Cerebellum |
| DGKQ | Superior Cervical Ganglion |
| DHDDS | pineal day |
| DHODH | Liver |
| DHR51 | Liver |
| DHRS12 | Liver |
| DHR52 | Colorectal adenocarcinoma |
| DHRS9 | Trachea |
| DHTKD1 | Liver |
| DHX29 | CD71 Early Erythroid |
| DHX35 | Leukemia lymphoblastic MOLT 12 |
| DHX38 | CD56 NK Cells |
| DHX57 | Testis Seminiferous Tubule |
| DIAPH2 | Testis Germ Cell |
| DIDO1 | CD8 T cells |
| DIO2 | Thyroid |
| DIO3 | Cerebellum Peduncles |
| DKFZP434L187 | Atrioventricular Node |
| DKK2 | Ciliary Ganglion |
| DKK4 | Pancreas |
| DLAT | Adipocyte |
| DLEU2 | CD71 Early Erythroid |
| DLG3 | Fetal brain |
| DLK2 | Testis Leydig Cell |
| DLL3 | Fetal brain |
| DIX2 | Fetal brain |
| DLX4 | Placenta |
| DIX5 | Placenta |
| DMC1 | Superior Cervical Ganglion |
| DMD | Olfactory Bulb |
| DMPK | Heart |
| DMWD | Atrioventricular Node |
| DNA2 | X721 B lymphoblasts |
| DNAH17 | Testis |
| DNAH2 | Atrioventricular Node |
| DNAH9 | Cardiac Myocytes |
| DNAI1 | Testis |
| DNAI2 | Testis |
| DNAJC1 | CD56 NK Cells |
| DNAJC9 | CD71 Early Erythroid |
| DNAL4 | Testis |
| DNALI1 | Testis Intersitial |
| DNASE1L1 | CD14 Monocytes |
| DNASE1L.2 | Tonsil |
| DNASE1L3 | BDCA4 Dentritic Cells |
| DNASE2B | Salivary gland |
| DND1 | Testis |
| DNM2 | BDCA4 Dentritic Cells |
| DNMT3A | Superior Cervical Ganglion |
| DNMT3B | Leukemia chronic Myelogenous K572 |
| DNMT3L | Liver |
| DOC2B | Adrenal gland |
| DOCK5 | Superior Cervical Ganglion |
| DOCK6 | Lung |
| DOK2 | CD14 Monocytes |
| DOK3 | Superior Cervical Ganglion |
| DOK4 | Fetal brain |
| DOKS | Fetal brain |
| DOLK | Testis |
| DOPEY2 | Skeletal Muscle |
| DOT1L | Superior Cervical Ganglion |
| DPAGTI | X721 B lymphoblasts |
| DPEP3 | Testis |
| DPF3 | Cerebellum |
| DPH2 | Skeletal Muscle |
| DPM2 | CD71 Early Erythroid |

TABLE 1-continued

List of Tissue-Specific Genes Determined
by Deconvolution of Adult Transcriptome

| Gene | Tissue |
|---|---|
| DPP4 | Smooth Muscle |
| DPPA4 | CD45 |
| DPT | Adipocyte |
| DPY19L2P2 | Leukemia lymphoblastic MOLT 13 |
| DRD2 | Caudate nucleus |
| DSC1 | Skin |
| DSG1 | Skin |
| DTI | CD105 Endothelial |
| DTX2 | Skeletal Muscle |
| DIYMK | CD105 Endothelial |
| DUSP10 | X721 B lymphoblasts |
| DUSP26 | Skeletal Muscle |
| DUSP4 | Placenta |
| DUSP7 | Bronchial Epithelial Cells |
| DVL3 | Placenta |
| DYNC2H1 | Pituitary |
| DYRK2 | CD8 T cells |
| DYRK4 | Testis Intersitial |
| DYSF | Whole Blood |
| E2P1 | CD71 Early Erythroid |
| E2F2 | CD71 Early Erythroid |
| E24 | CD71 Early Erythroid |
| E2F5 | Lymphoma burkitts Daudi |
| E28 | CD71 Early Erythroid |
| E4F1 | CD4 T cells |
| EAF2 | CD19 Bcells neg. sel. |
| EB13 | Placenta |
| ECHDC1 | Adipocyte |
| ECH51 | Liver |
| ECM1 | Tongue |
| ECW | Heart |
| EDA | Trigeminal Ganglion |
| EDA2R | Superior Cervical Ganglion |
| EDC3 | Testis |
| ED1L3 | Occipital Lobe |
| EDN2 | Superior Cervical Ganglion |
| EDN3 | retina |
| EDNRA | Uterus |
| EFCA31 | Superior Cervical Ganglion |
| EPHC1 | Testis Intersitial |
| EFHC2 | Appendix |
| EFNA4 | Prostate |
| EFN31 | Colorectal adenocarcinoma |
| EFNB3 | Fetal brain |
| EGF | Kidney |
| EGFR | Placenta |
| EGLN1 | Whole Blood |
| EIF1AY | CD71 Early Erythroid |
| EIF2AK1 | CD71 Early Erythroid |
| E1F2B4 | Testis |
| EIF2C2 | CD71 Early Erythroid |
| E1F2C3 | Pituitary |
| E1F3K | Superior Cervical Ganglion |
| E1F4G2 | Liver |
| E1F4A2 | Ciliary Ganglion |
| ELF3 | Colon |
| ELL2 | Pancreatic Islet |
| ELMO3 | CD71 Early Erythroid |
| ELOVL6 | Adipocyte |
| ELSPBP1 | Testis Leydig Cell |
| ELTD1 | Smooth Muscle |
| EMID1 | Fetal brain |
| EMILIN2 | Superior Cervical Ganglion |
| EML1 | Fetal brain |
| EMR3 | Whole Blood |
| EMX2 | Uterus |
| EN1 | Adipocyte |
| ENDOG | Liver |
| ENO3 | Skeletal Muscle |
| ENOX1 | Fetal brain |
| ENPP1 | Thyroid |
| ENTPD1 | X721 B lymphoblasts |
| ENTPD2 | Superior Cervical Ganglion |
| ENTPD3 | Caudate nucleus |
| ENTPD4 | Smooth Muscle |

TABLE 1-continued

List of Tissue-Specific Genes Determined
by Deconvolution of Adult Transcriptome

| Gene | Tissue |
|---|---|
| ENTPD7 | Bone marrow |
| EPB41 | CD71 Early Erythroid |
| EPB41L4A | Trigeminal Ganglion |
| EPHA4 | Liver |
| EPHA3 | Fetal brain |
| EPHAS | Fetal brain |
| EPN2 | CD71 Early Erythroid |
| EPN3 | Thalamus |
| EPS1S11 | Appendix |
| EPS8I1 | Placenta |
| EPS8I3 | Pancreas |
| EPX | Bone marrow |
| EPYC | Placenta |
| ERCC1 | Heart |
| ERCC4 | Superior Cervical Ganglion |
| ERCC6 | Ovary |
| ERCC8 | Uterus Corpus |
| EREG | CD46 |
| ERF | Ciliary Ganglion |
| ERG | CD47 |
| ERICH1 | Superior Cervical Ganglion |
| ERLIN2 | Thyroid |
| ERMAP | CD71 Early Erythroid |
| ERNIPI | CD56 NK Cells |
| ERNI | Liver |
| EROILB | Pancreatic Islet |
| ESM1 | CD105 Endothelial |
| ESRI | Uterus |
| ETFB | Liver |
| ETNKI | Colon |
| ETNK2 | Liver |
| ETV3 | Superior Cervical Ganglion |
| ETV4 | Colorectal adenocarcinoma |
| EVPL | Tongue |
| EXOSC1 | Trigeminal Ganglion |
| EXOSC2 | X721 B lymphoblasts |
| EXOSC4 | Testis |
| EXOSC5 | X721 B lymphoblasts |
| EXPH5 | Placenta |
| EXT2 | Smooth Muscle |
| EXTL3 | Subthalamic Nucleus |
| EYA3 | Cardiac Myocytes |
| EYA4 | Skin |
| F10 | Liver |
| F11 | Pancreas |
| F12 | Liver |
| F13B | Fetal liver |
| F2R | Cardiac Myocytes |
| F2RL1 | Colon |
| FAAH | pineal night |
| FABP6 | small intestine |
| FABP7 | Fetal brain |
| FADSI | Adipocyte |
| FAH | Liver |
| FAIM | Colorectal adenocarcinoma |
| FAM105A | BDCA4 Dentritic Cells |
| FAM106A | Atrioventricular Node |
| FAM108BI | Whole Brain |
| FAM110B | Trigeminal Ganglion |
| FAM118A | CD33 Myeloid |
| FAM119B | Uterus Corpus |
| FAM120C | Ovary |
| FAM125B | Spinal Cord |
| FAM127B | Thyroid |
| FAM135A | Appendix |
| FAM149A | pineal day |
| FAM48A | Testis Intersitial |
| FAM50B | Whole Brain |
| FAM55D | Colon |
| FAM5C | Amygdala |
| FAMBA | Whole Blood |
| FAM86A | Pituitary |
| FAM86B1 | Skeletal Muscle |
| FAM86C | Leukemia promyelocytic HL62 |
| FANCE | Lymphoma burkitts Daudi |

TABLE 1-continued

List of Tissue-Specific Genes Determined
by Deconvolution of Adult Transcriptome

| Gene | Tissue |
|------|--------|
| FANCG | Leukemia lymphoblastic MOLT 14 |
| FARP2 | Testis |
| FARS2 | Heart |
| FAS | Whole Blood |
| FASLG | CD56 NK Cells |
| FASTK | Heart |
| FASTKD2 | X721 B lymphoblasts |
| FAT4 | Fetal brain |
| FBLN2 | Adipocyte |
| FBN2 | Placenta |
| FBP1 | Liver |
| FBP2 | Skeletal Muscle |
| FBXL12 | Thymus |
| FBXL15 | Whole Brain |
| FBXL4 | CD71 Early Erythroid |
| FBXL6 | Pancreas |
| FBXL8 | X721 B lymphoblasts |
| FBXO17 | Leukemia chronic Myelogenous K573 |
| FBXO38 | CD8 T cells |
| FBXO4 | Trigeminal Ganglion |
| FBXO46 | X721 B lymphoblasts |
| FCGR2A | Whole Blood |
| FCGR2B | Placenta |
| FCHOI | Lymphoma burkitts Raji |
| FCN2 | Liver |
| FCRL2 | CD19 Bcells neg. sel. |
| FECH | CD71 Early Erythroid |
| FEM1B | Testis Intersitial |
| FFMIC | Cerebellum |
| FER1L4 | Trigeminal Ganglion |
| FETUB | Liver |
| FEZF2 | Amygdala |
| FFAR2 | Whole Blood |
| FFAR3 | Temporal Lobe |
| FGD1 | Fetal brain |
| FGD2 | CD33 Myeloid |
| FGF12 | Occipital Lobe |
| FGF14 | Cerebellum |
| FGE17 | Cingulate Cortex |
| FGF2 | Smooth Muscle |
| FGF22 | Ovary |
| FGF23 | Superior Cervical Ganglion |
| FGF3 | Colorectal adenocarcinoma |
| FGF4 | Olfactory Bulb |
| FGF5 | Superior Cervical Ganglion |
| FGF8 | Superior Cervical Ganglion |
| FGF9 | Cerebellum Peduncles |
| FGFR1OP | Testis Intersitial |
| FGFR4 | Liver |
| FGL1 | Fetal liver |
| FGL2 | CD14 Monocytes |
| FHIT | CD4 T cells |
| FHL3 | Skeletal Muscle |
| FHL5 | Testis Intersitial |
| FILIP1L | Uterus |
| FKBP10 | Smooth Muscle |
| FKBP14 | Smooth Muscle |
| FKBP6 | Testis |
| FKBP6 | CD105 Endothelial |
| FKRP | Superior Cervical Ganglion |
| FIG | Skin |
| FLJ20712 | Temporal Lobe |
| FLNC | Skeletal Muscle |
| FLOT2 | Whole Blood |
| FLT1 | Superior Cervical Ganglion |
| FLT4 | Placenta |
| FMO2 | Lung |
| FM03 | Liver |
| FMO6P | Appendix |
| FN3K | Superior Cervical Ganglion |
| FNBP1L | Fetal brain |
| FNDC8 | Testis Intersitial |
| FOLH1 | Prostate |
| FO5L1 | Colorectal adenocarcinoma |
| FOXA1 | Prostate |

TABLE 1-continued

List of Tissue-Specific Genes Determined
by Deconvolution of Adult Transcriptome

| Gene | Tissue |
|------|--------|
| FOXA2 | Pancreatic Islet |
| FOXB1 | Superior Cervical Ganglion |
| FOXC1 | Salivary gland |
| FOXC2 | Superior Cervical Ganglion |
| FOXD3 | Superior Cervical Ganglion |
| FOXD4 | Globus Pallidus |
| FOXE1 | Thyroid |
| FOXE3 | Superior Cervical Ganglion |
| FOXK2 | Adrenal Cortex |
| FOXL1 | Liver |
| FOXN1 | Superior Cervical Ganglion |
| FOXN2 | Appendix |
| FOXP3 | Adrenal Cortex |
| FPGS | Ovary |
| FPGT | pineal day |
| FPR2 | Whole Blood |
| FPR3 | Superior Cervical Ganglion |
| FRAT1 | Whole Blood |
| FRAT2 | Whole Blood |
| FRK | Superior Cervical Ganglion |
| FRMD8 | Superior Cervical Ganglion |
| FRs2 | Pituitary |
| FRS3 | Testis |
| FRZB | retina |
| FSHB | Pituitary |
| FSHR | Superior Cervical Ganglion |
| FST | Bronchial Epithelial Cells |
| FSTL3 | Placenta |
| FSTL4 | Appendix |
| FTCD | Liver |
| FTSJ1 | Bronchial Epithelial Cells |
| FXC1 | Superior Cervical Ganglion |
| FXN | CD105 Endothelial |
| FXYD2 | Kidney |
| FYCO1 | Tongue |
| FZD4 | Adipocyte |
| FZD5 | Colon |
| FZD7 | Cerebellum |
| FZD8 | Superior Cervical Ganglion |
| FZD9 | Appendix |
| FZR1 | CD71 Early Erythroid |
| G6PC | Liver |
| G6PC2 | Superior Cervical Ganglion |
| GABI | Superior Cervical Ganglion |
| GABRA4 | Caudate nucleus |
| GABRA5 | Amygdala |
| GABRB2 | Skin |
| GABR | Placenta |
| GA3RG3 | Subthalamic Nucleus |
| GABRP | Tonsil |
| GABRQ | Skeletal Muscle |
| GAD2 | Caudate nucleus |
| GADD45G | Placenta |
| GADD45UP1 | Heart |
| GABSTI | Spinal Cord |
| GALKI | Liver |
| GALK2 | Leukemia chronic Myelogenous K574 |
| GALNS | CD33 Myeloid |
| GALNT12 | Colon |
| GALNT14 | Kidney |
| GAINT4 | CD71 Early Erythroid |
| GALNT6 | CD71 Early Erythroid |
| GALNT8 | Trigeminal Ganglion |
| GALR2 | Superior Cervical Ganglion |
| GALT | Liver |
| GAMT | Liver |
| GAPDHS | Testis Intersitial |
| GAPVDI | CD71 Early Erythroid |
| GARNL3 | Appendix |
| GAST | Cerebellum |
| GATA4 | Heart |
| GATADI | Leukemia chronic Myelogenous K575 |
| GATC | Superior Cervical Ganglion |
| GBA | Placenta |
| GBX1 | Bone marrow |

TABLE 1-continued

List of Tissue-Specific Genes Determined
by Deconvolution of Adult Transcriptome

| Gene | Tissue |
|------|--------|
| GCAT | Liver |
| GCDH | Liver |
| GCGR | Liver |
| GCHFR | Liver |
| GCKR | Liver |
| GCLC | CD71 Early Erythroid |
| GCLM | CD71 Early Erythroid |
| GCM1 | Placenta |
| GCM2 | Skeletal Muscle |
| GCNT1 | CD19 Bcells neg. sel. |
| GCNT2 | CD71 Early Erythroid |
| GDAP1LI | Fetal brain |
| GDF11 | retina |
| GDF15 | Placenta |
| GDF2 | Subthalamic Nucleus |
| GDF5 | Fetal liver |
| GDF9 | Testis Leydig Cell |
| GDPD3 | Colon |
| GEM | Uterus Corpus |
| GEMIN4 | Testis Intersitial |
| GEMIN8 | Skeletal Muscle |
| GFOD2 | Superior Cervical Ganglion |
| GFRA3 | Liver |
| GFRA4 | Pons |
| GGTIC1 | Lung |
| GH2 | Placenta |
| GHRHR | Pituitary |
| GHSR | Superior Cervical Ganglion |
| GIF | Superior Cervical Ganglion |
| GIMAP4 | Whole Blood |
| GINS4 | X721 B lymphoblasts |
| GIP | small intestine |
| GB,C2 | small intestine |
| GJA3 | Superior Cervical Ganglion |
| GJA4 | Lung |
| GJA5 | Superior Cervical Ganglion |
| GJA8 | Skeletal Muscle |
| GJB1 | Liver |
| GJB3 | Bronchial Epithelial Cells |
| GJB5 | Bronchial Epithelial Cells |
| GJC1 | Superior Cervical Ganglion |
| GJC2 | Spinal Cord |
| GK | Whole Blood |
| GK2 | Testis Intersitial |
| GK3P | Testis Germ Cell |
| GKN1 | small intestine |
| GLE1 | Testis Intersitial |
| GLI1 | Atrioventricular Node |
| GLMN | Skeletal Muscle |
| GLP2R | Superior Cervical Ganglion |
| GLRA1 | Superior Cervical Ganglion |
| GLRA2 | Uterus Corpus |
| GLS2 | Liver |
| GLT8D2 | Smooth Muscle |
| GLTP | Tonsil |
| GLTPD1 | Heart |
| GMDS | Colon |
| GMEB1 | CD56 NK Cells |
| GML | Trigeminal Ganglion |
| GNA13 | BDCA4 Dentritic Cells |
| GNA14 | Superior Cervical Ganglion |
| GNAT1 | retina |
| GNAZ | Fetal brain |
| GNB1L | Leukemia chronic Myelogenous K576 |
| GNG4 | Superior Cervical Ganglion |
| GNLY | CD56 NK Cells |
| GNRHR | Pituitary |
| GOLT1B | Smooth Muscle |
| GON41 | Leukemia chronic Myelogenous K577 |
| GP | Trigeminal Ganglion |
| GP6 | Superior Cervical Ganglion |
| GP9 | Whole Blood |
| GPATCH1 | CD8 T cells |
| GPATCH2 | Testis Seminiferous Tubule |
| GPATCH3 | CD14 Monocytes |

TABLE 1-continued

List of Tissue-Specific Genes Determined
by Deconvolution of Adult Transcriptome

| Gene | Tissue |
|------|--------|
| GPATCH4 | Atrioventricular Node |
| GPATCH8 | CD56 NK Cells |
| GPC4 | Pituitary |
| GPC5 | pineal day |
| GPD1 | Adipocyte |
| GPI | CD71 Early Erythroid |
| GPKOW | CD71 Early Erythroid |
| GPR124 | retina |
| GPR137 | Testis |
| GPR143 | retina |
| GPR153 | Fetal brain |
| GPR1S7 | Globus Pallidus |
| GPR161 | Uterus |
| GPRI7 | Whole Brain |
| GPR172R | Placenta |
| GPRIM | Smooth Muscle |
| GPR18 | CD19 Bcells neg. sel. |
| GPR182 | Superior Cervical Ganglion |
| G PR20 | Trigeminal Ganglion |
| GPR21 | Globus Pallidus |
| G PR31 | Superior Cervical Ganglion |
| GPR32 | Superior Cervical Ganglion |
| GPF135 | Pancreas |
| GPR37L1 | Amygdala |
| G PR39 | Superior Cervical Ganglion |
| GPR4 | Lung |
| GPR44 | Thymus |
| GPR50 | Superior Cervical Ganglion |
| GPF152 | Superior Cervical Ganglion |
| GPR6 | Caudate nucleus |
| GPR64 | Testis Leydig Cell |
| GPR65 | CD56 NK Cells |
| GPR68 | Skeletal Muscle |
| GPR87 | Bronchial Epithelial Cells |
| GPR98 | Medulla Oblongata |
| GPRIN2 | Superior Cervical Ganglion |
| GPT | Liver |
| GPX5 | Testis Leydig Cell |
| GRAMD1C | Appendix |
| GRB7 | Liver |
| GREM1 | Smooth Muscle |
| GRID2 | Superior Cervical Ganglion |
| GRIK3 | Superior Cervical Ganglion |
| GRIK4 | Olfactory Bulb |
| GRIN2A | Subthalamic Nucleus |
| GRIN2B | Skeletal Muscle |
| GRIN2C | Thyroid |
| GRIN2D | Superior Cervical Ganglion |
| GRIP1 | Superior Cervical Ganglion |
| GRIP2 | CD48 |
| GRK1 | Superior Cervical Ganglion |
| GRK4 | Testis |
| GRM1 | Cerebellum |
| GRIM | Heart |
| GRM4 | Cerebellum Peduncles |
| GRRPI | Globus Pallidus |
| GRTPI | Superior Cervical Ganglion |
| GSR | X721 B lymphoblasts |
| GSTCD | Atrioventricular Node |
| GSTMI | Liver |
| GSTM2 | Liver |
| GSTM4 | small intestine |
| GSTT2 | Whole Brain |
| GSTTP1 | Testis Intersitial |
| GSTZI | Liver |
| GTF2IRD1 | Colorectal adenocarcinoma |
| GTF3C5 | Heart |
| GTPBPI | CD71 Early Erythroid |
| GUCY1A2 | Superior Cervical Ganglion |
| GUCY1B2 | Superior Cervical Ganglion |
| GUCY2C | Colon |
| GUCY2D | BDCA4 Dentritic Cells |
| GUF1 | Superior Cervical Ganglion |
| GULP1 | Placenta |
| GYG2 | Adipocyte |

TABLE 1-continued

List of Tissue-Specific Genes Determined
by Deconvolution of Adult Transcriptome

| Gene | Tissue |
|------|--------|
| GYPE | CD71 Early Erythroid |
| GYS1 | Heart |
| GZMK | CD8 T cells |
| H2AFB1 | Testis |
| HAAO | Liver |
| HAL | Fetal liver |
| HAMP | Liver |
| HAO1 | Liver |
| HAO2 | Kidney |
| HAPLN1 | Cardiac Myocytes |
| HAPLN2 | Spinal Cord |
| HAS2 | Skeletal Muscle |
| HBE1 | Leukemia chronic Myelogenous K578 |
| HBQ1 | CD71 Early Erythroid |
| HBSIL | CD71 Early Erythroid |
| HBXIP | Kidney |
| HCCS | CD71 Early Erythroid |
| HCFC2 | Testis Intersitial |
| HCG4 | Superior Cervical Ganglion |
| HCG9 | Liver |
| HCN4 | Testis Leydig Cell |
| HCRT | Hypothalamus |
| HCRTR1 | Bone marrow |
| HCRTR2 | Atrioventricular Node |
| HDAC11 | Testis |
| HDGF | CD71 Early Erythroid |
| HEATR6 | Atrioventricular Node |
| HECTD3 | CD71 Early Erythroid |
| HECW1 | Atrioventricular Node |
| HEPH | Leukemia chronic Myelogenous K579 |
| HEXMI1 | CD71 Early Erythroid |
| HEY2 | retina |
| HGC63 | Skeletal Muscle |
| HGF | Smooth Muscle |
| HGFAC | Liver |
| HHAT | BDCA4 Dentritic Cells |
| HH1PL2 | Testis Intersitial |
| HHIA1 | Adrenal gland |
| HHIA3 | Liver |
| H1C1 | Superior Cervical Ganglion |
| H1C2 | Leukemia chronic Myelogenous K580 |
| H1F3A | Superior Cervical Ganglion |
| HIGDL1B | Lung |
| HIP1R | CD19 Bcells neg. sel. |
| HIPK3 | CD33 Myeloid |
| H1ST1H1E | Leukemia chronic Myelogenous K581 |
| H1ST1H1T | Dorsal Root Ganglion |
| H1ST1H2AB | CD19 Bcells neg. sel. |
| HIST1H28C | Leukemia chronic Myelogenous K582 |
| HIST1H2BG | CD8 T cells |
| HIST1H2E0 | Ciliary Ganglion |
| HIST1H2BM | Superior Cervical Ganglion |
| HIST1H2BN | small intestine |
| HIST1H3F | Uterus Corpus |
| HIST1H31 | Cardiac Myocytes |
| HIST1H31 | Atrioventricular Node |
| HIST1H4A | CD71 Early Erythroid |
| HIST1H4E | Superior Cervical Ganglion |
| HIST1H4G | Skeletal Muscle |
| HIST3H2A | Leukemia chronic Myelogenous K583 |
| HWEP2 | Fetal brain |
| HKDCI | pineal night |
| HIA-DOB | CD19 Bcells neg. sel. |
| HICS | Thyroid |
| HMS | CD71 Early Erythroid |
| HMGA2 | Bronchial Epithelial Cells |
| HNIGB3 | Placenta |
| HMGCL | Liver |
| HMGCS2 | Liver |
| HMHB1 | Skeletal Muscle |
| HNIF4G | Ovary |
| HNRNPA2B1 | Liver |
| HOOK1 | Testis Intersitial |
| HOOK2 | Thyroid |
| HOXA1 | Leukemia chronic Myelogenous K584 |

TABLE 1-continued

List of Tissue-Specific Genes Determined
by Deconvolution of Adult Transcriptome

| Gene | Tissue |
|------|--------|
| HOXA10 | Uterus |
| HOXA3 | Superior Cervical Ganglion |
| HOXA6 | Kidney |
| HOXA7 | Adrenal Cortex |
| HOXA9 | Colorectal adenocarcinoma |
| HOXB1 | Cingulate Cortex |
| HOXB13 | Prostate |
| HOXBS | Colorectal adenocarcinoma |
| HOXB6 | Colorectal adenocarcinoma |
| HOXB7 | Colorectal adenocarcinoma |
| HOXBB | Superior Cervical Ganglion |
| HOXCI1 | Superior Cervical Ganglion |
| HOXICS | Liver |
| HOXC8 | Skeletal Muscle |
| HOXD1 | Trigeminal Ganglion |
| HOXD10 | Uterus |
| HOXD11 | Appendix |
| HOXD12 | Skeletal Muscle |
| HOXD3 | Uterus |
| HOXD4 | Uterus |
| HOXD9 | Uterus |
| HP | Liver |
| HPGD | Placenta |
| HPN | Liver |
| HPR | Liver |
| HPS1 | CD71 Early Erythroid |
| HPS4 | CD105 Endothelial |
| HR | pineal day |
| HRC | Heart |
| HRG | Liver |
| HRK | CD19 Bcells neg. sel. |
| HS1BP3 | CD14 Monocytes |
| HS3ST1 | Ovary |
| HS3ST3B1 | Heart |
| HS6ST1 | Superior Cervical Ganglion |
| HSD11B1 | Liver |
| HSD17B1 | Placenta |
| HSD17B2 | Placenta |
| HSD17B6 | Liver |
| HSD17B8 | Liver |
| HSD3B1 | Placenta |
| HSF1 | Heart |
| HSFX1 | Cardiac Myocytes |
| HSP9OAA1 | Heart |
| HSPA1L | Testis Intersitial |
| HSPA4L | Testis Intersitial |
| HSPA6 | Whole Blood |
| HSPB2 | Heart |
| HSPB3 | Heart |
| HSPC159 | Superior Cervical Ganglion |
| HTNI | Salivary gland |
| HTRIA | Liver |
| HTR1B | Heart |
| HTRID | Skeletal Muscle |
| HTR1E | pineal night |
| HTRIF | Appendix |
| HTR2A | Prefrontal Cortex |
| HTR2C | Caudate nucleus |
| HTR3A | Dorsal Root Ganglion |
| HTR3B | Skin |
| HTR5A | Skeletal Muscle |
| HTR7 | Cardiac Myocytes |
| HTRA2 | CD71 Early Erythroid |
| HUS1 | Superior Cervical Ganglion |
| HYAL2 | Lung |
| HYAL4 | Superior Cervical Ganglion |
| ICAM4 | CD71 Early Erythroid |
| ICAM5 | Amygdala |
| ICOSLG | Skeletal Muscle |
| IDE | Testis Germ Cell |
| IDH3G | Heart |
| IER31P1 | Smooth Muscle |
| IF144 | CD33 Myeloid |
| IFIT1 | Whole Blood |
| IFIT2 | Whole Blood |

TABLE 1-continued

List of Tissue-Specific Genes Determined
by Deconvolution of Adult Transcriptome

| Gene | Tissue |
|---|---|
| IFIT5 | Whole Blood |
| IFNA21 | Testis Seminiferous Tubule |
| IFNA4 | Dorsal Root Ganglion |
| IFNA5 | Superior Cervical Ganglion |
| IFNA6 | Superior Cervical Ganglion |
| IFNAR1 | Superior Cervical Ganglion |
| IFNG | CD56 NK Cells |
| IFNW1 | Ovary |
| IFT140 | Thyroid |
| IFT52 | CD71 Early Erythroid |
| IFT81 | Testis Leydig Cell |
| IGF1R | Prostate |
| IGF2AS | Subthalamic Nucleus |
| IGFALS | Liver |
| IGLL1 | CD49 |
| IGLV6-57 | Lymph node |
| IHH | Heart |
| IKZF3 | CD8 T cells |
| IKZF5 | CD8 T cells |
| IL10 | Atrioventricular Node |
| 1L11 | Smooth Muscle |
| IL11RA | CD4 T cells |
| 1L12A | Uterus Corpus |
| IL12RB2 | CD56 NK Cells |
| 1L13 | Testis Intersitial |
| 1L13RA2 | Testis Intersitial |
| 1L15 | pineal night |
| 1L17B | Olfactory Bulb |
| 1L17RA | CD33 Myeloid |
| 1L17RB | Kidney |
| IL18RAP | CD56 NK Cells |
| IL19 | Trachea |
| IL1B | Smooth Muscle |
| IL1F6 | Superior Cervical Ganglion |
| IL1F7 | Skeletal Muscle |
| 1L1F9 | Superior Cervical Ganglion |
| 1L1RAPL1 | Prefrontal Cortex |
| 1L1RAPL2 | Superior Cervical Ganglion |
| 1L1R1L | Placenta |
| IL2 | Heart |
| IL20RA | Ciliary Ganglion |
| IL21 | Superior Cervical Ganglion |
| IL22 | Superior Cervical Ganglion |
| IL24 | Smooth Muscle |
| IL25 | Pons |
| IL2RA | Superior Cervical Ganglion |
| 1L2RB | CD56 NK Cells |
| IL3RA | BDCA4 Dentritic Cells |
| 1L4 | Atrioventricular Node |
| IL4R | CD19 Bcells neg. sel. |
| 1L5 | Atrioventricular Node |
| IL5RA | Ciliary Ganglion |
| IL9 | Leukemia promyelocytic HL63 |
| IL9R | Testis Intersitial |
| 1LVBL | Heart |
| IMPG1 | retina |
| 1NCENP | Leukemia lymphoblastic MOLT 15 |
| INE1 | Atrioventricular Node |
| ING1 | CD19 Bcells neg. sel. |
| INHA | Testis Germ Cell |
| INHBA | Placenta |
| INHBE | Liver |
| INPP5B | X721 B lymphoblasts |
| INSG2 | X721 B lymphoblasts |
| INSL4 | Placenta |
| INSL6 | Superior Cervical Ganglion |
| INSRR | Superior Cervical Ganglion |
| INTS12 | BDCA4 Dentritic Cells |
| INTS5 | Liver |
| IPO8 | CD4 T cells |
| IQCB1 | Lymphoma burkitts Daudi |
| IRF2 | Whole Blood |
| IRF6 | Bronchial Epithelial Cells |
| IRS4 | Skeletal Muscle |
| IRX4 | Skin |

TABLE 1-continued

List of Tissue-Specific Genes Determined
by Deconvolution of Adult Transcriptome

| Gene | Tissue |
|---|---|
| IRX5 | Lung |
| 1SCA1 | CD71 Early Erythroid |
| LSL1 | Pancreatic Islet |
| 1SOC2 | Liver |
| 1SYNA1 | Testis Germ Cell |
| ITCH | Testis Intersitial |
| ITFG2 | CD4 T cells |
| ITGA2 | Bronchial Epithelial Cells |
| ITGA3 | Bronchial Epithelial Cells |
| ITGA9 | Testis Seminiferous Tubule |
| ITGB1BP3 | Heart |
| ITGB5 | Colorectal adenocarcinoma |
| ITGB6 | Bronchial Epithelial Cells |
| ITGB8 | Appendix |
| ITGBL1 | Adipocyte |
| ITIH4 | Liver |
| ITIH5 | Placenta |
| ITM2B | X721 B lymphoblasts |
| ITPKA | Whole Brain |
| ITSN1 | CD71 Early Erythroid |
| IVL | Tongue |
| JAKMIP2 | Prefrontal Cortex |
| JMJD5 | Liver |
| JPH2 | Superior Cervical Ganglion |
| KAL1 | Spinal Cord |
| KAZALD1 | Skeletal Muscle |
| KCNA1 | Superior Cervical Ganglion |
| KCNA10 | Skeletal Muscle |
| KCNA2 | Skeletal Muscle |
| KCNA3 | Dorsal Root Ganglion |
| KCNA4 | Superior Cervical Ganglion |
| KCNAB1 | Caudate nucleus |
| KCNAB3 | Subthalamic Nucleus |
| KCNB2 | Trigeminal Ganglion |
| KCNC3 | Lymphoma burkitts Daudi |
| KCND1 | Thyroid |
| KCND2 | Cerebellum Peduncles |
| KCNE1 | Pancreas |
| KCNE1L | Superior Cervical Ganglion |
| KCNE4 | Uterus Corpus |
| KCNG1 | CD19 Bcells neg. sel. |
| KCNG2 | Superior Cervical Ganglion |
| KCNH1 | Appendix |
| KCNH2 | CD105 Endothelial |
| KCNH4 | Superior Cervical Ganglion |
| KCNJ1 | Kidney |
| KCNJ10 | Occipital Lobe |
| KCNJ13 | Superior Cervical Ganglion |
| KCNJ14 | Appendix |
| KCNJ2 | Whole Blood |
| KCNJ3 | Superior Cervical Ganglion |
| KCNJ6 | Cingulate Cortex |
| KCNJ9 | Cerebellum |
| KCNK10 | BDCA4 Dentritic Cells |
| KCNK12 | Olfactory Bulb |
| KCNK2 | Atrioventricular Node |
| KCNK7 | Superior Cervical Ganglion |
| KCNMA1 | Uterus |
| KCNMB3 | Testis Intersitial |
| KCNN2 | Adrenal gland |
| KCNN4 | CD71 Early Erythroid |
| KCNS3 | Lung |
| KCNV2 | retina |
| KCTD14 | Adrenal gland |
| KCTD1S | Kidney |
| KCTD17 | pineal day |
| KCTD20 | CD71 Early Erythroid |
| KCTD5 | BDCA4 Dentritic Cells |
| KCTD7 | pineal night |
| KDELC1 | Cardiac Myocytes |
| KDELR3 | Smooth Muscle |
| KDSR | Olfactory Bulb |
| KIAA0040 | CD19 Bcells neg. sel. |
| KIAA0087 | Trigeminal Ganglion |
| KIAA0090 | Placenta |

TABLE 1-continued

List of Tissue-Specific Genes Determined
by Deconvolution of Adult Transcriptome

| Gene | Tissue |
| --- | --- |
| KIAA0100 | BDCA4 Dentritic Cells |
| KIAA0141 | Superior Cervical Ganglion |
| KIAA0196 | CD14 Monocytes |
| KIAA0319 | Fetal brain |
| KIAA0556 | pineal day |
| KIAA0586 | Testis Intersitial |
| KIAA1024 | Adrenal Cortex |
| KIAA1199 | Smooth Muscle |
| KIAA1310 | Uterus Corpus |
| KIAA1324 | Prostate |
| KIAA1539 | CD71 Early Erythroid |
| KIAA1609 | Bronchial Epithelial Cells |
| KIAA1751 | Superior Cervical Ganglion |
| KIF17 | Cingulate Cortex |
| KIF18A | X721 B lymphoblasts |
| KIF18B | Leukemia lymphoblastic MOLT 16 |
| KIF21B | Fetal brain |
| KIF22 | CD71 Early Erythroid |
| KIF25 | Superior Cervical Ganglion |
| KIF26B | Ciliary Ganglion |
| KIF5A | Whole Brain |
| KIFC1 | CD71 Early Erythroid |
| KIR2M2 | CD56 NK Cells |
| KIR2DL3 | CD56 NK Cells |
| KIR2DL4 | CD56 NK Cells |
| KM2DS4 | CD56 NK Cells |
| KIRDL1 | CD56 NK Cells |
| KIRDL2 | CD56 NK Cells |
| KIRREL | Superior Cervical Ganglion |
| KISS1 | Placenta |
| KL | Kidney |
| K1F12 | CD8 T cells |
| KLF15 | Liver |
| KLF3 | CD71 Early Erythroid |
| KLF8 | Spinal Cord |
| KLHDC4 | CD56 NK Cells |
| KLHL11 | Temporal Lobe |
| KLHI12 | Testis Intersitial |
| KLHL18 | CD105 Endothelial |
| KL11121 | Heart |
| KLHL25 | Atrioventricular Node |
| KLHL26 | Whole Brain |
| KLHL29 | Uterus Corpus |
| KLHL3 | Cerebellum |
| KLHL4 | Fetal brain |
| KLK10 | Tongue |
| KLK12 | Tongue |
| KLK13 | Tongue |
| KLK14 | Atrioventricular Node |
| KLK15 | Pancreas |
| KIK2 | Prostate |
| KLK3 | Prostate |
| KLK5 | Testis Intersitial |
| KLK7 | Pancreas |
| KLK8 | Tongue |
| KLRC3 | CD56 NK Cells |
| KLRF1 | CD56 NK Cells |
| KLRK1 | CD8 T cells |
| KNTC1 | Leukemia lymphoblastic MOLT 17 |
| KPNA4 | X721 B lymphoblasts |
| KPTN | Cerebellum |
| KRT1 | Skin |
| KRT10 | Skin |
| KRT12 | Liver |
| KRTI7 | Tongue |
| KRT2 | Skin |
| KRT23 | Colorectal adenocarcinoma |
| KRT3 | Superior Cervical Ganglion |
| KRT33A | Superior Cervical Ganglion |
| KRT34 | Skin |
| KRT36 | Superior Cervical Ganglion |
| KRT38 | Atrioventricular Node |
| KRT6B | Tongue |
| KRI84 | Superior Cervical Ganglion |
| KRT86 | Placenta |

TABLE 1-continued

List of Tissue-Specific Genes Determined
by Deconvolution of Adult Transcriptome

| Gene | Tissue |
| --- | --- |
| KRT9 | Superior Cervical Ganglion |
| KRTAP1-1 | Superior Cervical Ganglion |
| KRTAP1-3 | Ciliary Ganglion |
| KRTAP4-7 | Superior Cervical Ganglion |
| KRTAP5-9 | Superior Cervical Ganglion |
| L1TD1 | Dorsal Root Ganglion |
| L2HGDH | Superior Cervical Ganglion |
| LACTB2 | small intestine |
| LAD1 | Bronchial Epithelial Cells |
| LAIR1 | BDCA4 Dentritic Cells |
| LAIR2 | CD56 NK Cells |
| LALBA | Ovary |
| LAMA2 | Adipocyte |
| LAMA3 | Bronchial Epithelial Cells |
| LAMM4 | Smooth Muscle |
| LAMA5 | Colorectal adenocarcinoma |
| LAMB3 | Bronchial Epithelial Cells |
| LAMC2 | Bronchial Epithelial Cells |
| LANCL2 | Testis |
| LAT | CD4 T cells |
| LAX1 | CD4 T cells |
| LCAT | Liver |
| LCMT2 | CD105 Endothelial |
| LCT | Trigeminal Ganglion |
| LDB1 | CD105 Endothelial |
| LDB3 | Skeletal Muscle |
| LDHAL68 | Testis |
| LDHB | Liver |
| LDLR | Adrenal Cortex |
| LECT1 | CD105 Endothelial |
| LEF1 | Thymus |
| LEFTY1 | Colon |
| LEFTY2 | Uterus Corpus |
| LENEP | Salivary gland |
| LEP | placenta |
| LETM1 | Thymus |
| LFNG | Liver |
| LGALS13 | Placenta |
| LGALS14 | Placenta |
| LGR4 | Colon |
| LHB | Pituitary |
| LHCGR | Superior Cervical Ganglion |
| LHX2 | Fetal brain |
| LHX5 | Superior Cervical Ganglion |
| LHX6 | Fetal brain |
| LIG3 | Leukemia lymphoblastic MOLT 18 |
| LILRB4 | BDCA4 Dentritic Cells |
| LILRB5 | Skeletal Muscle |
| LIM2 | CD56 NK Cells |
| LIMS2 | Uterus |
| LIPF | small intestine |
| LIPG | Thyroid |
| LIPT1 | CD8 T cells |
| LCMD1 | Skeletal Muscle |
| LMF1 | Liver |
| LMO1 | retina |
| LMTK2 | Superior Cervical Ganglion |
| LMX1B | Superior Cervical Ganglion |
| LOC1720 | Superior Cervical Ganglion |
| LOC388796 | Lymphoma burkitts Raji |
| LOC390561 | Uterus |
| LOC390940 | Superior Cervical Ganglion |
| LOC399904 | Temporal Lobe Appendix |
| LOC441204 | Skeletal Muscle |
| LOC442421 | Superior Cervical Ganglion |
| LOC51145 | Appendix |
| LOC93432 | Ovary |
| LOH3CR2A | Appendix |
| LOR | Skin |
| LPAL2 | Uterus Corpus |
| LPAR3 | Testis germ cell |
| LIPN2 | CD71 early erythroid |
| LRAT | Pons |
| LRCH3 | CD8 T cells |
| LRDD | Pancreas |

TABLE 1-continued

List of Tissue-Specific Genes Determined
by Deconvolution of Adult Transcriptome

| Gene | Tissue |
|------|--------|
| LRFN3 | Superior Cervical Ganglion |
| LRFN4 | Fetal brain |
| LRIT1 | Superior Cervical Ganglion |
| LRP1B | Amygdala |
| LRP2 | Thyroid |
| LRP5L | Superior Cervical Ganglion |
| LRRC16A | Testis germ cell |
| LRRC17 | Smooth Muscle |
| LRRC2 | Thyroid |
| LRRC20 | Skeletal muscle |
| LRRC3 | Skeletal muscle |
| LRRC31 | Colon |
| LRRC32 | Lung |
| LRRC36 | Testis Interstitial |
| LRRC37A4 | Cerebellum |
| LRRK1 | Lymphoma burkitts Daudi |
| LST1 | Whole blood |
| LST-3TM12 | Fetal liver |
| LTB4R | CD33 Myeloid |
| LTB4R2 | Temporal Lobe |
| LTBP4 | Thyroid |
| LTC4S | Lung |
| LTK | BDCA4 Dentritic Cells |
| LUC7L | Whole blood |
| LY6D | Tongue |
| LY6E | Lung |
| LY6G5C | CD71 Early Erythroid |
| LY6G6D | Pancreas |
| LY6G6E | Ovary |
| LY6H | Amygdala |
| LY96 | Whole Blood |
| LYL1 | CD71 Early Erythroid |
| LYPD1 | Smooth muscle |
| LYST | Whole Blood |
| LYVE1 | Fetal lung |
| LYZL6 | Testis Interstitial |
| LZTFL1 | Leukemia lymphoblastic MOLT 19 |
| LZTS1 | Skeletal Muscle |
| MACROD1 | Heart |
| MAF | small intestine |
| MAFF | Placenta |
| MAFK | Superior Cervical Ganglion |
| MAGEA1 | X721 B lymphoblasts |
| MAGEA2 | Leukemia chronic Myelogenous K585 |
| MAGEA55 | X721 B lymphoblasts |
| MAGEA8 | Placenta |
| MAGEB1 | Testis Germ Cell |
| MAGEC1 | Leukemia chronic Myelogenous K586 |
| MAGEC2 | Skeletal Muscle |
| MAGED4 | Fetal brain |
| MAGEL2 | Hypothalamus |
| MAGI1 | Globus Pallidus |
| MAGIX | Superior Cervical Ganglion |
| MAGOHB | CD105 Endothelial |
| MALL | small intestine |
| MAML3 | Ovary |
| MAMLD1 | Testis Germ Cell |
| MAN1A2 | Placenta |
| MAN1C1 | Placenta |
| MAN2C1 | CD8 T cells |
| MAP2K3 | CD71 Early Erythroid |
| MAP2K5 | Globus Pallidus |
| MAP2K7 | Atrioventricular node |
| MAP3K12 | Cerebellum |
| MAP3K14 | CD19 B cells neg. sel. |
| MAP3K6 | Lung |
| MAP4K2 | X721 B lymphoblasts |
| MAPK4 | Skeletal Muscle |
| IVIAPK7 | CD56 NK Cells |
| MAPKAP1 | X721 B lymphoblasts |
| MAPKAPK3 | Heart |
| MARK2 | Globus Pallidus |
| MARK3 | CD71 Early Erythroid |
| MAS1 | Appendix |
| MASP1 | Heart |

TABLE 1-continued

List of Tissue-Specific Genes Determined
by Deconvolution of Adult Transcriptome

| Gene | Tissue |
|------|--------|
| MASP2 | Liver |
| MAST1 | Fetal brain |
| MATK | CD56 NK Cells |
| MATN1 | Trachea |
| MATN4 | Lymphoma burkitts Raji |
| MBNI3 | CD71 Early Erythroid |
| MBTPS1 | pineal night |
| MBTPS2 | Dorsal Root Ganglion |
| MC2R | Adrenal Cortex |
| MC3R | Superior Cervical Ganglion |
| MC4R | Superior Cervical Ganglion |
| MCCC2 | X721 B lymphoblasts |
| MCF2 | pineal day |
| MCM10 | CD105 Endothelial |
| MCM9 | GD19 Bcells neg. sel. |
| MCOLN3 | Adrenal Cortex |
| MCPH1 | Thymus |
| MCTP1 | Caudate nucleus |
| MCTP2 | Whole Blood |
| ME1 | Adipocyte |
| MECR | Heart |
| MED1 | Thymus |
| MED1.3 | CD8 T cells |
| MED22 | CD19 Bcells neg. sel. |
| MED31 | Cerebellum |
| MED7 | Testis Intersitial |
| MEGF6 | Lung |
| MEGF8 | Skeletal Muscle |
| MEOX2 | Fetal lung |
| MEP13 | small intestine |
| MET | Bronchial Epithelial Cells |
| METTL4 | CD8 T cells |
| METTL8 | CD19 Bcells neg. sel. |
| MEX3D | Subthalamic Nucleus |
| IVIFAPS | Adipocyte |
| MF12 | Uterus Corpus |
| MFN1 | Lymphoma burkitts Raji |
| MFSD7 | Ovary |
| MGA | CD8 T cells |
| MGAT4A | CD8 T cells |
| MGAT5 | Temporal Lobe |
| MGC29506 | Thymus |
| MGC4294 | Superior Cervical Ganglion |
| MGC5590 | Cardiac Myocytes |
| MGMT | Liver |
| MGST3 | Lymphoma burkitts Daudi |
| MIA2 | Superior Cervical Ganglion |
| MIA3 | BDCA4 Dentritic Cells |
| MCALL2 | Colorectal adenocarcinoma |
| MIER2 | Lung |
| MIEPEP | Kidney |
| MFTF | Uterus |
| MKS1 | Superior Cervical Ganglion |
| MLANA | retina |
| MLR | Testis Intersitial |
| MLH3 | Whole Blood |
| MLL2 | Liver |
| MLLT1 | Superior Cervical Ganglion |
| M1L1310 | Dorsal Root Ganglion |
| MLLT3 | CD8 T cells |
| MLN | Liver |
| MLNR | Superior Cervical Ganglion |
| MMACHC | Liver |
| MME | Adipocyte |
| N1N1P10 | Uterus Corpus |
| MMP11 | Placenta |
| MMP12 | Tonsil |
| MMP15 | Thyroid |
| N1N1P24 | Cerebellum Peduncles |
| MMP26 | Skeletal Muscle |
| MMP28 | Lung |
| MMP3 | Smooth Muscle |
| N1N1P8 | Bone marrow |
| MMP9 | Bone marrow |
| N1N1 | Fetal brain |

TABLE 1-continued

List of Tissue-Specific Genes Determined
by Deconvolution of Adult Transcriptome

| Gene | Tissue |
| --- | --- |
| MNDA | Whole Blood |
| MOBKL3 | Adrenal Cortex |
| MOCOS | Adrenal gland |
| MOCS3 | Atrioventricular Node |
| MOGAT2 | Liver |
| MON1B | Prostate |
| MORC4 | Placenta |
| MORF4L2 | Heart |
| MORN1 | Cingulate Cortex |
| MOS | Superior Cervical Ganglion |
| MOSC2 | Kidney |
| MOSPD2 | CD33 Myeloid |
| MPL | Skeletal Muscle |
| MPP3 | Cerebellum |
| MPPS | Placenta |
| MPP6 | Testis Germ Cell |
| MPPED1 | Fetal brain |
| MPPED2 | Thyroid |
| KAMA | Smooth Muscle |
| MPZL2 | Colorectal adenocarcinoma |
| MRAS | Heart |
| MREG | pineal day |
| MRPL17 | X721 B lymphoblasts |
| MRPL46 | X721 B lymphoblasts |
| MRPS18A | Heart |
| MRPS18C | Atrioventricular Node |
| MRS2 | X721 B lymphoblasts |
| MRTo4 | Leukemia promyelocytic HL64 |
| MS4A12 | Colon |
| M54A2 | Ciliary Ganglion |
| MS4A4A | Placenta |
| MS4A5 | Testis Interstial |
| MSC | X721 B lymphoblasts |
| MS114 | Uterus Corpus |
| MSLN | Lung |
| MSRA | Kidney |
| MST1 | Liver |
| MST1R | Colorectal adenocarcinoma |
| MSX1 | Colorectal adenocarcinoma |
| MT4 | Lymphoma burkitts Raji |
| MTERFD1 | CD105 Endothelial |
| MTERFD2 | CD8 T cells |
| MTF1 | CD33 Myeloid |
| MTHFSD | Testis |
| MTMR10 | CD71 Early Erythroid |
| MTMR12 | CD71 Early Erythroid |
| MTMR3 | CD71 Early Erythroid |
| MTMR4 | Placenta |
| MTMR7 | Superior Cervical Ganglion |
| MTMR8 | Skeletal Muscle |
| MTNR1A | Superior Cervical Ganglion |
| MTNR1B | Superior Cervical Ganglion |
| NITTP | small intestine |
| MUC1 | Lung |
| MUC13 | Pancreas |
| MUC16 | Trachea |
| MUC2 | Colon |
| MUCSB | Trachea |
| MUN11 | Testis |
| MUSK | Skeletal Muscle |
| MUTYH | Leukemia lymphoblastic MOLT 20 |
| MVO | Adipocyte |
| MXD1 | Whole Blood |
| MYBPC1 | Skeletal Muscle |
| MYBPC3 | Heart |
| MYBPH | Superior Cervical Ganglion |
| MYCN | Fetal brain |
| MYCT1 | Trigeminal Ganglion |
| MYF5 | Superior Cervical Ganglion |
| MYF6 | Skeletal Muscle |
| MYH1 | Skeletal Muscle |
| MYH13 | Skeletal Muscle |
| MYH1S | Appendix |
| MYHM | Superior Cervical Ganglion |
| MYL7 | Heart |

TABLE 1-continued

List of Tissue-Specific Genes Determined
by Deconvolution of Adult Transcriptome

| Gene | Tissue |
| --- | --- |
| MYNN | Trigeminal Ganglion |
| MYO16 | Fetal brain |
| MYO1A | small intestine |
| MYO1B | Bronchial Epithelial Cells |
| MYOSA | Superior Cervical Ganglion |
| MYOSC | Salivary gland |
| MYO7B | Liver |
| MYOC | retina |
| MYST2 | Testis |
| MYT1 | pineal night |
| N4BP1 | Whole Blood |
| N6AMTI | Trigeminal Ganglion |
| NAALAD2 | Pituitary |
| NAALADL1 | Liver |
| NAB2 | Cerebellum |
| NAPG | Superior Cervical Ganglion |
| NARF | CD71 Early Erythroid |
| NAT1 | Colon |
| NAT2 | Colon |
| NATS | Kidney |
| NAT8B | Kidney |
| NAV2 | Fetal brain |
| NAV3 | Fetal brain |
| NBEA | Fetal brain |
| NBEAL2 | Lymphoma burkitts Raji |
| NCAM2 | Superior Cervical Ganglion |
| NCAPG2 | CD71 Early Erythroid |
| NCBP1 | X721 B lymphoblasts |
| NCLN | BDCA4 Dentritic Cells |
| NCOA2 | Whole Blood |
| NCR1 | CD56 NK Cells |
| NCR2 | Lymphoma burkitts Raji |
| NCR3 | CD56 NK Cells |
| NDP | Amygdala |
| NDUFA4L2 | Pancreas |
| NDUFB2 | Heart |
| NDUFB7 | Heart |
| NCAB2 | Caudate nucleus |
| NE1L3 | Leukemia lymphoblastic MOLT 21 |
| NEK11 | Uterus Corpus |
| NEK3 | Pancreas |
| NEK4 | Testis Germ Cell |
| NELF | Colorectal adenocarcinoma |
| NELL1 | Whole Brain |
| NES | Olfactory Bulb |
| NETO2 | Fetal brain |
| NEU3 | Atrioventricular Node |
| NEUROD6 | Fetal brain |
| NEUROG3 | Superior Cervical Ganglion |
| NFATCI | CD19 Bcells neg. sel. |
| NFATC3 | Thymus |
| NFE2 | CD71 Early Erythroid |
| NFE2L3 | Colorectal adenocarcinoma |
| NFKB2 | Lymphoma burkitts Raji |
| NFKB1B | Testis |
| NFKBIL2 | Atrioventricular Node |
| NFX1 | BDCA4 Dentritic Cells |
| NFYA | Cardiac Myocytes |
| NGB | CD71 Early Erythroid |
| NGF | Ciliary Ganglion |
| NGFR | Colorectal adenocarcinoma |
| NHLH2 | Hypothalamus |
| NINJ1 | Whole Blood |
| NIPSNAP3B | Superior Cervical Ganglion |
| NKAIN1 | Fetal brain |
| NKX2-2 | Spinal Cord |
| NKX2-5 | Heart |
| NKX2-8 | Superior Cervical Ganglion |
| NKX3-2 | Colon |
| NKX6-1 | Skeletal Muscle |
| NLE1 | Lymphoma burkitts Raji |
| NMBR | Superior Cervical Ganglion |
| NMD3 | Bronchial Epithelial Cells |
| NME5 | Testis Interstitial |
| NMU | Leukemia chronic Myelogenous K587 |

TABLE 1-continued

List of Tissue-Specific Genes Determined
by Deconvolution of Adult Transcriptome

| Gene | Tissue |
| --- | --- |
| NMUR1 | CD56 NK Cells |
| NOC2L. | Lymphoma burkitts Raji |
| NOC3L | X721 B lymphoblasts |
| NOC4L. | Testis |
| NOLN | Superior Cervical Ganglion |
| NOL.3 | Heart |
| NOS1 | Uterus Corpus |
| NOS3 | Placenta |
| NOTCH1 | Leukemia lymphoblastic MOLT 22 |
| NOX1 | Colon |
| NOX3 | CD105 Endothelial |
| NOX4 | Kidney |
| NPAS2 | Smooth Muscle |
| NPAT | CD8 T cells |
| NPC1L1 | Fetal liver |
| NPFFR1 | Subthalamic Nucleus |
| NPHP4 | CD50 |
| NPHS2 | Kidney |
| NPM3 | Bronchial Epithelial Cells |
| NPPA | Heart |
| NPPB | Heart |
| NPPC | Superior Cervical Ganglion |
| NPTXR | Skeletal Muscle |
| NPY | Prostate |
| NPY1R | Fetal brain |
| NPUR | Superior Cervical Ganglion |
| NQ02 | Kidney |
| NR092 | Liver |
| NRID1 | pineal day |
| NR1H2 | Lung |
| NRIH4 | Fetal liver |
| NR113 | Liver |
| NR2CI | Superior Cervical Ganglion |
| NR2C2 | Testis Leydig Cell |
| NR2E1 | Amygdala |
| NR2E3 | retina |
| NR4A1 | Adrenal Cortex |
| NR4A2 | Adrenal Cortex |
| NR4A3 | Adrenal Cortex |
| NR5A1 | Globus Pallidus |
| NR6A1 | Testis |
| NRAP | Heart |
| NRAS | BDCA4 Dentritic Cells |
| NREIF2 | Whole Blood |
| NRG2 | Superior Cervical Ganglion |
| NMP2 | Olfactory Bulb |
| NRI | retina |
| NRP2 | Skeletal Muscle |
| NRTN | Superior Cervical Ganglion |
| NRXN3 | Cerebellum Peduncles |
| NSUN3 | CD71 Early Erythroid |
| NSUN6 | CD4 T cells |
| NTSDC3 | Fetal brain |
| NTSNI | CD71 Early Erythroid |
| NTAN1 | CD71 Early Erythroid |
| NTHL1 | Liver |
| NTNI | Superior Cervical Ganglion |
| NTNG1 | Uterus Corpus |
| NTSR1 | Colorectal adenocarcinoma |
| NUDT1 | CD71 Early Erythroid |
| NUDT15 | Colorectal adenocarcinoma |
| NUDT18 | CD19 Bcells neg. sel. |
| NUDT4 | CD71 Early Erythroid |
| NUDT6 | Leukemia lymphoblastic MOLT 23 |
| NUDT7 | Superior Cervical Ganglion |
| NUF1P1 | CD105 Endothelial |
| NUMB | Whole Blood |
| NUP155 | Testis Intersitial |
| NUPL1 | Fetal brain |
| NUPL2 | Colorectal adenocarcinoma |
| NXPH3 | Cerebellum |
| OAS1 | CD14 Monocytes |
| OAS2 | Lymphoma burkitts Daudi |
| OAS3 | CD33 Myeloid |
| OASL | Whole Blood |

TABLE 1-continued

List of Tissue-Specific Genes Determined
by Deconvolution of Adult Transcriptome

| Gene | Tissue |
| --- | --- |
| OAZ3 | Testis Intersitial |
| OBFC2A | Uterus Corpus |
| OBSCN | Temporal Lobe |
| OCEL1 | CD14 Monocytes |
| OCIM | Superior Cervical Ganglion |
| OCLN | Skeletal Muscle |
| ODF1 | Testis Intersitial |
| ODZ4 | Fetal brain |
| OGFRL1 | Whole Blood |
| OLAH | Placenta |
| OLFM4 | small intestine |
| OLFML3 | Adipocyte |
| OLR1 | Placenta |
| OMD | Superior Cervical Ganglion |
| OMP | Superior Cervical Ganglion |
| ONECUT1 | Liver |
| OPA3 | Colorectal adenocarcinoma |
| OPLAH | Heart |
| OPN1LW | retina |
| OPN1SW | Superior Cervical Ganglion |
| OPRD1 | Thalamus |
| OPRL1 | Lymphoma burkitts Raji |
| OR1OCI | Superior Cervical Ganglion |
| ORNH1 | Trigeminal Ganglion |
| OR1OH3 | Pons |
| °RIM | Superior Cervical Ganglion |
| OR11A1 | Superior Cervical Ganglion |
| OR1A1 | Superior Cervical Ganglion |
| ORM | Superior Cervical Ganglion |
| 0R2B6 | Superior Cervical Ganglion |
| OR2C1 | Superior Cervical Ganglion |
| OR2H1 | Skeletal Muscle |
| ORM | Superior Cervical Ganglion |
| OR2S2 | Uterus Corpus |
| OR2W1 | Superior Cervical Ganglion |
| OR3A2 | Superior Cervical Ganglion |
| OR52A1 | Testis Seminiferous Tubule |
| ORSI1 | Lymphoma burkitts Raji |
| ORRA2 | Superior Cervical Ganglion |
| OR7A5 | Appendix |
| OR7C1 | Testis Seminiferous Tubule |
| OR7E19P | Superior Cervical Ganglion |
| ORAI2 | CD19 Bcells neg. sel. |
| ORM1 | Liver |
| OSBP2 | CD71 Early Erythroid |
| OSBPL10 | CD19 Bcells neg. sel. |
| OSBPL3 | Colorectal adenocarcinoma |
| OSBPL7 | Tonsil |
| OSGEPLI | CD4 T cells |
| OSIV1 | CD71 Early Erythroid |
| OSR2 | Uterus |
| OTIJID3 | Prefrontal Cortex |
| OTIM7B | Heart |
| OXCT2 | Testis Intersitial |
| OXSM | X721 B lymphoblasts |
| OXT | Hypothalamus |
| P2RX2 | Superior Cervical Ganglion |
| P2RX3 | CD71 Early Erythroid |
| P2RX6 | Skeletal Muscle |
| P2RY10 | CD19 Bcells neg. sel. |
| P2RY2 | Bronchial Epithelial Cells |
| P2RY4 | Superior Cervical Ganglion |
| PAM | Pons |
| PAEP | Uterus |
| PAFAH2 | Thymus |
| PAGE1 | X721 B lymphoblasts |
| PAR11P1 | Prostate |
| PAK7 | Fetal brain |
| PALM | X721 B lymphoblasts |
| PALMD | Fetal liver |
| PANK4 | Lymphoma burkitts Raji |
| PANXI | Bronchial Epithelial Cells |
| PAPOLG | Fetal brain |
| PAPPA2 | Placenta |
| PAQR3 | Testis Germ Cell |

TABLE 1-continued

List of Tissue-Specific Genes Determined
by Deconvolution of Adult Transcriptome

| Gene | Tissue |
| --- | --- |
| PARD3 | Bronchial Epithelial Cells |
| PARG | Superior Cervical Ganglion |
| PARN | X721 B lymphoblasts |
| PARP11 | Appendix |
| PARP16 | Atrioventricular Node |
| PARP3 | X721 B lymphoblasts |
| PART1 | Prostate |
| PAWR | Uterus |
| PAX1 | Thymus |
| PAX2 | Kidney |
| PAX4 | Superior Cervical Ganglion |
| PAX7 | Atrioventricular Node |
| PCCA | Colon |
| PCDH1 | Placenta |
| PCDH11X | Fetal brain |
| PCDH17 | Testis Intersitial |
| PCDH7 | Prefrontal Cortex |
| PCDHB1 | Superior Cervical Ganglion |
| PCDHB11 | Uterus Corpus |
| PCDIIB13 | Pancreatic Islet |
| PCDH33 | Testis |
| PCD11B6 | Superior Cervical Ganglion |
| PCK2 | Liver |
| PCNP | Liver |
| PCNT | Skeletal Muscle |
| PCNX | CD8 T cells |
| PCNXL2 | Prefrontal Cortex |
| PCOLCE | Liver |
| PCOLCE2 | Adipocyte |
| PCSK1 | Pancreatic Islet |
| PCY0X1 | Adipocyte |
| PCYT1A | Testis |
| PDC | retina |
| PDCD1 | Pons |
| PDCD1LG2 | Superior Cervical Ganglion |
| PDE10A | Caudate nucleus |
| PDE1B | Caudate nucleus |
| PDE1C | pineal night |
| PDE3B | CD8 T cells |
| PDE6A | retina |
| PDE6G | retina |
| PDE7B | Trigeminal Ganglion |
| PDE9A | Prostate |
| PDGFRL | Fetal Thyroid |
| PDHA2 | Testis Intersitial |
| PDIA2 | Pancreas |
| PDK3 | X721 B lymphoblasts |
| PDLIM3 | Skeletal Muscle |
| PDLIM4 | Colorectal adenocarcinoma |
| PDPN | Placenta |
| PDPR | Superior Cervical Ganglion |
| PDS51 | Leukemia lymphoblastic MOLT 24 |
| PDX1 | Heart |
| PDXP | CD14 Monocytes |
| PDZD3 | Superior Cervical Ganglion |
| PDZKI1P1 | Kidney |
| PDZRN4 | Atrioventricular Node |
| PECR | Liver |
| PEPD | Kidney |
| PER3 | retina |
| PET112L | Heart |
| PEX11A | Prostate |
| PEX13 | Testis Intersitial |
| PEX19 | Adipocyte |
| PEX3 | X721 B lymphoblasts |
| PEX5L | Superior Cervical Ganglion |
| PF4 | Whole Blood |
| PF4V1 | Whole Blood |
| PFKFB1 | Liver |
| PFKFB2 | Pancreatic Islet |
| PFKFB3 | Skeletal Muscle |
| PGA3 | small intestine |
| PGAM1 | CD71 Early Erythroid |
| PGAP1 | Adrenal Cortex |
| PGGT1B | Ciliary Ganglion |

TABLE 1-continued

List of Tissue-Specific Genes Determined
by Deconvolution of Adult Transcriptome

| Gene | Tissue |
| --- | --- |
| PGK2 | Testis Intersitial |
| PGLYRP4 | Superior Cervical Ganglion |
| PGM3 | Smooth Muscle |
| PGPEP1 | Kidney |
| PGR | Uterus |
| PHACTR4 | X721 B lymphoblasts |
| PHC1 | Testis Germ Cell |
| PHEX | BDCA4 Dentritic Cells |
| PHF7 | Testis Intersitial |
| PHKG1 | Superior Cervical Ganglion |
| PHKG2 | Testis |
| PHIDA2 | Placenta |
| PHOX2A | Uterus Corpus |
| P115 | Testis Leydig Cell |
| PB | Tonsil |
| PI4K2A | CD71 Early Erythroid |
| PIAS2 | Testis Intersitial |
| PIAS3 | pineal day |
| PIAS4 | Whole Brain |
| PIBF1 | Testis Intersitial |
| PICK1 | Cerebellum Peduncles |
| PIGB | X721 B lymphoblasts |
| PIGL | Colorectal adenocarcinoma |
| MGR | Trachea |
| FIGV | Testis |
| PIGZ | Pancreas |
| PIK3C2B | Thymus |
| PIK3CA | CD8 T cells |
| PIK3R2 | Fetal brain |
| PIK3R5 | CD56 NK Cells |
| PIP5K1B | CD71 Early Erythroid |
| PIPOX | Liver |
| PIR | Bronchial Epithelial Cells |
| PITPNNI3 | Superior Cervical Ganglion |
| NTX1 | Tongue |
| P1TX2 | retina |
| P1TX3 | Adrenal gland |
| PKD2 | Uterus |
| PKDREJ | CD14 Monocytes |
| PKLR | Liver |
| PKMYT1 | CD71 Early Erythroid |
| PKP2 | Colon |
| PLAIA | X721 B lymphoblasts |
| PLA2GI2A | CD105 Endothelial |
| PLA2G2E | Superior Cervical Ganglion |
| PLA2G2F | Trigeminal Ganglion |
| PLA2G3 | Skeletal Muscle |
| PLA2G4A | Smooth Muscle |
| PLA2G7 | CD14 Monocytes |
| PLAA | X721 B lymphoblasts |
| PLACI | Placenta |
| PLAC4 | Placenta |
| PLAG1 | Trigeminal Ganglion |
| PLAGL2 | Testis |
| PLCB2 | CD14 Monocytes |
| PLCB3 | small intestine |
| PLCB4 | Thalamus |
| PLCXD1 | X721 B lymphoblasts |
| PLDI | X721 B lymphoblasts |
| PLEK2 | Bronchial Epithelial Cells |
| PLEKHA2 | Superior Cervical Ganglion |
| PLEKHA6 | Placenta |
| PLEKHA8 | CD56 NK Cells |
| PLEKHF2 | CD19 Bcells neg. sel. |
| PLEKHH3 | Superior Cervical Ganglion |
| PLK1 | X721 B lymphoblasts |
| PLK3 | CD33 Myeloid |
| PLK4 | CD71 Early Erythroid |
| PIN | Uterus |
| PLOD2 | Smooth Muscle |
| PLS1 | Colon |
| PLSCR2 | Testis Intersitial |
| PLUNC | Trachea |
| PLKNA1 | Fetal brain |
| PLXNC1 | Whole Blood |

TABLE 1-continued

List of Tissue-Specific Genes Determined
by Deconvolution of Adult Transcriptome

| Gene | Tissue |
| --- | --- |
| PMCH | Hypothalamus |
| PMCHL1 | Hypothalamus |
| PMEPA1 | Prostate |
| PNMT | Adrenal Cortex |
| PNPLA2 | Adipocyte |
| PNPLA3 | Atrioventricular Node |
| PNPLA4 | Bronchial Epithelial Cells |
| POF1B | Skin |
| POEUT2 | Smooth Muscle |
| POLE2 | Leukemia lymphoblastic MOLT 25 |
| POLL | CD71 Early Erythroid |
| POLM | CD19 Bcells neg. sel. |
| POLQ | Lymphoma burkitts Daudi |
| POLR1C | Leukemia promyelocytic H L65 |
| POLR2D | Testis |
| POLR2.1 | Trigeminal Ganglion |
| POLR3B | X721 B lymphoblasts |
| POLR3C | CD71 Early Erythroid |
| POLR3D | X721 B lymphoblasts |
| POLR3G | Leukemia promyelocytic H L66 |
| POLRIVIT | Testis |
| POM1211.2 | Superior Cervical Ganglion |
| POMC | Pituitary |
| PONIGNT1 | Heart |
| POMT1 | Testis |
| POMZP3 | Testis Germ Cell |
| PON3 | Liver |
| POP1 | Dorsal Root Ganglion |
| POPDC2 | Heart |
| POSTN | Cardiac Myocytes |
| POU2F3 | Trigeminal Ganglion |
| P0U3F3 | Superior Cervical Ganglion |
| POU3F4 | Ciliary Ganglion |
| POU4F2 | Superior Cervical Ganglion |
| POU5F1 | Pituitary |
| POU5F1P3 | Uterus Corpus |
| POU5F1P4 | Ciliary Ganglion |
| PP14571 | Placenta |
| PPAI | Heart |
| PPARD | Placenta |
| PPARG | Adipocyte |
| PPARGCIA | Salivary gland |
| PPAT | X721 B lymphoblasts |
| PPBPL2 | Superior Cervical Ganglion |
| PPCDC | X721 B lymphoblasts |
| PPEF2 | retina |
| PPRA2 | pineal day |
| PPHBPI | Colorectal adenocarcinoma |
| PP1L2 | Leukemia chronic Myelogenous K588 |
| PP1L6 | Liver |
| PPM1D | CD51 |
| PPIVI1H | Cerebellum |
| PROX | CD71 Early Erythroid |
| PPP1R12B | Uterus |
| PPP1R13B | Thyroid |
| PPP1R3D | Whole Blood |
| PPP2R2D | Whole Brain |
| PPP3R1 | Whole Blood |
| PPPSC | X721 B lymphoblasts |
| PPRC1 | CD105 Endothelial |
| PPT2 | Olfactory Bulb |
| PPY | Pancreatic Islet |
| PPY2 | Superior Cervical Ganglion |
| PQLC2 | Skeletal Muscle |
| PRAME | Leukemia chronic Myelogenous K589 |
| PRDM1 | Superior Cervical Ganglion |
| PRDM11 | CD52 |
| PRDM12 | Cardiac Myocytes |
| PRDM13 | Superior Cervical Ganglion |
| PRDM16 | Superior Cervical Ganglion |
| PRDM5 | Skeletal Muscle |
| PRDM8 | Superior Cervical Ganglion |
| PREP | X721 B lymphoblasts |
| PRF1 | CD56 NK Cells |
| PRG3 | Bone marrow |

TABLE 1-continued

List of Tissue-Specific Genes Determined
by Deconvolution of Adult Transcriptome

| Gene | Tissue |
| --- | --- |
| PR1CKLE3 | X721 B lymphoblasts |
| PRKAA1 | Testis Intersitial |
| PRKAB1 | CD71 Early Erythroid |
| PRKAB2 | Dorsal Root Ganglion |
| PRKCG | Superior Cervical Ganglion |
| PRKCH | CD56 NK Cells |
| PRKRIP1 | Colorectal adenocarcinoma |
| PRKY | CD4 T cells |
| PRL | Pituitary |
| PRLH | Trigeminal Ganglion |
| PRM2 | Testis Leydig Cell |
| PRMT3 | Leukemia promyelocytic H L67 |
| PRMT7 | BDCA4 Dentritic Cells |
| PRND | Testis Germ Cell |
| PRO1768 | Trigeminal Ganglion |
| PRO2012 | Appendix |
| PROC | Liver |
| PROCR | Placenta |
| PROL1 | Salivary gland |
| PROP1 | Trigeminal Ganglion |
| PROZ | Superior Cervical Ganglion |
| PRPS2 | Ovary |
| PRR3 | Leukemia lymphoblastic MOLT 26 |
| PRRS | CD71 Early Erythroid |
| PRR7 | X721 B lymphoblasts |
| PRRC1 | BDCA4 Dentritic Cells |
| PRRG1 | Spinal Cord |
| PRRG2 | Parietal Lobe |
| PRRG3 | Salivary gland |
| PRRX1 | Adipocyte |
| PRSS12 | Superior Cervical Ganglion |
| PRSS16 | Thymus |
| PRSS21 | Testis |
| PRSS8 | Placenta |
| PSCA | Prostate |
| PSD | Subthalamic Nucleus |
| PSGI | Placenta |
| PSG11 | Placenta |
| PSG2 | Placenta |
| PSG3 | Placenta |
| PSG4 | Placenta |
| PSGS | Placenta |
| PSGB | Placenta |
| PSG7 | Placenta |
| PSG9 | Placenta |
| PSKH1 | Testis |
| P5NIE4 | Superior Cervical Ganglion |
| PSNIDS | Leukemia chronic Myelogenous K590 |
| PSPH | Lymphoma burkitts Raji |
| PSPN | Trigeminal Ganglion |
| PSTP1P2 | Bone marrow |
| PTCH2 | Fetal brain |
| PTDSS2 | Lymphoma burkitts Raji |
| PTER | Kidney |
| PTGDR | CD56 NK Cells |
| PTGER2 | CD56 NK Cells |
| PTGES2 | X721 B lymphoblasts |
| PTGES3 | Superior Cervical Ganglion |
| PTG FR | Uterus |
| MIR | CD14 Monocytes |
| PTGS1 | Smooth Muscle |
| PTGS2 | Smooth Muscle |
| PTH2R | Superior Cervical Ganglion |
| PTHLH | Bronchial Epithelial Cells |
| PTV | BDCA4 Dentritic Cells |
| PTPLA | CD53 |
| PTPN1 | CD19 Bcells neg. sel. |
| PTPN21 | Testis |
| PTPN3 | Thalamus |
| PTPN9 | Appendix |
| PTPRG | Adipocyte |
| PTPRH | Pancreas |
| PTPRS | BDCA4 Dentritic Cells |
| PURG | Skeletal Muscle |
| PUS3 | Skeletal Muscle |

TABLE 1-continued

List of Tissue-Specific Genes Determined
by Deconvolution of Adult Transcriptome

| Gene | Tissue |
|------|--------|
| PUS7L | Superior Cervical Ganglion |
| PVALB | Cerebellum |
| PVRL3 | Placenta |
| PXDN | Smooth Muscle |
| PXN1P2 | Liver |
| PXMP4 | Lung |
| PYGM | Skeletal Muscle |
| PYGOI | Skeletal Muscle |
| MINI | Superior Cervical Ganglion |
| PYY | Colon |
| PZP | Skin |
| QPRT | Liver |
| QRSL1 | CD19 Bcells neg. sel. |
| QTRT1 | Thyroid |
| RABIIB | Thyroid |
| RAB1IF1P3 | Kidney |
| RAB17 | Liver |
| RAB23 | Uterus |
| RAB25 | Tongue |
| RAB30 | Liver |
| RAB33A | Whole Brain |
| RAB3B-8 | Bronchial Epithelial Cells |
| RAB3D | Atrioventricular Node |
| RAB40A | Dorsal Root Ganglion |
| RAB40C | Superior Cervical Ganglion |
| RAB4B | BDCA4 Dentritic Cells |
| RABL2A | Fetal brain |
| RAC3 | Whole Brain |
| RAD51L1 | Superior Cervical Ganglion |
| RADS2 | Lymphoma burkitts Raji |
| RAD9A | CD105 Endothelial |
| RAGI | Thymus |
| RALG PSI | Fetal brain |
| RAMP1 | Uterus |
| RAMP2 | Lung |
| RAMP3 | Lung |
| RANBP10 | CD71 Early Erythroid |
| RANBP17 | Colorectal adenocarcinoma |
| RAP2C | Uterus |
| RAPGEF1 | Uterus Corpus |
| RAPGEF4 | Amygdala |
| RAPGER1 | Whole Brain |
| RAPSN | Skeletal Muscle |
| RARA | Whole Blood |
| RARB | Superior Cervical Ganglion |
| RAM | Uterus Corpus |
| RASA1 | Placenta |
| RASA2 | CD8 T cells |
| RASA3 | CD56 NK Cells |
| RASAL1 | Lymphoma burkitts Raji |
| RASGRF1 | Cerebellum |
| RASGRP3 | CD19 Bcells neg. sel. |
| RAS5F7 | Pancreas |
| RASSF8 | Testis Intersitial |
| RASSF9 | Appendix |
| RAVER2 | Ciliary Ganglion |
| RAX | Cerebellum Peduncles |
| RBBPS | CD14 Monocytes |
| 1161V119 | Superior Cervical Ganglion |
| RBIV14B | Fetal brain |
| MVP' | Whole Blood |
| Mk/MAI | Testis |
| RBP4 | Liver |
| RBPJL | Pancreas |
| REX1 | CD71 Early Erythroid |
| RC3H2 | BDCA4 Dentritic Cells |
| RCAN3 | Prostate |
| RCBTB2 | Leukemia lymphoblastic MOLT 27 |
| RCN3 | Smooth Muscle |
| RDH11 | Prostate |
| RDH16 | Liver |
| RD118 | retina |
| RECQL4 | CD105 Endothelial |
| RECOL5 | Skeletal Muscle |
| RELB | Lymphoma burkitts Raji |

TABLE 1-continued

List of Tissue-Specific Genes Determined
by Deconvolution of Adult Transcriptome

| Gene | Tissue |
|------|--------|
| REN | Ovary |
| RENBP | Kidney |
| RERGL | Uterus |
| RETSAT | Adipocyte |
| REV3L | Uterus |
| REX04 | CD19 Bcells neg. sel. |
| RFC1 | Leukemia lymphoblastic MOLT 28 |
| RFC2 | X721 B lymphoblasts |
| RFNG | Liver |
| RFPL3 | Superior Cervical Ganglion |
| RFWD3 | CD105 Endothelial |
| RFX1 | Superior Cervical Ganglion |
| RFX3 | Trigeminal Ganglion |
| RFXAP | Pituitary |
| RGN | Adrenal gland |
| RGPDS | Testis Intersitial |
| RGR | retina |
| RGS14 | Caudate nucleus |
| RGS17 | Pancreatic Islet |
| RGS3 | Heart |
| RGS6 | pineal night |
| RG59 | Caudate nucleus |
| RHAG | CD71 Early Erythroid |
| RHBDF1 | Olfactory Bulb |
| RHBDL1 | Lymphoma burkitts Raji |
| RHBG | Atrioventricular Node |
| RHCE | CD71 Early Erythroid |
| RHD | CD71 Early Erythroid |
| RHO | retina |
| RHOBTBI | Placenta |
| RHOBTB2 | Lung |
| RHOD | Bronchial Epithelial Cells |
| RiBC2 | Testis Intersitial |
| R1C3 | Cingulate Cortex |
| RIC8B | Caudate nucleus |
| R1N3 | CD14 Monocytes |
| RNT1 | Superior Cervical Ganglion |
| RIOK2 | Smooth Muscle |
| RIT1 | Whole Blood |
| RIT2 | Fetal brain |
| RLBP1 | retina |
| RLN1 | Prostate |
| RLN2 | Superior Cervical Ganglion |
| RMI1 | X721 B lymphoblasts |
| RMNDI | Trigeminal Ganglion |
| RMND5A | CD71 Early Erythroid |
| RMND5B | Testis |
| RNASE3 | Bone marrow |
| RNASEH2B | Leukemia lymphoblastic MOLT 29 |
| RNASEL | Whole Blood |
| RNF10 | CD71 Early Erythroid |
| RNF121 | Subthalamic Nucleus |
| RNF123 | CD71 Early Erythroid |
| RNF125 | CD8 T cells |
| RNF14 | CD71 Early Erythroid |
| RNF141 | Testis Intersitial |
| RNF17 | Testis Intersitial |
| RNF170 | Thyroid |
| RNF185 | Superior Cervical Ganglion |
| RNF19A | CD71 Early Erythroid |
| RNF32 | Testis Intersitial |
| RNF40 | CD71 Early Erythroid |
| RNFT1 | Testis Leydig Cell |
| RN Mill | Testis |
| ROB01 | Fetal brain |
| ROPN1 | Testis Intersitial |
| ROR1 | Adipocyte |
| RORB | Superior Cervical Ganglion |
| RORC | Liver |
| RP2 | Whole Blood |
| RPA4 | Superior Cervical Ganglion |
| RPAIN | Lymphoma burkitts Daudi |
| RPE | Leukemia promyelocytic H L68 |
| RPE65 | retina |
| RPGRIP1 | Testis Intersitial |

TABLE 1-continued

List of Tissue-Specific Genes Determined
by Deconvolution of Adult Transcriptome

| Gene | Tissue |
|------|--------|
| RPGRIP11 | Superior Cervical Ganglion |
| RPH3AL | Pancreatic Islet |
| RPL101 | Testis |
| RPL3L | Skeletal Muscle |
| RPP38 | Testis Germ Cell |
| RPRIV1 | Fetal brain |
| RPS6KA4 | Pons |
| RPS6KA6 | Appendix |
| RPS6KB1 | CD4 T cells |
| RPS6KC1 | Testis Intersitial |
| RRAD | Skeletal Muscle |
| RRAGB | Superior Cervical Ganglion |
| RRH | retina |
| RRH3 | CD56 NK Cells |
| RRP12 | CD33 Myeloid |
| RRP9 | X721 B lymphoblasts |
| RS1 | retina |
| RSAD2 | CD71 Early Erythroid |
| RSF1 | Uterus |
| RTDR1 | Testis |
| RTN2 | Skeletal Muscle |
| RUNX1T1 | Fetal brain |
| RUNX2 | Pons |
| RWDD2A | Testis Germ Cell |
| RXFP3 | Superior Cervical Ganglion |
| RYR2 | Prefrontal Cortex |
| S100A12 | Bone marrow |
| S100A2 | Bronchial Epithelial Cells |
| S100A3 | Colorectal adenocarcinoma |
| SUMAS | Liver |
| SIOOG | Uterus Corpus |
| S1PRS | CD56 NK Cells |
| SAA1 | Salivary gland |
| SAA3P | Skin |
| SAA4 | Liver |
| SAC3D1 | Testis |
| SAG | retina |
| SAMHD1 | CD33 Myeloid |
| SAMSN1 | Leukemia chronic Myelogenous K591 |
| SARIB | small intestine |
| SARDH | Liver |
| SATB2 | Fetal brain |
| SBNO1 | Appendix |
| SCAMP3 | Atrioventricular Node |
| SCAND2 | Superior Cervical Ganglion |
| SCAPER | Fetal brain |
| SCARA3 | Uterus Corpus |
| SCGB1D2 | Skin |
| SCGB2A2 | Skin |
| SCGN | Pancreatic Islet |
| SON | Trigeminal Ganglion |
| SCLY | Liver |
| SCN3A | Fetal brain |
| SCN4A | Skeletal Muscle |
| SCNSA | Heart |
| SCN8A | Superior Cervical Ganglion |
| SCNN1B | Lung |
| SCNN1D | Superior Cervical Ganglion |
| SCO2 | CD33 Myeloid |
| SCRH3 | Heart |
| SCRT1 | Superior Cervical Ganglion |
| SCT | BDCA4 Dentritic Cells |
| SCUIBE3 | Superior Cervical Ganglion |
| SCYL2 | BDCA4 Dentritic Cells |
| SOU | BDCA4 Dentritic Cells |
| SDCCAG3 | Lymphoma burkitts Raji |
| SDF2 | Whole Blood |
| SDPR | Fetal lung |
| SDS | Liver |
| SEC1413 | Trigeminal Ganglion |
| SEC14L4 | CD71 Early Erythroid |
| SEC22B | Placenta |
| SECTN11 | Whole Blood |
| SEL1L | Pancreas |
| SELE | retina |

TABLE 1-continued

List of Tissue-Specific Genes Determined
by Deconvolution of Adult Transcriptome

| Gene | Tissue |
|------|--------|
| SELP | Whole Blood |
| SEMA3A | Appendix |
| SEMA3B | Placenta |
| SEMA3D | Trigeminal Ganglion |
| SEMA34G | Fetal liver |
| SEMA5A | Olfactory Bulb |
| SEMA7A | Superior Cervical Ganglion |
| SEMGI | Prostate |
| SEMG2 | Prostate |
| SENP2 | Testis Intersitial |
| SEPHS1 | Leukemia lymphoblastic MOLT 30 |
| SERPINA10 | Liver |
| SERPINA7 | Fetal liver |
| SERPINB13 | Tongue |
| SERPINB3 | Trachea |
| SERPINB4 | Superior Cervical Ganglion |
| SERPINB8 | CD33 Myeloid |
| SERPINEI | Cardiac Myocytes |
| SERPiNF2 | Liver |
| SETD4 | Testis |
| SETD8 | CD71 Early Erythroid |
| SETMAR | Atrioventricular Node |
| SF3A3 | Leukemia chronic Myelogenous K592 |
| SRAM | Testis Germ Cell |
| SFRIPS | retina |
| SFTPA2 | Lung |
| SFTPD | Lung |
| 5GCA | Heart |
| SGCB | Olfactory Bulb |
| SIGMA | Colorectal adenocarcinoma |
| SGPPI | Placenta |
| SGTA | Heart |
| SH2DIA | Leukemia lymphoblastic MOLT 31 |
| SH2D3C | Thymus |
| SH3BGR | Skeletal Muscle |
| SH3TC1 | Thymus |
| SH3TC2 | Placenta |
| SHANK1 | CD56 NK Cells |
| SHC2 | Pancreatic Islet |
| SHC3 | Prefrontal Cortex |
| SHH | Superior Cervical Ganglion |
| SHOX2 | Thalamus |
| SHQ1 | Leukemia lymphoblastic MOLT 32 |
| SHROOM2 | pineal night |
| Si | small intestine |
| SIAill | Placenta |
| SiAH2 | CD71 Early Erythroid |
| SIGLEC1 | Lymph node |
| SiGLECS | Superior Cervical Ganglion |
| SIGLEC6 | Placenta |
| SILV | retina |
| SIM1 | Superior Cervical Ganglion |
| SIM2 | Skeletal Muscle |
| SIRPB1 | Whole Blood |
| SIRT1 | CD19 Bcells neg. sel. |
| SIRT4 | Superior Cervical Ganglion |
| SIRT5 | Heart |
| SIRT7 | CD33 Myeloid |
| SIX1 | Pituitary |
| SIX2 | Pituitary |
| SIX3 | retina |
| SIX5 | Superior Cervical Ganglion |
| SKAP1 | CD8 T cells |
| SLAMF1 | X721 B lymphoblasts |
| SLC10A1 | Liver |
| SLC10A2 | small intestine |
| SLC12A1 | Kidney |
| SLC12A2 | Trachea |
| SLC12A6 | Testis Intersitial |
| SLC12A9 | CD14 Monocytes |
| SLC13A2 | Kidney |
| SLC13A3 | Kidney |
| SLC13A4 | pineal night |
| SLC14A1 | CD71 Early Erythroid |
| SLC15A1 | Superior Cervical Ganglion |

TABLE 1-continued

List of Tissue-Specific Genes Determined
by Deconvolution of Adult Transcriptome

| Gene | Tissue |
|---|---|
| SLC16A10 | Superior Cervical Ganglion |
| SLC16A4 | Placenta |
| SLC16A8 | retina |
| SLC17A1 | Superior Cervical Ganglion |
| SLC17A3 | Kidney |
| SLC17A4 | Superior Cervical Ganglion |
| SLUMS | Placenta |
| SLC18A1 | Skeletal Muscle |
| SLC18A2 | Uterus |
| SLC19A2 | Adrenal Cortex |
| SLC19A3 | Placenta |
| SLC1A5 | Colorectal adenocarcinoma |
| SLC1A6 | Cerebellum |
| SLC1A7 | Trigeminal Ganglion |
| SLC20A2 | Thyroid |
| SLC22A1 | Liver |
| SLC22A13 | Superior Cervical Ganglion |
| SLC22A18AS | Lymphoma burkitts Raji |
| SLC22A2 | Kidney |
| SLC22A3 | Prostate |
| SLC22A4 | CD71 Early Erythroid |
| SLC22A6 | Kidney |
| SLC22A7 | Liver |
| SLC22A8 | Kidney |
| SLC24A1 | retina |
| SLC24A2 | Ciliary Ganglion |
| SLC24A6 | Adrenal gland |
| SLC25A10 | Liver |
| SLC25A11 | Heart |
| SLC25A17 | X721 B lymphoblasts |
| SLC25A21 | Leukemia chronic Myelogenous K593 |
| SLC25A28 | BDCA4 Dentritic Cells |
| SLC25A31 | Testis |
| SLC25A37 | Bone marrow |
| SLC25A38 | CD71 Early Erythroid |
| SLC25A4 | Skeletal Muscle |
| SLC25A42 | Superior Cervical Ganglion |
| SLC26A2 | Colon |
| SLC26A3 | Colon |
| SLC26A4 | Thyroid |
| SLC26A6 | Leukemia lymphoblastic MOLT 33 |
| SLC27A2 | Kidney |
| SLC27A5 | Liver |
| SLC27A6 | Olfactory Bulb |
| S1C28A3 | Pons |
| SLC29A1 | CD71 Early Erythroid |
| SLC2A1I | pineal day |
| SLC2A14 | Colorectal adenocarcinoma |
| SLC2A2 | Fetal liver |
| SLC2A6 | CD14 Monocytes |
| SLC30A110 | Fetal liver |
| SLC31A1 | CD105 Endothelial |
| SLC33A1 | BDCA4 Dentritic Cells |
| SLC34A1 | Kidney |
| 5LC35A3 | Colon |
| SLC35C1 | Colorectal adenocarcinoma |
| SLC35E3 | Prostate |
| SLC37A1 | X721 B lymphoblasts |
| SLC37A4 | Liver |
| SLC38A3 | Liver |
| SLC38A4 | Fetal liver |
| SLC38A6 | CD105 Endothelial |
| SLC38A7 | Prefrontal Cortex |
| SLC39A7 | Prostate |
| SLC3A1 | Kidney |
| SLC41A3 | Testis |
| SLC45A2 | retina |
| SLC47,41 | Adrenal Cortex |
| SLC4A1 | CD71 Early Erythroid |
| SLC4A3 | Heart |
| SLC5A1 | small intestine |
| SLC5A2 | Kidney |
| SLC5A4 | Superior Cervical Ganglion |
| SLCSA5 | Thyroid |
| SLC5A6 | Placenta |

TABLE 1-continued

List of Tissue-Specific Genes Determined
by Deconvolution of Adult Transcriptome

| Gene | Tissue |
|---|---|
| SLC6A11 | Skeletal Muscle |
| SLC6AI2 | Kidney |
| SLC6A14 | Fetal lung |
| SLC6A15 | Bronchial Epithelial Cells |
| SLC6A20 | Trigeminal Ganglion |
| SLC6A4 | pineal night |
| SLC6A7 | Superior Cervical Ganglion |
| SLC6A9 | CD71 Early Erythroid |
| SLC9A1 | Placenta |
| SLC9A3 | Superior Cervical Ganglion |
| SLC9A5 | Prefrontal Cortex |
| SLC9A8 | CD33 Myeloid |
| SLCO2B1 | Liver |
| SLCO4C1 | Ciliary Ganglion |
| SLCO5A1 | X721 B lymphoblasts |
| SLFN12 | CD33 Myeloid |
| SLIT1 | Leukemia lymphoblastic MOLT 34 |
| SLIT3 | Adipocyte |
| SLITRK3 | Subthalamic Nucleus |
| SLMO1 | Superior Cervical Ganglion |
| SLURP1 | Tongue |
| SMC2 | Leukemia lymphoblastic MOLT 35 |
| SMCHD1 | Whole Blood |
| SMCP | Testis Intersitial |
| SMG6 | Appendix |
| SMR3A | Salivary gland |
| SMR3B | Salivary gland |
| SMURF1 | Testis |
| SMYD3 | Leukemia chronic Myelogenous K594 |
| SMYDS | Pancreas |
| SNAPC1 | Testis Intersitial |
| SNAPC4 | Testis |
| SNCA1P | Uterus Corpus |
| SN1P1 | Globus Pallidus |
| SNX1 | Fetal Thyroid |
| SNX16 | Trigeminal Ganglion |
| SNX19 | Superior Cervical Ganglion |
| SNX2 | CD19 Bcells neg. sel. |
| SNX24 | Spinal Cord |
| SOATI | Adrenal gland |
| SOAT2 | Fetal liver |
| SOCSI | Lymphoma burkitts Raji |
| SOCS2 | Leukemia chronic Myelogenous K595 |
| SOCS6 | Colon |
| SOD3 | Thyroid |
| SOHLH2 | X721 B lymphoblasts |
| SOS1 | Adipocyte |
| SOSTDC1 | retina |
| SOX1 | Superior Cervical Ganglion |
| SOX11 | Fetal brain |
| SOX12 | Fetal brain |
| S0X18 | Superior Cervical Ganglion |
| SOX5 | Testis Intersitial |
| SP140 | CD19 Bcells neg. sel. |
| SPA17 | Testis Intersitial |
| SPAG1 | Appendix |
| SPAG11B | Testis Leydig Cell |
| SPAG6 | Testis |
| SPANXBI | Testis Seminiferous Tubule |
| SPAST | Fetal brain |
| SPATA2 | Testis |
| SPATA5L1 | Leukemia promyelocytic HL69 |
| SPATA6 | Testis Intersitial |
| SPC25 | Leukemia chronic Myelogenous K596 |
| SPCS3 | BDCA4 Dentritic Cells |
| SPDEF | Prostate |
| SPEG | Uterus |
| SPIB | Lymphoma burkitts Raji |
| SP1NT3 | Testis Germ Cell |
| SPO11 | Trigeminal Ganglion |
| SPPL2B | CD54 |
| SPR | Liver |
| SPRED2 | Thymus |
| SRD5A1 | Fetal brain |
| SRD5A2 | Liver |

TABLE 1-continued

List of Tissue-Specific Genes Determined
by Deconvolution of Adult Transcriptome

| Gene | Tissue |
|------|--------|
| SRERF1 | Adrenal Cortex |
| SRF | CD71 Early Erythroid |
| SRR | Superior Cervical Ganglion |
| SSH3 | Bronchial Epithelial Cells |
| SSR3 | Prostate |
| SSSCA1 | CD105 Endothelial |
| SST | Pancreatic Islet |
| SSTR1 | Atrioventricular Node |
| SSTR4 | Ciliary Ganglion |
| SSTR5 | Subthalamic Nucleus |
| SSX2 | Superior Cervical Ganglion |
| MS | Liver |
| ST3GALI | CD8 T cells |
| ST6GALNAC4 | CD71 Early Erythroid |
| ST7 | X721 B lymphoblasts |
| ST7L | Ovary |
| ST8SIA2 | Superior Cervical Ganglion |
| ST8SIA4 | Whole Blood |
| ST8SIA5 | Adrenal gland |
| STAB2 | Lymph node |
| STAC | Ciliary Ganglion |
| STAG3L4 | Appendix |
| STAM2 | Testis Intersitial |
| STARD13 | X721 B lymphoblasts |
| STARDS | Uterus Corpus |
| STAT2 | BDCA4 Dentritic Cells |
| STAT5A | Leukemia lymphoblastic MOLT 36 |
| STBDI | Pancreatic Islet |
| STC1 | Smooth Muscle |
| STEAP1 | Prostate |
| STEAP3 | CD71 Early Erythroid |
| STIL | Trigeminal Ganglion |
| STK11 | CD71 Early Erythroid |
| STK16 | X721 B lymphoblasts |
| STMN3 | Amygdala |
| STON1 | Uterus |
| STRN | Ciliary Ganglion |
| STRN3 | Uterus |
| STS | Placenta |
| STX17 | Superior Cervical Ganglion |
| STX2 | CD8 T cells |
| STX3 | Whole Blood |
| STX6 | Whole Blood |
| STYK1 | Trigeminal Ganglion |
| SUCLG1 | Kidney |
| SULT1A3 | Ciliary Ganglion |
| SULT2A1 | Adrenal gland |
| SULT2B1 | Tongue |
| SUOX | Liver |
| SUPT3H | Testis Seminiferous Tubule |
| SUPV3L1 | Leukemia promyelocytic HL70 |
| SURF2 | Testis Germ Cell |
| SUV39H1 | CD71 Early Erythroid |
| SVEP1 | Placenta |
| SYCP1 | Testis Intersitial |
| SYCP2 | Testis Leydig Cell |
| SYDE1 | Placenta |
| SYF2 | Skeletal Muscle |
| SYN3 | Skeletal Muscle |
| SYNGR4 | Testis |
| SYNPO2L | Heart |
| SYP | pineal night |
| SYT12 | Trigeminal Ganglion |
| T | X721 B lymphoblasts |
| TAAR3 | Superior Cervical Ganglion |
| TAAR5 | Superior Cervical Ganglion |
| TAC1 | Caudate nucleus |
| TAC3 | Placenta |
| TACR3 | Pancreas |
| TAF4 | Leukemia lymphoblastic MOLT 37 |
| TAF5L | CD71 Early Erythroid |
| TAF7L | Testis Germ Cell |
| TAL1 | CD71 Early Erythroid |
| TANC2 | Superior Cervical Ganglion |
| TAP2 | CD56 NK Cells |

TABLE 1-continued

List of Tissue-Specific Genes Determined
by Deconvolution of Adult Transcriptome

| Gene | Tissue |
|------|--------|
| TARBP1 | CD55 |
| TAS2R1 | Globus Pallidus |
| TAS2R14 | Superior Cervical Ganglion |
| TAS2R7 | Superior Cervical Ganglion |
| TAS2R9 | Subthalamic Nucleus |
| TASP1 | Superior Cervical Ganglion |
| TAT | Liver |
| TBC1D12 | Spinal Cord |
| TBC1D13 | Kidney |
| TBC1D16 | Adipocyte |
| TBC1D22A | CD19 Bcells neg. sel. |
| TBC1D22B | CD71 Early Erythroid |
| TBC1D29 | Dorsal Root Ganglion |
| TBC1D8B | Pituitary |
| TBCA | Superior Cervical Ganglion |
| TBCD | Leukemia lymphoblastic MOLT 38 |
| TBCE | CD56 |
| TBL1Y | Superior Cervical Ganglion |
| TBL2 | Testis |
| TBP | Testis Intersitial |
| TBRG4 | Lymphoma burkitts Raji |
| TBX10 | Skeletal Muscle |
| TBX19 | Pituitary |
| TBX21 | CD56 NK Cells |
| TBX3 | Adrenal gland |
| TBX4 | Temporal Lobe |
| TBX5 | Superior Cervical Ganglion |
| TCHH | Placenta |
| TCL1B | Atrioventricular Node |
| TUG | Cardiac Myocytes |
| TCN2 | Kidney |
| TCP11 | Testis Intersitial |
| TDPI | Testis Intersitial |
| TEAD3 | Placenta |
| TEAD4 | Colorectal adenocarcinoma |
| TEC | Liver |
| TECTA | Superior Cervical Ganglion |
| TESK2 | CD19 Bcells neg. sel. |
| TEX13B | Skeletal Muscle |
| TEXI4 | Testis Seminiferous Tubule |
| TEX15 | Testis Seminiferous Tubule |
| TEX28 | Testis |
| TFAP2A | Placenta |
| TFAP2B | Skeletal Muscle |
| TFAP2C | Placenta |
| TFBIM | Leukemia promyelocytic HL71 |
| TF32M1 | Leukemia chronic Myelogenous K597 |
| TFCP21.1 | Salivary gland |
| TFDPI | CD71 Early Erythroid |
| TFDP3 | Superior Cervical Ganglion |
| TFEC | CD33 Myeloid |
| TFF3 | Pancreas |
| TFR2 | Liver |
| TGDS | Pancreas |
| TGFB1I1 | Uterus |
| TGM2 | Placenta |
| TGM3 | Tongue |
| TGM4 | Prostate |
| TGM5 | Liver |
| TGS1 | CD105 Endothelial |
| THADA | CD4 T cells |
| THAPIO | Whole Brain |
| THAP3 | Lymphoma burkitts Raji |
| THBS3 | Testis |
| THG1L | CD105 Endothelial |
| THNSL2 | Liver |
| THRB | Superior Cervical Ganglion |
| THSD1 | Pancreas |
| THSD4 | Superior Cervical Ganglion |
| THSD7A | Placenta |
| THUMPD2 | Leukemia lymphoblastic MOLT 39 |
| TIMM22 | Whole Brain |
| TIMM50 | Skin |
| TIMM8B | Heart |
| TIMP2 | Placenta |

TABLE 1-continued

List of Tissue-Specific Genes Determined
by Deconvolution of Adult Transcriptome

| Gene | Tissue |
| --- | --- |
| TLE3 | Whole Blood |
| TLE6 | CD71 Early Erythroid |
| TLL1 | Superior Cervical Ganglion |
| TIL2 | Heart |
| TLR3 | Testis Intersitial |
| TIR7 | BDCA4 Dentritic Cells |
| TLX3 | Cardiac Myocytes |
| TM4SF20 | small intestine |
| TM4SF5 | Liver |
| TM7SE2 | Adrenal gland |
| TMCC1 | Pancreas |
| TMCC2 | CD71 Early Erythroid |
| TMCO3 | Smooth Muscle |
| TMEM104 | Skin |
| TMEM11 | CD71 Early Erythroid |
| TMEM110 | Liver |
| TMEM121 | CD14 Monocytes |
| TMEM135 | Adipocyte |
| TMEM140 | Whole Blood |
| TMEM149 | BDCA4 Dentritic Cells |
| TMEM159 | Heart |
| TMEM186 | X721 B lymphoblasts |
| TMEM187 | Lung |
| TMEM19 | Superior Cervical Ganglion |
| TMEM2 | Placenta |
| TMEM209 | Superior Cervical Ganglion |
| TMEM39A | Pituitary |
| TMEM45A | Skin |
| TMEM48 | X721 B lymphoblasts |
| TMEM53 | Liver |
| TMEM57 | CD71 Early Erythroid |
| TMEM62 | Cingulate Cortex |
| TMEM63A | GD4 T cells |
| TMEM70 | Skeletal Muscle |
| TMLHE | Superior Cervical Ganglion |
| TMPRSS2 | Prostate |
| TMPRSS3 | small intestine |
| TMPRSS5 | Olfactory Bulb |
| TMPRSS6 | Liver |
| TNFAIP6 | Smooth Muscle |
| TNRSF10C | Whole Blood |
| TNFRSF1OD | Cardiac Myocytes |
| TNFR5F11A | Appendix |
| TNFRSF11B | Thyroid |
| TNFRSF14 | Lymphoma burkitts Raji |
| TNFRSF25 | CD4 T cells |
| TNFRSF4 | Lymph node |
| TNFRSF8 | X721 B lymphoblasts |
| TNFRSF9 | Ciliary Ganglion |
| TNFSF11 | Lymph node |
| TNFSF14 | X721 B lymphoblasts |
| TNFSF8 | CD4 T cells |
| TNE5F9 | Leukemia promyelocytic HL72 |
| TNIP2 | Lymphoma burkitts Raji |
| TNN | pineal night |
| TNNI1 | Skeletal Muscle |
| TNN13 | Heart |
| INNI3K | Superior Cervical Ganglion |
| TNNT1 | Skeletal Muscle |
| INNT2 | Heart |
| TNP1 | Testis Intersitial |
| TNP2 | Testis Intersitial |
| TNR | Skeletal Muscle |
| TNS4 | Colorectal adenocarcinoma |
| TNXA | Adrenal Cortex |
| TNXB | Adrenal Cortex |
| TOMEI | Bronchial Epithelial Cells |
| TOMM22 | X721 B lymphoblasts |
| TOP3B | Leukemia chronic Myelogenous K598 |
| TOX3 | Colon |
| TOX4 | Superior Cervical Ganglion |
| TP53BP1 | pineal night |
| TP73 | Skeletal Muscle |
| TPPP3 | Placenta |
| TPSAI31 | Lung |

TABLE 1-continued

List of Tissue-Specific Genes Determined
by Deconvolution of Adult Transcriptome

| Gene | Tissue |
| --- | --- |
| TRABD | BDCA4 Dentritic Cells |
| TRADD | CD4 T cells |
| TRAF1 | X721 B lymphoblasts |
| TRAF2 | Lymphoma burkitts Raji |
| TRAF31P2 | Bronchial Epithelial Cells |
| TRAF6 | Leukemia chronic Myelogenous K599 |
| TRAK1 | CD19 Bcells neg. sel. |
| TRAK2 | CD71 Early Erythroid |
| TRDMT1 | Superior Cervical Ganglion |
| TRDN | Tongue |
| TREH | Kidney |
| TREML2 | Placenta |
| TRH | Hypothalamus |
| TR1M10 | CD71 Early Erythroid |
| TR1M13 | Testis Intersitial |
| TRINUS | Pancreas |
| TR1M17 | Ciliary Ganglion |
| TR1M21 | Whole Blood |
| TR1M23 | Amygdala |
| TRIM25 | Placenta |
| TR1M29 | Tongue |
| TR1M31 | Skeletal Muscle |
| TR1N132 | Cerebellum |
| TRIM36 | Amygdala |
| TR1N146 | CD71 Early Erythroid |
| TRIM68 | CD56 NK Cells |
| TRIO | Fetal brain |
| TRIP10 | Skeletal Muscle |
| TRIP11 | Testis Intersitial |
| TRIVIT12 | CD105 Endothelial |
| TRIVILJ | CD8 T cells |
| TRPAI | Superior Cervical Ganglion |
| IRKS | Superior Cervical Ganglion |
| TRPIVI1 | retina |
| TRPM2 | BDCA4 Dentritic Cells |
| TRPIVIS | Skeletal Muscle |
| TRPV4 | Superior Cervical Ganglion |
| TRRAP | Leukemia lymphoblastic MOLT 40 |
| TSGA10 | Testis Intersitial |
| TSHB | Pituitary |
| TSKS | Testis Intersitial |
| TSPAN1 | Trachea |
| TSPAN15 | Olfactory Bulb |
| TSPAN32 | CD8 T cells |
| TSPANS | CD71 Early Erythroid |
| TSPAN9 | Heart |
| ISSC4 | Heart |
| TSTA3 | CD105 Endothelial |
| TTC15 | Testis Intersitial |
| TTC22 | Superior Cervical Ganglion |
| TTC23 | Lymphoma burkitts Raji |
| TTC27 | Leukemia chronic Myelogenous K600 |
| TTC28 | Fetal brain |
| TTC9 | Fetal brain |
| TTLL12 | CD105 Endothelial |
| TTLLA | Testis |
| TTLL5 | Testis Intersitial |
| TTPA | Atrioventricular Node |
| TTTY9A | Superior Cervical Ganglion |
| TIMM | Lymphoma burkitts Raji |
| TUBAB | Superior Cervical Ganglion |
| TUBAL3 | small intestine |
| TUBB40 | Skeletal Muscle |
| TUBD1 | Superior Cervical Ganglion |
| TUFM | Superior Cervical Ganglion |
| TUFT1 | Skin |
| TWSG1 | Smooth Muscle |
| TYR | retina |
| TYRP1 | retina |
| U2AF1 | Superior Cervical Ganglion |
| UAP1L1 | X721 B lymphoblasts |
| UBA1 | Superior Cervical Ganglion |
| UBE2D1 | Whole Blood |
| UBE2D4 | Liver |
| U3FD1 | CD105 Endothelial |

TABLE 1-continued

List of Tissue-Specific Genes Determined
by Deconvolution of Adult Transcriptome

| Gene | Tissue |
|---|---|
| UBQLN3 | Testis Intersitial |
| UCN | pineal night |
| UCP1 | Fetal Thyroid |
| UFC1 | Trigeminal Ganglion |
| UGT2A1 | Atrioventricular Node |
| UGT2B15 | Liver |
| UGT2B17 | Appendix |
| ULBP1 | Cerebellum |
| ULBP2 | Bronchial Epithelial Cells |
| UMOD | Kidney |
| UNC119 | Lymphoma burkitts Raji |
| UNC5C | Superior Cervical Ganglion |
| UNC93A | Fetal liver |
| UNC93B1 | BDCA4 Dentritic Cells |
| UPB1 | Liver |
| UPF1 | Prostate |
| UPK1A | Prostate |
| UPK1B | Trachea |
| UPK3A | Prostate |
| UPK3B | Lung |
| UPP1 | Bronchial Epithelial Cells |
| UQCC | Lymphoma burkitts Raji |
| UCICRC1 | Heart |
| UQCRFS1 | Superior Cervical Ganglion |
| URM1 | Heart |
| UROD | CD71 Early Erythroid |
| USH2A | pineal day |
| USP10 | Whole Blood |
| USP12 | CD71 Early Erythroid |
| USP13 | Skeletal Muscle |
| USP18 | X721 B lymphoblasts |
| USP19 | Trigeminal Ganglion |
| USP2 | Testis Germ Cell |
| USP27X | Superior Cervical Ganglion |
| USP29 | Superior Cervical Ganglion |
| U5P32 | Testis Intersitial |
| USPCNL | Atrioventricular Node |
| UTRN | Testis Intersitial |
| UTS2 | CD56 NK Cells |
| UTY | Ciliary Ganglion |
| UVRAG | CD19 Bcells neg. sel. |
| VAC14 | Skeletal Muscle |
| VARS | X721 B lymphoblasts |
| VASH1 | pineal night |
| VASH2 | Fetal brain |
| VASP | Whole Blood |
| VAV2 | CD19 Bcells neg. sel. |
| VAV3 | Placenta |
| VAX2 | Superior Cervical Ganglion |
| VCPIP1 | CD33 Myeloid |
| VENTX | CD33 Myeloid |
| VGF | Pancreatic Islet |
| VGLL1 | Placenta |
| VGLL3 | Placenta |
| VILL | Colon |
| VIPR1 | Lung |
| VLDLR | Pancreatic Islet |
| VNN2 | Whole Blood |
| VNN3 | CD33 Myeloid |
| VPRBP | Testis Intersitial |
| VPREB1 | CD57 |
| VPS13B | CD8 T cells |
| VPS33B | Testis |
| VPS45 | pineal day |
| VPS53 | Skin |
| VS1G4 | Lung |
| VSX1 | Superior Cervical Ganglion |
| VTCN1 | Trachea |
| WARS2 | X721 B lymphoblasts |
| WASL | Colon |
| WDR18 | X721 B lymphoblasts |
| WDR25 | Lung |
| WDR43 | Lymphoma burkitts Daudi |
| WDR55 | CD4 T cells |
| WDR5B | Superior Cervical Ganglion |

TABLE 1-continued

List of Tissue-Specific Genes Determined
by Deconvolution of Adult Transcriptome

| Gene | Tissue |
|---|---|
| WDR60 | Testis Intersitial |
| WDR67 | CD56 NK Cells |
| WDR70 | BDCA4 Dentritic Cells |
| WDR78 | Testis Seminiferous Tubule |
| WDR8 | Lymphoma burkitts Raji |
| WDR91 | X721 B lymphoblasts |
| WHSC1L1 | Ovary |
| WHSC2 | Lymphoma burkitts Raji |
| WM1 | CD71 Early Erythroid |
| WW1 | Uterus Corpus |
| W6P3 | Superior Cervical Ganglion |
| WNT11 | Uterus Corpus |
| WNT2D | retina |
| WNT3 | Superior Cervical Ganglion |
| WNT4 | Pancreatic Islet |
| WNTSA | Colorectal adenocarcinoma |
| WNT5B, | Prostate |
| WNT6 | Colorectal adenocarcinoma |
| WNT7A | Bronchial Epithelial Cells |
| WNT7B | Skeletal Muscle |
| WNT8B | Skin |
| WRNIP1 | Trigeminal Ganglion |
| Wil | Uterus |
| WWC3 | CD19 Bcells neg. sel. |
| XCL1 | CD56 NK Cells |
| XK | CD71 Early Erythroid |
| XPNPEP2 | Kidney |
| XPO4 | pineal day |
| XPO6 | Whole Blood |
| XPO7 | CD71 Early Erythroid |
| XRCC3 | Colorectal adenocarcinoma |
| YAF2 | Skeletal Muscle |
| YEIX2 | Testis |
| YIF1A | Liver |
| YIPF6 | CD71 Early Erythroid |
| YWHAQ | Skeletal Muscle |
| YY2 | Uterus Corpus |
| ZAK | Dorsal Root Ganglion |
| ZAP70 | CD56 NK Cells |
| MEN. | Dorsal Root Ganglion |
| ZBT610 | Superior Cervical Ganglion |
| ZBTB17 | Lymphoma burkitts Raji |
| ZBT624 | Skin |
| ZBTB3 | Superior Cervical Ganglion |
| ZETB33 | Superior Cervical Ganglion |
| ZBTB40 | CD4 T cells |
| ZBTB43 | CD33 Myeloid |
| ZBTB5 | CD19 Bcells neg. sel. |
| ZBTB6 | Superior Cervical Ganglion |
| ZBTB7B | Ovary |
| ZC3H12A | Smooth Muscle |
| ZC3H14 | Testis Intersitial |
| ZCCHC2 | Salivary gland |
| ZCWPW1 | Testis Germ Cell |
| ZDHHC13 | X721 B lymphoblasts |
| ZDHHC14 | Lymphoma burkitts Raji |
| ZDHHC18 | Whole Blood |
| ZDHHC3 | Testis Intersitial |
| ZER1 | CD71 Early Erythroid |
| ZFHX4 | Smooth Muscle |
| ZFP2 | Superior Cervical Ganglion |
| ZFP30 | Ciliary Ganglion |
| ZFPM2 | Cerebellum |
| ZFR2 | Trigeminal Ganglion |
| ZFINE9 | Cingulate Cortex |
| ZG16 | Colon |
| ZGPAT | Liver |
| ZIC3 | Cerebellum |
| ZKSCAN1 | Pancreas |
| ZKSCAN9 | CD19 Bcells neg. sel. |
| KMAT5 | Liver |
| ZMYM1 | Superior Cervical Ganglion |
| ZMYND10 | Testis |
| ZNF124 | Uterus Corpus |
| ZNF132 | Skin |

TABLE 1-continued

List of Tissue-Specific Genes Determined
by Deconvolution of Adult Transcriptome

| Gene | Tissue |
| --- | --- |
| ZNF133 | CD58 |
| ZNF135 | CD59 |
| ZNF136 | CD8 T cells |
| ZNF114 | Trigeminal Ganglion |
| ZNF140 | Superior Cervical Ganglion |
| ZNF157 | Trigeminal Ganglion |
| ZNF167 | Appendix |
| ZNF175 | Leukemia chronic Myelogenous K601 |
| ZNF177 | Testis Seminiferous Tubule |
| ZNF185 | Tongue |
| ZNF193 | Ovary |
| ZNF200 | Whole Blood |
| ZNF208 | Liver |
| ZNF214 | Superior Cervical Ganglion |
| ZNF215 | Dorsal Root Ganglion |
| ZNF223 | Ciliary Ganglion |
| ZNF224 | CD8 T cells |
| ZNF226 | pineal night |
| ZNF23 | CD71 Early Erythroid |
| ZNF235 | Superior Cervical Ganglion |
| ZNF239 | Testis Seminiferous Tubule |
| ZNF250 | Skin |
| ZNF253 | Superior Cervical Ganglion |
| ZNF259 | Testis |
| ZNF264 | CD4 T cells |
| ZNF267 | Whole Blood |
| ZNF273 | Skin |
| ZNF274 | CD19 Bcells neg. sel. |
| ZNF2800 | Testis Intersitial |
| ZNF286A | Superior Cervical Ganglion |
| ZNF304 | Superior Cervical Ganglion |
| ZNF318 | X721 B lymphoblasts |
| ZNF323 | Superior Cervical Ganglion |
| ZNF324 | Thymus |
| ZNF331 | Adrenal Cortex |
| ZNF34 | Fetal Thyroid |
| ZNF343 | Ciliary Ganglion |
| ZNF345 | Superior Cervical Ganglion |
| ZNF362 | Atrioventricular Node |
| ZNF3850 | Superior Cervical Ganglion |
| ZNF391 | Testis Intersitial |
| ZNF415 | Testis Intersitial |
| ZNF430 | CD8 T cells |
| ZNF434 | Globus Pallidus |
| ZNF443 | Trigeminal Ganglion |
| ZNF446 | Superior Cervical Ganglion |
| ZNF45 | CD60 |
| ZNF451 | CD71 Early Erythroid |
| ZNF460 | Trigeminal Ganglion |
| ZNF467 | Whole Blood |
| ZNF468 | CD56 NK Cells |
| ZNF471 | Skeletal Muscle |
| ZNF484 | Atrioventricular Node |
| ZNF507 | Fetal liver |
| ZNF510 | Appendix |
| ZNF516 | Uterus |
| ZNF550 | Temporal Lobe |
| ZNF556 | Ciliary Ganglion |
| ZNF557 | Ciliary Ganglion |
| ZNF587 | Superior Cervical Ganglion |
| ZNF589 | Superior Cervical Ganglion |
| ZNF606 | Fetal brain |
| ZNF572 | CD71 Early Erythroid |
| ZNF696 | Trigeminal Ganglion |
| ZNF7 | Skeletal Muscle |
| ZNF711 | Testis Germ Cell |
| ZNF717 | Appendix |
| ZNF74 | Dorsal Root Ganglion |
| ZNF770 | Skeletal Muscle |
| ZNF771 | Atrioventricular Node |
| ZNF780A | Superior Cervical Ganglion |
| ZNF79 | Leukemia lymphoblastic MOLT 41 |
| ZNF8 | Superior Cervical Ganglion |
| ZNIF80 | Trigeminal Ganglion |
| ZNF804A | Lymphoma burkitts Daudi |

TABLE 1-continued

List of Tissue-Specific Genes Determined
by Deconvolution of Adult Transcriptome

| Gene | Tissue |
| --- | --- |
| ZNF821 | Testis Intersitial |
| ZNH1T2 | Testis |
| ZP2 | Cerebellum |
| ZPBP | Testis Intersitial |
| ZSCAN16 | CD19 Bcells neg. sel. |
| ZSCAN2 | Skeletal Muscle |
| ZSWIM1 | Ciliary Ganglion |
| ZW10 | Superior Cervical Ganglion |
| ZXDB | Ciliary Ganglion |
| ZZZ3 | CD61 |

The following table (Table 2) lists panel of 94 tissue-specific genes in Example 4 that were verified with qPCR

TABLE 2

Panel of 94 tissue-specific genes in Example
4 that were verified with qPCR.

| Gene | Tissue |
| --- | --- |
| PMCH | Amygdala |
| HAPLN1 | Bronchial epithelial cells |
| PRDM12 | Cardiac myocytes |
| ARPP-21 | Caudate nucleus |
| GPR88 | Caudate nucleus |
| PDE10A | Caudate nucleus |
| CBLN1 | Cerebellum |
| CDH22 | Cerebellum |
| DGKG | Cerebellum |
| CDR1 | Cerebellum |
| FAT2 | Cerebellum |
| GABRA6 | Cerebellum |
| KCNJ12 | Cerebellum |
| KIAA0802 | Cerebellum |
| NEUROD1 | Cerebellum |
| NRXN3 | Cerebellum |
| PPF1A4 | Cerebellum |
| ZIC1 | Cerebellum |
| SAA4 | Cervix |
| SERPINC1 | Cervix |
| CALML4 | Colon |
| DSC2 | Colon |
| ACTC1 | Heart |
| NKX2-5 | Heart |
| CASQ2 | Heart |
| CKMT2 | Heart |
| HRC | Heart |
| HSPB3 | Heart |
| HSPB7 | Heart |
| ITGB1BP3 | Heart |
| MYL3 | Heart |
| MYL7 | Heart |
| MYOZ2 | Heart |
| NPPB | Heart |
| CSRP3 | Heart |
| MYBPC3 | Heart |
| PGAM2 | Heart |
| TNN13 | Heart |
| SLC4A3 | Heart |
| TNNT2 | Heart |
| SYNPO2L | Heart |
| AVP | Liver |
| ACTB | Housekeeping |
| GAPDH | Housekeeping |
| MAB21L2 | Housekeeping |
| HCRT | Hypothalamus |
| OXT | Hypothalamus |
| BBOX1 | Kidney |
| AQP2 | Kidney |
| KCNJ1 | Kidney |
| FMO1 | Kidney |
| NAT8 | Kidney |

TABLE 2-continued

| Panel of 94 tissue-specific genes in Example 4 that were verified with qPCR. | |
| --- | --- |
| Gene | Tissue |
| XPNPEP2 | Kidney |
| PDZK1IP1 | Kidney |
| PTH1R | Kidney |
| SLC12A1 | Kidney |
| SLC13A3 | Kidney |
| SLC22A6 | Kidney |
| SLC22A8 | Kidney |
| SLC7A9 | Kidney |
| UMOD | Kidney |
| SLC17A3 | Kidney |
| AKR1C4 | Liver |
| C8G | Liver |
| APOF | Liver |
| AQP9 | Liver |
| CYP2A6 | Liver |
| CYP1A2 | Liver |
| CYP2C8 | Liver |
| CYP2D6 | Liver |
| CYP2E1 | Liver |
| ITIH4 | Liver |
| HRG | Liver |
| FTCD | Liver |
| IGFALS | Liver |
| RDH16 | Liver |
| SDS | Liver |
| SLC22A1 | Liver |
| TBX3 | Liver |
| SLC27A5 | Liver |
| KCNK12 | Olfactory bulb |
| MPZ | Olfactory bulb |
| C21ORF7 | Whole blood |
| FFAR2 | Whole blood |
| FCGR3A | Whole blood |
| EMR2 | Whole blood |
| FAM5B | Whole blood |
| FCGR3B | Whole blood |
| FPR2 | Whole blood |
| MLH3 | Whole blood |
| PF4 | Whole blood |
| PF4V1 | Whole blood |
| PPBP | Whole blood |
| TLR1 | Whole blood |
| TNFRSF10C | Whole blood |
| ZDHHC18 | Whole blood |

Example 5: Using Tissue-Specific Cell-Free RNA to Assess Alzheimer's

Figure 17:
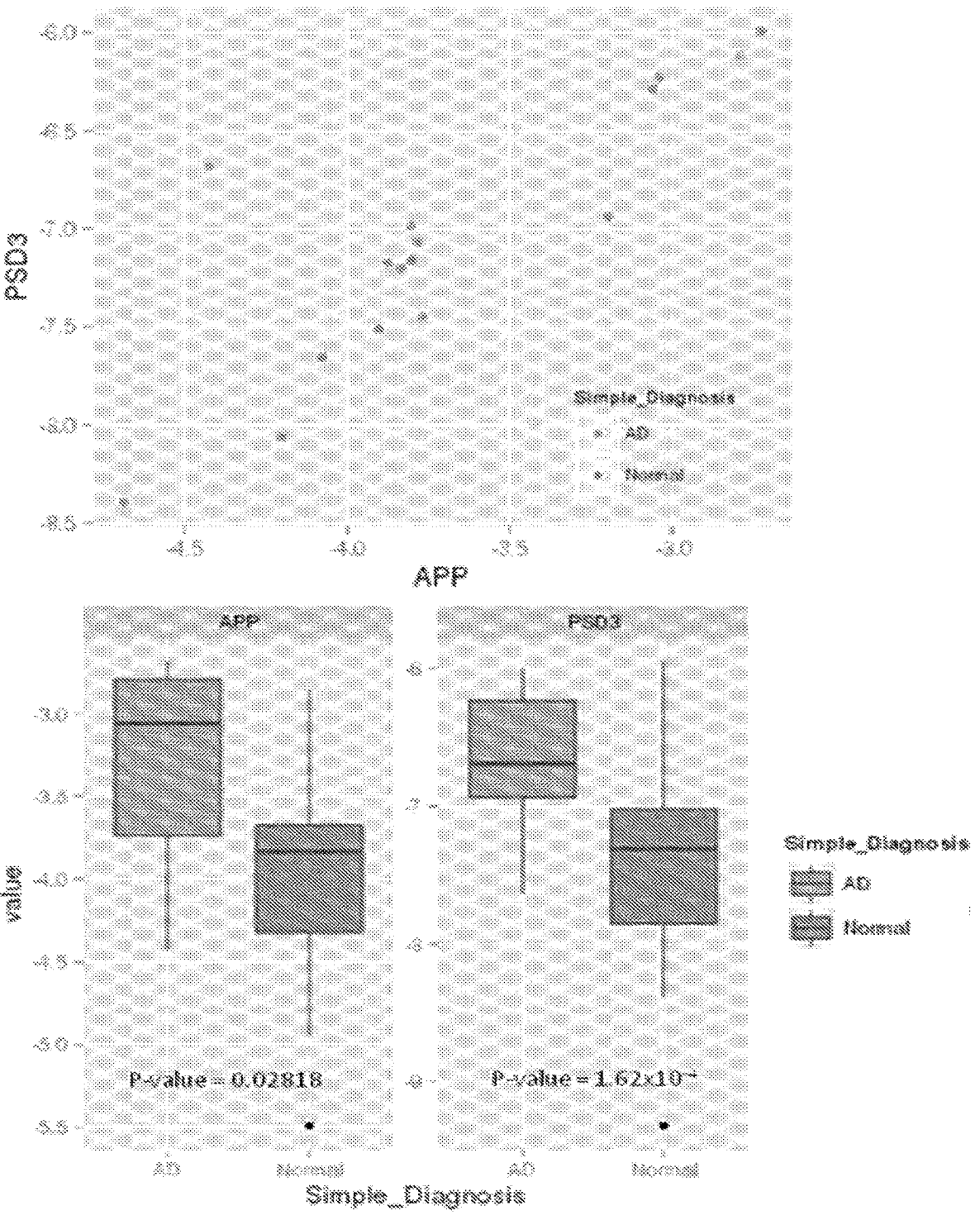
FIG. 17 illustrates identifying brain-specific cell-free RNA transcripts that differ between Alzheimer's subjects and control subjects.

The analysis of fetal brain-specific transcripts, in Examples 2 and 3, leads to the assessment of brain-specific transcripts for neurological disorder. Particularly, the qPCR brain panel detected fetal brain-specific transcripts in maternal blood, whereas the whole transcriptome deconvolution analysis in our nonpregnant adult samples, in Examples 2 and 3, revealed that the hypothalamus is a significant contributor to the whole cell-free transcriptome. Since the hypothalamus is bounded by specialized brain regions that lack an effective blood-brain barrier, cell-free DNA in the blood was examined in the current study to measure neuronal death, qPCR was used to measure the expression levels of selected brain transcripts in the plasma of both Alzheimer's patients and age-matched normal controls. These measurements were made for a cohort of 16 patients: 6 diagnosed as Alzheimer's and 10 normal subjects. FIG. 17 depicts the measurements of PSD3 and APP cell-free RNA transcript levels in plasma. As provided in FIG. 17, the levels of PSD3 and APP cell-free RNA transcripts are elevated in Alzheimer's (AD) patients as compared to normal patients and can be used to characterize the different patient populations.

The APP transcript encodes for the precursor molecule whose proteolysis generates f3 amyloid, which is the primary component of amyloid plaques found in the brain of Alzheimer's disease patients. Preliminary measurements of the plasma APP transcript corroborate the known biology behind progression of Alzheimer's disease and showed a significant increase in patients with Alzheimer's disease compared with normal subjects, suggesting that plasma APP mRNA levels may be a good marker for diagnosing Alzheimer's disease. Similarly, the gene PSD3, which is highly expressed in the nervous system and localized to the postsynaptic density based on sequence similarities, shows an increase in the plasma of patients with Alzheimer's disease. By plotting the Ct values of APP against PSD3, AD patients were clustered away from the normal patients. In light of the cluster variants, cell-free RNA may serve as a blood-based diagnostic test for Alzheimer's disease and other neurodegenerative disorders.

Example 6: Assessing Neurological Disorders with Brain-Specific Transcript

Overview

This study expands upon Example 5 and was designed to determine brain-specific tissue transcripts that correlate with the various stages of Alzheimer's disease. The study examined a cohort of patients from different centers that have previously collected Alzheimer's patents and age controlled references. There were a total of 254 plasma samples available from the different centers. Cell free RNA was extracted from each of the samples. The extracted cell free RNA from each of these samples were then assayed using high throughput qPCR on the Biomark Fluidigm system. Each of the samples was assayed using a panel of 48 genes of which 43 genes are known to be brain specific. The resulting measurements from each of the samples were put through a very stringent quality control process. The first step includes measuring the distribution of housekeeping genes: ACTB and GAPDH. By observing the levels of housekeeping genes across the sample from different batches, batches with significantly lower levels of housekeeping genes were removed from downstream analysis. The next step in quality control is by the number of failed gene assays in each of the patient sample. Sample where 8 or more assays failed to amplify are removed. This results in 125 good quality samples:

I. 27 Alzheimer's Patients (AD)
    II. 52 Mild Cognitive Impairment Patients (MCI)
    III. 46 Normal patients.
    IV.

Analysis and Results

Figure 27:
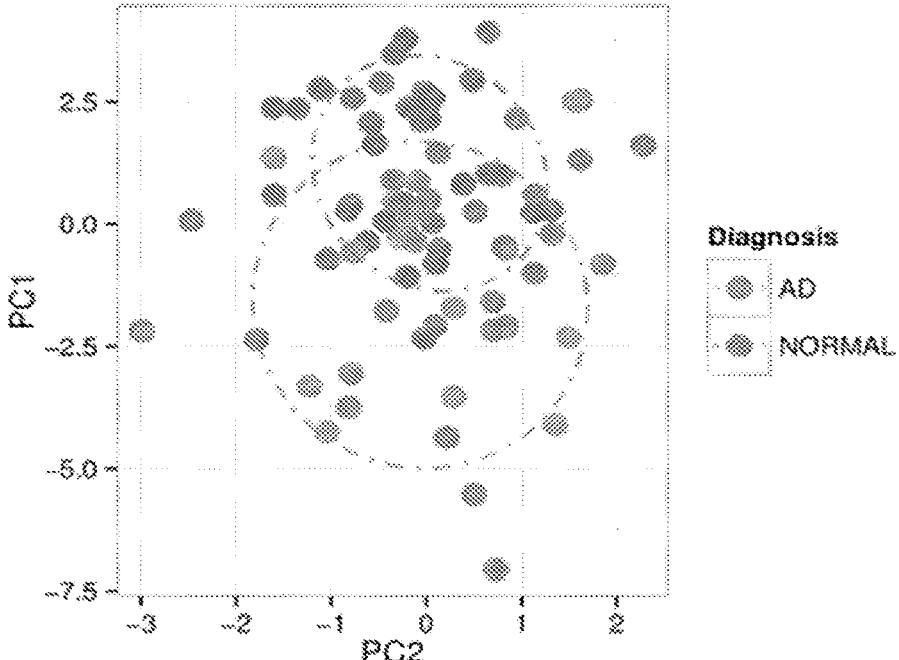
FIG. 27 depicts a Principle Component Analysis (PCA) space reflecting the unsupervised clustering of the patients using the gene expression data from the 48 genes assay.

An unsupervised method of Principle Component Analysis (PCA) was applied to the qPCR gene expression of the 43 brain-specific transcripts in order to differentiate between Alzheimer's and Normal patients. FIG. 27 illustrates the PCA space reflecting the unsupervised clustering of the patients using the gene expression data from the 48-gene assay. As shown in FIG. 27 two different populations are formed which correspond to the neurological disease state of the patients.

Additionally, a Wilcox non-parametric statistical test was performed between Alzheimer's and normal patients for each of the brain specific transcripts. The resulting p-values were bonferroni corrected for multiple testing. Brain specific transcripts whose p-values that are significant at the 0.05 levels were cataloged as transcripts that high distinguishing power between alzheimer's and normal patients. Amongst all the assayed brain specific transcripts, two of them are elevated in Alzheimer patients: APP and PSD3. Another 7 transcripts were below normal levels at a significant level: MOBP; MAG: SLC2AI; TCF7L2; CDH22; CNTF and PAQR6. FIG. 28 shows the boxplot of the different levels of APP transcripts across the different patient groups and the corrected P-value indicating the significance of the transcripts in distinguishing Alzheimer's. FIG. 29 illustrates the alternate trends where the levels of the measure brain transcript MOBP were lower in the Alzheimer population as compared to the normal population. MOBP is a myelin-associated oligodendrocyte protein-coding gene which is known to play a role in compacting or stabilizing the myelin sheath.

Methods of Normalization for Comparison Across Sample Batches

Considerable heterogeneity may be present between different batches of samples collected. A normalization scheme may be deployed to allow for valid comparison across samples from different batches, and such scheme was deployed in the present study. For each gene assay within each batch, the delta ct values of each sample was used to generate a z-score by using the mean and standard deviation inferred from the population of normal samples within the batch. This z-score is then used to as the normalized expression value for downstream analysis, as discussed below.

Figure 30:
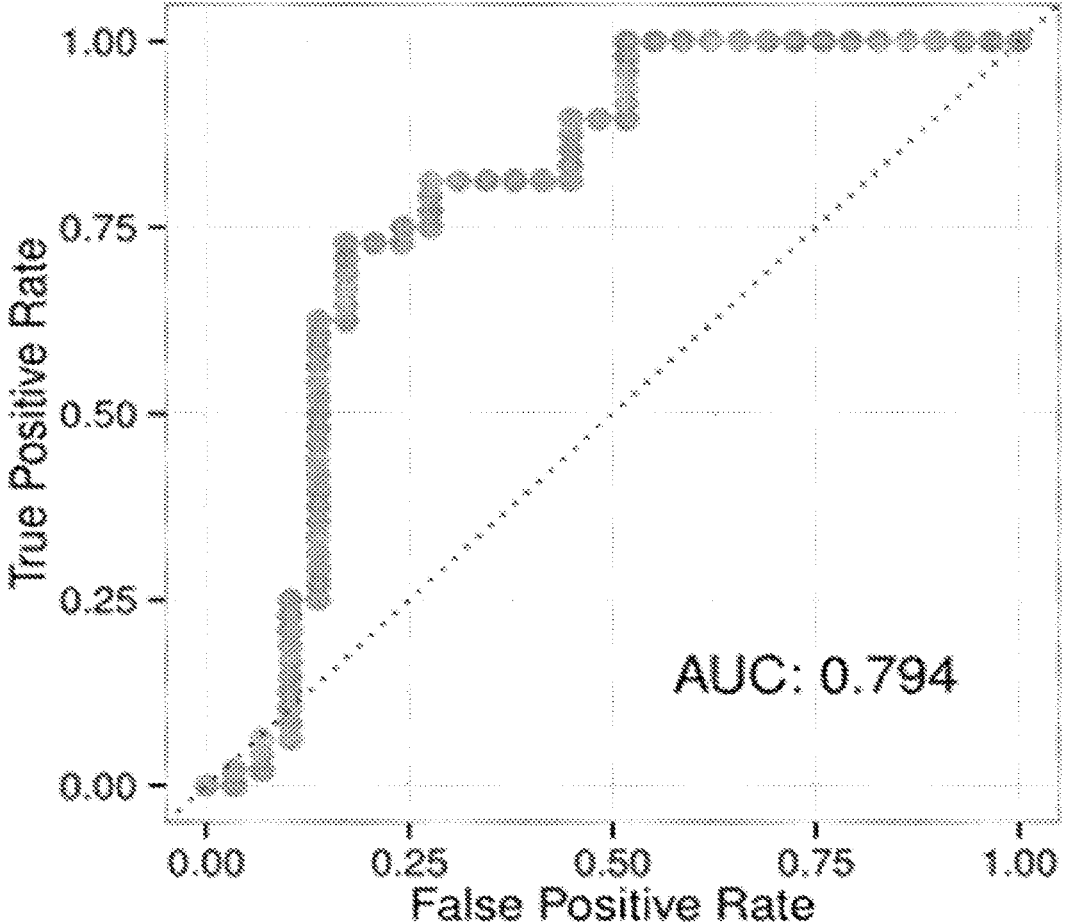
FIG. 30 depicts classification results using combined Z-scores.

Classification Results using Combined Z-Scores (See FIG. 30)

To incorporate the different measurements across the brain specific genes into a single distinct measure for classification of the patients, the method of combined z, scores was employed. The combined z-scores measure the deviation of the brain specific transcripts from the mean expected value of the normal controls and combine these deviations into a single measure for distinguishing Alzheimer's. To analyze the utility of such a measure in distinguishing Alzheimer's, a receiver-operator analysis was performed and achieved an area under curve (AUC) of 0.79 (See FIG. 30).

Incorporation by Reference

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method comprising:
(a) obtaining a whole blood sample from a subject;
(b) extracting cell-free ribonucleic acid (RNA) from plasma of the whole blood sample of the subject;
(c) converting the cell-free RNA into complementary deoxyribonucleic acid (cDNA) thereby producing sample cDNA;
(d) amplifying the sample cDNA to produce amplified DNA;
(e) sequencing the amplified DNA to produce sequence information;
(f) quantitating the sequence information to determine a level of the sample cDNA that encodes one or more RNA transcripts comprising brain-specific RNA transcripts selected from the group consisting of APP, PSD3, MOBP, MAG, SLC2A1, TCF7L2, CDH22, CNTF and PAQR6;
and
(g) determining that the subject has Alzheimer's disease, based on the quantified levels of the one or more RNA transcripts.

2. The method of claim 1, wherein (b) further comprises extracting total RNA from the plasma of the whole blood sample.

3. The method of claim 2, wherein extracting the total RNA comprises contacting the plasma of the whole blood sample with chloroform to produce a mixture.

4. The method of claim 3, further comprising centrifuging the mixture to produce an aqueous layer.

5. The method of claim 4, further comprising isolating the total RNA from the aqueous layer.

6. The method of claim 5, further comprising performing DNase digestion of the total RNA.

7. The method of claim 1, wherein the whole blood sample has a volume of 7 milliliters to 15 milliliters.

8. The method of claim 1, wherein the amplifying comprises polymerase chain reaction (PCR).

9. The method of claim 8, wherein the PCR comprises indiscriminate PCR.

10. The method of claim 1, wherein the sequencing comprises whole transcriptome sequencing.

11. The method of claim 1, further comprising performing microarray analysis of the sample cDNA.

12. The method of claim 1, further comprising performing quantitative polymerase chain reaction (PCR) analysis of the sample cDNA.

\* \* \* \* \*